US012612439B2

(12) United States Patent　(10) Patent No.:　US 12,612,439 B2
Moser et al.　(45) Date of Patent:　Apr. 28, 2026

(54) MUTANT BACTERIORHODOPSIN-LIKE-CHANNELRHODOPSIN ION CHANNEL

(71) Applicants: Georg-August-Universität Göttingen Stiftung Öffentlichen Rechts, Universitätsmedizin, Göttingen (DE); OptoGenTech GmbH, Göttingen (DE)

(72) Inventors: Tobias Moser, Goettingen (DE); Thomas Mager, Kassel (DE); Maria Zerche, Göttingen (DE)

(73) Assignees: GEORG-AUGUST-UNIVERSITÄT GÖTTINGEN STIFTUNG ÖFFENTLICHEN RECHTS, UNIVERSITÄTSMEDIZIN, Göttingen (DE); OPTOGENTECH GMBH, Göttingen (DE)

( * ) Notice: Subject to any disclaimer, the term of this patent is extended or adjusted under 35 U.S.C. 154(b) by 0 days.

(21) Appl. No.: 18/164,297

(22) Filed: Feb. 3, 2023

(65) Prior Publication Data

US 2023/0250143 A1　Aug. 10, 2023

(30) Foreign Application Priority Data

Feb. 4, 2022　(EP) .................................... 22155173

(51) Int. Cl.
| | |
|---|---|
| *C07K 14/47* | (2006.01) |
| *A61K 38/17* | (2006.01) |
| *A61K 48/00* | (2006.01) |
| *A61P 27/02* | (2006.01) |
| *A61P 27/16* | (2006.01) |

(52) U.S. Cl.
CPC .......... *C07K 14/47* (2013.01); *A61K 38/1709* (2013.01); *A61K 48/0075* (2013.01); *A61P 27/02* (2018.01); *A61P 27/16* (2018.01)

(58) Field of Classification Search
None
See application file for complete search history.

(56) References Cited

U.S. PATENT DOCUMENTS

| | | | | |
|---|---|---|---|---|
| 8,748,578 | B2 * | 6/2014 | Bamberg ................. | A61P 27/02 435/235.1 |
| 8,759,492 | B2 | 6/2014 | Lin et al. | |
| 2013/0017597 | A1 | 1/2013 | Hegemann et al. | |
| 2020/0087358 | A1 | 3/2020 | Gradinaru et al. | |

FOREIGN PATENT DOCUMENTS

| | | | |
|---|---|---|---|
| WO | WO 03/084994 | A2 | 10/2003 |
| WO | WO 2012/032103 | A1 | 3/2012 |
| WO | WO 2013/071231 | A1 | 5/2013 |
| WO | WO 2017/207745 | A1 | 12/2017 |
| WO | WO 2017/207761 | A1 | 12/2017 |
| WO | WO-2020150093 | A1 * | 7/2020 ........... A61N 5/0601 |

OTHER PUBLICATIONS

Heydenreich et al. (Bio Protoc. Jan. 5, 2020; 10(1): e3484) (Year: 2020).*
Agus et al., "Optogenetic methods in drug screening: technologies and applications," Current Opinion in Biotechnology, vol. 48, 2017, pp. 8-14.
Berndt et al., "High-efficiency channelrhodopsins for fast neuronal stimulation at low light levels," PNAS, vol. 108, No. 18, May 3, 2011, pp. 7595-7600.
Berndt et al., "Structural foundations of optogenetics: Determinants of channelrhodopsin ion selectivity," PNAS, vol. 113, No. 4, Dec. 22, 2015, pp. 822-829.
Boyden et al., "Millisecond-timescale, genetically targeted optical control of neural activity," Nature Neuroscience, vol. 8, No. 9, Sep. 2005 (Published online Aug. 14, 2005), pp. 1263-1268.
Dieter et al., "Towards the optical cochlear implant: optogenetic approaches for hearing restoration," EMBO Molecular Medicine, vol. 12, e11618, 2020, pp. 1-16.
Extended European Search Report for European Application No. 22155173.2, dated Aug. 10, 2022.
Feldbauer et al., "Channelrhodopsin-2 is a leaky proton pump," PNAS, 2009, pp. 12317-12322.
Govorunova et al., "Natural light-gated anion channels: A family of microbial rhodopsins for advanced optogenetics," Science, Jun. 25, 2015, pp. 647-650 (7 pages total).
Govorunova et al., "Kalium rhodopsins: Natural light-gated potassium channels," bioRxiv, 2021, pp. 1-9.
Gradinaru et al., "Molecular and Cellular Approaches for Diversifying and Extending Optogenetics," Cell, vol. 141, Apr. 2, 2010, pp. 154-165.
Jardon-Valadez et al., "Electrostatic interactions and hydrogen bond dynamics in chloride pumping by halorhodopsin," Biochim Biophys Acta., Dec. 2014, vol. 1837, No. 12, pp. 1964-1972.
Karlin et al., "Applications and statistics for multiple high-scoring segments in molecular sequences," Proc. Natl. Acad. Sci. USA, vol. 90, Jun. 1993, pp. 5873-5877.
Karlin et al., "Methods for assessing the statistical significance of molecular sequence features by using general scoring schemes," Proc. Natl. Acad. Sci. USA, vol. 87, Mar. 1990, pp. 2264-2268.
Keppeler et al., "Ultrafast optogenetic stimulation of the auditory pathway by targeting-optimized Chronos," The EMBO Journal, 2018, vol. 37, e99649, pp. 1-15.
Kishi et al., "Structural basis for channel conduction in the pump-like channelrhodopsin ChRmine," bioRxiv, 2021, pp. 1-74.

(Continued)

*Primary Examiner* — Sergio Coffa
(74) *Attorney, Agent, or Firm* — Birch, Stewart, Kolasch & Birch, LLP

(57) ABSTRACT

The present invention relates to a mutant ion channel capable of being activated by light ('light-activated' ion channel) and having improved properties, nucleic acids and expression vectors encoding the mutant ion channel, cells comprising such nucleic acid or expression vector, devices containing the mutant ion channel, nucleic acid or expression vector as well as respective uses and methods.

14 Claims, 9 Drawing Sheets

Specification includes a Sequence Listing.

(56)         References Cited

OTHER PUBLICATIONS

Klapoetke et al., "Independent optical excitation of distinct neural populations," Nature Methods, vol. 11, No. 3, Mar. 2014, pp. 338-346 (17 pages total).

Kleinlogel et al., "Emerging Approaches for Restoration of Hearing and Vision," Physiological Reviews, vol. 100, 2020, pp. 1467-1525.

Kleinlogel et al., "Ultra light-sensitive and fast neuronal activation with the Ca2+-permeable channelrhodopsin CatCh," Nature Neuroscience, vol. 14, No. 4, Apr. 2011, pp. 513-518 (8 pages total).

Lin et al., "Characterization of Engineered Channelrhodopsin Variants with Improved Properties and Kinetics," Biophysical Journal, vol. 96, Mar. 2009, pp. 1803-1814.

Lin et al., "ReaChR: a red-shifted variant of channelrhodopsin enables deep transcranial optogenetic excitation," Nature Neuroscience, vol. 16, No. 10, Oct. 2013, pp. 1499-1508 (12 pages total).

Lorenz-Fonfria et al., "Temporal evolution of helix hydration in a light-gated ion channel correlates with ion conductance," PNAS, Oct. 12, 2015, pp. E5796-E5804.

Lorenz-Fonfria et al., "Transient protonation changes in channelrhodopsin-2 and their relevance to channel gating," PNAS, Mar. 18, 2013, pp. E1273-E1281.

Mager et al., "High frequency neural spiking and auditory signaling by ultrafast red-shifted optogenetics," Nature Communications, vol. 9, No. 1750, 2019, pp. 1-14.

Marshel et al., "Cortical layer-specific critical dynamics triggering perception," Science, vol. 365, No. 558, Aug. 9, 2019, pp. 1-12.

Muller et al., "Light-Induced Helix Movements in Channelrhodopsin-2," J Mol Biol, vol. 427, 2015, pp. 341-349.

Myers et al., "Optimal alignments in linear space," Cabios, vol. 4, No. 1, 1988, pp. 11-17.

Nagel et al., "Channelrhodopsin-1: A Light-Gated Proton Channel in Green Algae," Science, vol. 296, Jun. 28, 2002, pp. 2395-2398.

Nagel et al., "Channelrhodopsin-2, a directly light-gated cation-selective membrane channel," PNAS, vol. 100, No. 24, Nov. 25, 2003, pp. 13940-13945.

Needleman et al., "A General Method Applicable to the Search for Similarities in the Amino Acid Sequence of Two Proteins," J. Mol. Biol., vol. 48, 1970, pp. 443-453.

Pearson et al., "Improved tools for biological sequence comparison," Proc. Natl. Acad. Sci. USA, vol. 85, Apr. 1988, pp. 2444-2448.

Sahel et al., "Partial recovery of visual function in a blind patient after optogenetic therapy," Nature Medicine, vol. 27, Jul. 2021, pp. 1223-1229.

Sattig et al., "Light-Induced Movement of the Transmembrane Helix B in Channelrhodopsin-2," Angew. Chem. Int. Ed., vol. 52, 2013, pp. 9705-9708.

Sineshchekov et al., "Conductance Mechanisms of Rapidly Desensitizing Cation Channelrhodopsins from Cryptophyte Algae," mBio, vol. 11, Issue 2, Apr. 21, 2020, pp. 1-12.

Smith et al., "Comparison of Biosequences," Advances in Applied Mathematics, vol. 2, 1981, pp. 482-489.

Volkov et al., "Structural insights into ion conduction by channelrhodopsin 2," Science, vol. 358, No. 1018, Nov. 24, 2017, pp. 1-8 (10 pages total).

Zerche et al., "Identification and optimization of channelrhodopsin variants for optogenetic hearing restoration," Institute for Auditory Neuroscience & Inner Ear Lab, University Medical Center Gottingen, Germany, 2022, 1 page total.

Zhang et al., "Optogenetic approaches to drug discovery in neuroscience and beyond," Trends Biotechnol., vol. 35, No. 7, Jul. 2017, pp. 625-639.

Zhang et al., "Red-shifted optogenetic excitation: a tool for fast neural control derived from Volvox carteri," Nat Neurosci., vol. 11, No. 6, Jun. 2008, pp. 631-633.

* cited by examiner e f

500 ms

A

B

MUTANT BACTERIORHODOPSIN-LIKE-CHANNELRHODOPSIN ION CHANNEL

REFERENCE TO AN ELECTRONIC SEQUENCE LISTING

The contents of the electronic sequence listing (sequence listing 9A-158 513.xml; Size: 29,206 bytes; and Date of Creation: Feb. 1, 2023) is herein incorporated by reference in its entirety.

FIELD OF THE INVENTION

The present invention relates to a novel mutant ion channel capable of being activated by light ('light-activated' ion channel) and having improved properties, nucleic acids and expression vectors encoding the mutant ion channel, cells comprising such nucleic acid or expression vector, devices containing the mutant ion channel, nucleic acid or expression vector as well as respective uses and methods.

BACKGROUND OF THE INVENTION

Channelrhodopsins (ChRs) are light-activated ion channels comprising 7 transmembrane helices (7-transmembrane-helix motif, 7TM motif), which are used for the control of excitable cell activity with light (optogenetic control) [ref. 1-4]. Optogenetic approaches are of key importance for a deeper understanding of excitable cell networks and bear potential for the development of innovative medical treatments such as the recovery of vision and hearing [ref. 5 and 6].

ChRs enable both, light-controlled silencing and photostimulation of neurons. Neuronal silencing is carried out with anion selective ChRs [ref. 7] or potassium selective ChRs [ref. 8]. The optogenetic activation of neurons is accomplished using cation selective ChRs with low ion selectivity [ref. 2 and 9]. For different applications ChRs with suitable kinetics, ion selectivity and spectral properties were identified by the biophysical characterization of microbial type rhodopsins or generated by site directed mutagenesis of key residues for ChR function. Examples are the mutant L132C (CatCh; WO 2012/032103 and ref. 10) of the *Chlamydomonas reinhardtii* channel rhododopsin ChR2 (SEQ ID NO: 1, WO 03/084994 and ref. 2), the red light activated *Chlamydomonas noctigama* channelrhodopsin Chrimson (SEQ ID NO: 2, WO 2013/071231 and ref. 9), the Volvox channelrhodopsin (SEQ ID NO: 3, VChR1, ref. 11) and the chimera ReaChR (SEQ ID NO: 4, Red-absorbing ChannelRhodopsin; U.S. Pat. No. 8,759,492 B2, and ref. 12).

It was demonstrated that helix 6 modifications could accelerate channel closing in green algal ChRs (WO 2017/207761, WO 2017/207745, ref. 13). Examples are the mutations Y261F, S267M and Y268F and the combination of the corresponding mutations in Chrimson. Further examples are ChR2 F219Y, VChR1 F214Y and ReaChR F259Y.

Optogenetic control of excitable cell activity faces limitations caused by the low single-channel conductance of green algal ChRs (ChR2, $\gamma{\sim}40$ fS, ref. 14). Further limitation is imposed by light dependent desensitization, which restricts photocurrent size. Robust membrane-targeted expression of the optogenetic activator and the application of high irradiance light pulses still allow for control of light induced spiking but can be challenging to implement in vivo and harbours the risk of photo- and cytotoxicity. Site directed mutagenesis yielded green algal ChR variants in which desensitization is significantly reduced and consequently allow for efficiency enhanced photostimulation [ref. 10 and 15] As light pulse induced phototoxicity decreases with increasing wavelength, this risk can be minimized by employing ChR variants which have action spectra that are red-shifted compared to the action spectrum of the most commonly used ChR variant ChR2 from *Chlamydomonas reinhardtii* ($\lambda_{max}{\sim}460$ nm, ref. 2).

R/CCR1 ("ChRmine") (SEQ ID NO: 5) from the marine cryptophyte *Rhodomonas lens* is a so-called bacteriorhodopsin-like-channelrhodopsin [ref 16-18], also referred to as DTD Channelrhodopsin. R/CCR1 assembles as a trimer. Based on the high resolution cryo-electron microscopy structure and functional investigations the existence of a hydrophilic pore that extends through the center of the trimer in addition to three individual monomer pores was postulated. R/CCR1 has a red-shifted action spectrum ($\lambda_{max}{=}520$ nm) compared to ChR2 ($\lambda_{max}{\sim}460$ nm), and generates comparatively high photocurrents. However, its utility for chronic stimulation is impaired by a strong light-dependent desensitization of the photocurrent.

Accordingly, there is need for variants of ChR R/CCR1 with reduced light-dependent desensitization which allow for sustainable neuronal photostimulation with enhanced efficiency.

SUMMARY OF THE INVENTION

Helix 6 of the 7-transmembrane-helix motif is one of the moving helices upon light-activation in green algal ChRs [ref. 19 and 20], in which it plays a role in controlling light dependent protonation reactions, which govern open to closed state transitions [ref. 13, 21 and 22]. The inventors performed a study on the bacteriorhodopsin-like channelrhodopsin R/CCR1, in which the effect of helix 6 mutations on channel function was investigated. In this study, the present inventors surprisingly found, and experimentally verified in NG108-15 cells (see examples 1 and 2 herein), that mutation of positions 218 and 220 in helix 6 of R/CCR1 and the combination of the aforementioned mutations significantly reduced light-dependent desensitization of R/CCR1.

The reduced light-dependent desensitization in R/CCR1 is a particular advantage of the mutant ion channels and related subject-matter described herein because this reduction allows for large and low-variability photocurrents upon illumination with light pulses of the long wavelength range of visible light and therefore for photostimulation of excitable cells at low light intensities for long periods of time (see example 3 herein). Such lower light requirement is advantageous in medical treatments such as in optogenetic vision and hearing restoration due to the reduced need for light amplification for vision restoration and the power requirements for the light amplifying goggles for vision restoration as well as for the optical cochlear implant in hearing restoration. Additionally, such lower light requirement is advantageous to reduce the risk of phototoxicity in medical applications. Correspondingly, the inventors' identification of positions 218 and 220 of R/CCR1 as positions where amino acid substitution may lead to improvements, in particular the above-described reduce light-dependent desensitization, therefore opens up a whole new class of advantageous ion channels for various medical and non-medical applications.

The present invention relates to a mutant ion channel that is capable of being activated by light and comprises an amino acid substitution at one or both of the positions corresponding to positions T218 and S220 of RICCR1 set forth in SEQ ID NO: 5, as defined in the claims.

Further disclosed herein are a nucleic acid comprising a nucleotide sequence coding for the mutant ion channel as disclosed herein as well as an expression vector comprising a nucleotide sequence coding for the mutant ion channel or the nucleic acid as disclosed herein.

Also disclosed is a cell which comprises the nucleic acid construct or the expression vector as disclosed herein.

Further disclosed are the non-therapeutic use of the mutant ion-channel, or a nucleic acid or expression vector encoding same, as disclosed herein, for rendering cells sensitive to stimulation with light; a method of using said mutant ion-channel, nucleic acid or expression vector for rendering cells sensitive to stimulation with light; and methods for illuminating a targeted tissue or modulating the voltage potential of cells in response to stimulation of light which use the mutant ion channel. Said methods and uses are as defined in the claims.

Additionally, a device as defined in the claims is provided which comprises the mutant ion channel, or the nucleic acid or expression vector encoding same, as disclosed herein.

A further aspect of the present disclosure refers to a mutant ion channel, or a nucleic acid or expression vector encoding same, as described herein, for use in a method of treating or ameliorating loss of vision, or for use in a method of treating or ameliorating loss of hearing.

A further aspect of the present disclosure refers to a method of using a mutant ion channel, or a nucleic acid or expression vector encoding same, or a cell expressing said mutant ion channel, as described herein, for treating or ameliorating loss of vision, or for treating or ameliorating loss of hearing. For example, a nucleic acid or expression vector encoding a mutant ion channel as described herein, can be transferred into the spiral ganglion neurons (SGNs) of a human or a non-human animal in need of treatment or amelioration of a loss of hearing. In particular embodiments, the vector is vector suitable for virus-mediated gene transfer, e.g., using an AAV. Subsequent expression of the mutant ion channel in the SGNs (after the gene transfer) renders them light-sensitive and allows for at least partial restoration of hearing with an optical cochlear implant.

The various aspects of the invention are defined in the independent claims. Preferred embodiments are contained in the dependent claims.

DETAILED DESCRIPTION OF THE PREFERRED EMBODIMENTS

In a first aspect, a mutant ion channel is disclosed which is capable of being activated by light.

The mutant ion channel comprises a 7-transmembrane-helix motif (i.e. is a transmembrane protein). Said 7-trans-membrane-helix motif contains the amino acid substitution(s) characterizing the present invention, namely an amino acid substitution at one or both of the positions within said motif of the mutant ion channel which correspond to positions T218 and S220 of RICCR1 set forth in SEQ ID NO: 5. The mutant ion channel thus differs from the wild-type ion channel RICCR1 set forth in SEQ ID NO: 9 by at least said amino acid substitution at one or both of the positions corresponding to positions T218 and S220 of SEQ ID NO: 5.

The 7-transmembrane-helix motif of the mutant ion channel may have—with increasing preference—at least 70%, at least 75%, at least 80%, at least 85%, at least 90%, at least 92%, at least 94%, at least 96%, at least 98%, or at least 99% identity to the full-length sequence of SEQ ID NO: 9.

Further, the mutant ion channel may be characterized by a particular degree of sequence identity to the full-length sequence of the wild-type ion channel RICCR1 set forth in SEQ ID NO: 5. In particular, the mutant ion channel may comprise an amino acid sequence having—with increasing preference—at least 75%, at least 80%, at least 85%, at least 90%, at least 92%, at least 94%, at least 96%, at least 98%, or at least 99% identity to the full-length sequence of SEQ ID NO: 5.

Generally, an amino acid sequence has "at least x % identity" to another amino acid sequence, e.g. SEQ ID NO: 9 or SEQ ID NO: 5 as indicated herein, when the sequence identity between those two amino acid sequences is at least x % over the full length of said other amino acid sequence, e.g. SEQ ID NO: 9 or SEQ ID NO: 5. As used herein, "sequence identity" or "identity" in the context of two amino acid sequences refers to a specified percentage of residues in the two sequences which are the same when the sequences are aligned for maximum correspondence, and can be determined by sequence comparison algorithms (which are typically part of sequence alignment software), or by visual inspection and calculation of the percentage of aligned identical amino acid residues. Thus, amino acid identity can generally be determined by methods of amino acid sequence alignment and calculation of the percentage of aligned identical amino acid residues. Such methods are routine to the person skilled in the art, and software for performing amino acid sequence alignments and calculating the percentage of sequence identity is well known in the art and readily available. For example, such alignments and determination of percent identity can be performed using publicly available computer homology programs such as the "EMBOSS" program provided at the EMBL homepage at http://www.ebi.ac.uk/Tools/psa/emboss_needle/, using the default settings provided therein. Examples of mathematical algorithms for determining the percent identity between any two sequences include, e.g., the algorithm of Myers and Miller, CABIOS, 4:11 (1988); the local homology algorithm of Smith et al, Adv. Appl. Math., 2:482 (1981); the search-for-similarity-method of Pearson and Lipman, Proc. Natl. Acad. Sci. USA, 85:2444 (1988); the algorithm of Karlin and Altschul, Proc. Natl. Acad. Sci. USA, 87:2264 (1990); modified as in Karhn and Altschul, Proc. Natl. Acad. Sci. USA, 90:5873 (1993); and the homology alignment algorithm of Needleman and Wunsch, J. Mol. Biol, 48:443 (1970); wherein the latter is preferred herein.

The mutant ion channel disclosed herein is capable of being activated by light. In particular, this capability can be the capability of the mutant ion channel to provide a photocurrent in a cell which comprises the ion channel in its plasma membrane and is exposed to light, preferably light of a wavelength in the range of 400-600 nm, in particular 450-570 nm, more particularly 500-540 nm.

Preferably said photocurrent provided by the mutant ion channel is characterized by a stationary photocurrent density of—with increasing preference—at least 50%, at least 60%, at least 70%, at least 80%, at least 90%, or at least 100% of the stationary photocurrent density provided by the wild-type ion channel RICCR1 set forth in SEQ ID NO: 5; or in particular by a mean stationary photocurrent density of—with increasing preference—at least 50%, at least 60%, at least 70%, at least 80%, at least 90%, or at least 100% of the mean stationary photocurrent density provided by the wild-type ion channel RICCR1 set forth in SEQ ID NO: 5.

The mean stationary photocurrent density can be calculated from the stationary photocurrent densities of at least 5, in particular at least 10, more particularly at least 15, e.g. 5-100, in particular 10-75 or more particularly 15-60, individual NG108-15 cells expressing the mutant channel or from the stationary photocurrent densities of the same number of individual NG108-15 cells expressing RICCR1 set forth in SEQ ID NO: 5, respectively.

Said calculation follows the generally known formula for calculating a mean, i.e. the mean stationary photocurrent density is the quotient of the sum of the individual stationary photocurrent density values and the number of individual stationary photocurrent density values.

The stationary photocurrent density can be determined by whole-cell patch-clamp measurements with an NG108-15 cell expressing the mutant ion channel or RICCR1 set forth in SEQ ID NO: 5, respectively, wherein:

transient capacitive currents in response to voltage steps are measured to determine the capacitance of the NG108-15 cell, and photocurrents at a membrane potential of −60 mV are measured upon illumination of the NG108-15 cell with a 2 s light pulse of a wavelength of 532 nm at saturating intensity of 23 mW/mm$^2$ to determine the mean stationary current of the last 100 ms of the 2 s light pulse; and wherein the stationary photocurrent density is the quotient of the mean stationary current of the last 100 ms of the 2 s light pulse and the capacitance.

The term 'photocurrent' as used herein refers to the current that is induced by exposing a cell which comprises the ion channel in its plasma membrane to light.

Photocurrents as well as transient capacitive currents in a cell can be measured by the whole-cell patch clamp technique as known in the art, as described, e.g., by Mager et al., [ref. 13].

Devices for whole-cell patch clamp measurements including amplifier and interface (e.g., Axopatch 200B amplifier and DigiData 1322A interface by Axon Instruments, Union City, USA) are well known and commercially available to the skilled person, as are devices for exposing the cells used for these measurements to light (e.g., a fast computer-controlled shutter such as Uniblitz LS6ZM2 by Vincent Associates, Rochester, USA).

The whole-cell patch clamp measurements may be performed using a bath solution of 140 mM NaCl, 2 mM CaCl$_2$, 2 MgCl$_2$, 10 mM HEPES, pH 7.4, and a pipette solution of 110 mM NaCl, 2 mM MgCl$_2$, 10 mM EGTA, 10 mM HEPES, pH 7.4.

Preferably, the method for electrophysiological recordings described in example 1 below is used for measuring photocurrents and transient capacitive currents in a cell in the context of the present disclosure.

The mutant ion channel, or a reference ion channel, as disclosed herein, can be expressed as a fusion protein with a detectable marker polypeptide. For example, such marker polypeptide may be EYFP (*Aequorea victoria* enhanced yellow fluorescent protein), e.g. fused to the C-terminus of the mutant ion channel. Thereby the cell's expression level of the mutant ion channel, or the reference ion channel can be assessed in a simple manner, e.g. by detecting the fluorescence of EYFP.

The terms "illuminating" or "illumination" used herein with respect to a cell or a tissue mean exposing (or exposure of) said cell or said tissue to light. Illumination of a cell comprising a mutant ion channel as disclosed herein in its plasma membrane typically results in the movement of cations through the plasma membrane of the cell in response to the light (i.e., a photocurrent). This may result in the depolarization of a nerve cell membrane and triggering of action potentials.

Preferably, the mutant ion channel shows reduced light-dependent desensitization compared to a reference ion channel which has a Thr at the amino acid position corresponding to T218 in SEQ ID NO:5 and a Ser at the amino acid position corresponding to S220 in SEQ ID NO:5 and otherwise is identical to the mutant ion channel.

In particular, reduced light-dependent desensitization (also termed photocurrent desensitization herein) can be an increased stationary-peak-ratio or in particular an increased mean stationary-peak-ratio.

More specifically, a mutant ion channel showing reduced light-dependent desensitization as described herein may provide a stationary-peak-ratio, or in particular a mean stationary-peak-ratio, that is—with increasing preference—at least 1.5-times, at least 1.7-times, or at least 2.0-times, and, e.g., up to 3.5-times, up to 3.0-times, or up to 2.9-times, higher than the stationary-peak-ratio, or in particular the mean stationary-peak-ratio, provided by a reference ion channel, wherein said reference ion channel has a Thr at the amino acid position corresponding to T218 in SEQ ID NO:5 and a Ser at the amino acid position corresponding to S220 in SEQ ID NO:5 and is otherwise identical to the mutant ion channel.

The mean stationary-peak-ratio can be calculated from the stationary-peak-ratios of—with increasing preference—at least 5, at least 10, at least 15, e.g., 5-100, 10-75 or 15-60 individual NG108-15 cells expressing the mutant ion channel or from the stationary photocurrent densities of the same number of individual NG108-15 cells expressing the reference ion channel, respectively.

Said calculation follows the generally known formula for calculating a mean, i.e. the mean stationary photocurrent density is the quotient of the sum of the individual stationary photocurrent density values and the number of individual stationary photocurrent density values.

The stationary-peak-ratio can be determined by whole-cell patch-clamp measurement of photocurrents in an NG108-15 cell expressing the mutant ion channel or the reference ion channel, respectively, at a membrane potential of −60 mV, wherein the photocurrents are measured upon illumination of the NG108-15 cell with a 2 s light pulse of a wavelength of 532 nm at saturating intensity of 23 mW/mm$^2$ to determine the mean stationary current of the last 100 ms of the 2 s light pulse and the peak current of the 2 s light pulse; and wherein the stationary-peak-ratio is the quotient of the mean stationary current of the last 100 ms of the 2 s light pulse and the peak current of the 2 s light pulse. Preferably, the stationary-peak-ratio is determined as described herein, in particular as described in example 1 below.

The inventors also found that the amino acid substitution at one or both of the positions corresponding to T218 and S220 of SEQ ID NO: 5, which characterizes the mutant ion channel disclosed herein, can increase the density of the photocurrent that is induced by illumination with a light. Accordingly, it is contemplated that less light will be needed to achieve a given density of the photocurrent with a mutant ion channel of the present disclosure than with a reference ion channel that has the same (wild-type) amino acids at the positions corresponding to T218 and S220 of SEQ ID NO: 5 and is otherwise identical with the mutant ion channel.

In particular, the mutant ion channel disclosed herein may provide a stationary photocurrent density, or in particular a mean stationary-peak-ratio, than is—with increasing preference—at least 1.5-times, at least 1.7-times, or at least 2.0-times, and, e.g., up to 5.5-times, up to 5.0-times, or up to 4.5-times, higher than the stationary photocurrent density, or in particular the mean stationary-peak-ratio, provided by a reference ion channel, wherein said reference ion channel has a Thr at the amino acid position corresponding to T218 in SEQ ID NO:5 and a Ser at the amino acid position corresponding to S220 in SEQ ID NO:5 and is otherwise identical to the mutant ion channel.

The mean stationary photocurrent density can be calculated from the stationary photocurrent densities of—with increasing preference—at least 5, at least 10, at least 15, e.g., 5-100, 10-75 or 15-60 individual NG108-15 cells expressing the mutant ion channel or from the stationary photocurrent densities of the same number of individual NG108-15 cells expressing the reference ion channel, respectively.

Said calculation follows the generally known formula for calculating a mean, i.e. the mean stationary photocurrent density is the quotient of the sum of the individual stationary photocurrent density values and the number of individual stationary photocurrent density values.

The stationary photocurrent density can be determined by whole-cell patch-clamp measurements with an NG108-15 cell expressing the mutant ion channel or the reference ion channel, respectively, wherein transient capacitive currents in response to voltage steps are measured to determine the capacitance of the NG108-15 cell, and photocurrents at a membrane potential of −60 mV are measured upon illumination of the NG108-15 cell with a 2 s light pulse of a wavelength of 532 nm at saturating intensity of 23 mW/mm² to determine the mean stationary current of the last 100 ms of the 2 s light pulse; and wherein the stationary photocurrent density is the quotient of the mean stationary current of the last 100 ms of the 2 s light pulse and the capacitance. Preferably, the stationary photocurrent density is determined as described herein, in particular as described in example 1 below. An NG108-15 cell expressing a mutant ion channel or a reference channel which is used in whole-cell patch-clamp measurements as described herein expediently comprises the mutant ion channel or the reference ion channel in its plasma membrane.

The mutant ion channel described herein is characterized by an amino acid substitution at one or both of the positions within the 7-transmembrane-helix motif, more specifically helix 6, of the mutant ion channel, wherein said amino acid positions correspond to positions T218 and S220 of the wild-type ion channel RICCR1 set forth in SEQ ID NO: 5.

Preferably, the amino acid at the position corresponding to position T218 of SEQ ID NO: 5 is thereby selected from Leu, Ile, Val, Met, Cys, Phe, Ala, Gly, Pro and Trp, and most preferably is Leu.

The amino acid at the position corresponding to position S220 of SEQ ID NO: 5 is preferably selected from Ala, Gly, Leu, Val, Ile, Met, Pro, Cys and Trp, and most preferably is Ala.

In addition to the amino acid substitution at one or both of the positions corresponding to positions T218 and S220 of SEQ ID NO: 5, the mutant ion channel may comprise one or more further amino acid substitutions. In particular, said further amino acid substitutions may be selected from those which have been reported by Kishi et al. [ref. 18] to not reduce the activity, in particular the peak photocurrent, of R/CCR1 ("ChRmine"), or reduce said activity only to a minor extent, namely Y260F, R136H, S138 W, Y156F, T119V and Y116F.

Accordingly, the mutant ion channel disclosed herein may comprise one or more of the following further amino acid substitutions:

a Phe at the amino acid position corresponding to Y260 in SEQ ID NO:5, a His at the amino acid position corresponding to R136 in SEQ ID NO:5, a Trp at the amino acid position corresponding to S138 in SEQ ID NO:5, a Phe at the amino acid position corresponding to Y156 in SEQ ID NO:5, a Val at the amino acid position corresponding to T119 in SEQ ID NO:5, a Phe at the amino acid position corresponding to Y116 in SEQ ID NO:5.

In particular embodiments, the amino acid sequence of the 7-transmembrane-helix motif of the mutant ion channel is identical with the full-length sequence of the 7-transmembrane-helix motif of the wild-type ion channel RICCR1 set forth in SEQ ID NO: 9, except for the amino acid substitutions at one or both of the amino acid positions corresponding to positions T218 and S220 of SEQ ID NO: 5, and optionally one or more of the further amino acid substitutions:

a Phe at the amino acid position corresponding to Y260 in SEQ ID NO:5, a His at the amino acid position corresponding to R136 in SEQ ID NO:5, a Trp at the amino acid position corresponding to S138 in SEQ ID NO:5, a Phe at the amino acid position corresponding to Y156 in SEQ ID NO:5, a Val at the amino acid position corresponding to T119 in SEQ ID NO:5, a Phe at the amino acid position corresponding to Y116 in SEQ ID NO:5.

In even more particular embodiments, the mutant ion channel comprises, and preferably consists of, the full-length sequence the wild-type ion channel RICCR1 set forth in SEQ ID NO: 5, except for the amino acid substitutions at one or both of the amino acid positions corresponding to positions T218 and S220 of SEQ ID NO: 5, and optionally one or more of the following additional amino acid substitutions:

a Phe at the amino acid position corresponding to Y260 in SEQ ID NO:5, a His at the amino acid position corresponding to R136 in SEQ ID NO:5, a Trp at the amino acid position corresponding to S138 in SEQ ID NO:5, a Phe at the amino acid position corresponding to Y156 in SEQ ID NO:5, a Val at the amino acid position corresponding to T119 in SEQ ID NO:5, a Phe at the amino acid position corresponding to Y116 in SEQ ID NO:5.

In a particular example of the mutant ion channel, nucleic acid, expression vector, cell, uses, methods and device thereof disclosed herein, the amino acid sequence of the 7-transmembrane-helix motif of the mutant ion channel is identical with the full-length sequence of the 7-transmembrane-helix motif of the T218L mutant of RICCR1 set forth in SEQ ID NO: 10.

In a further particular example of the mutant ion channel, nucleic acid, expression vector, cell, uses, methods and device thereof disclosed herein, the amino acid sequence of the 7-transmembrane-helix motif of the mutant ion channel is identical with the full-length sequence of the 7-transmembrane-helix motif of the S220A mutant of RICCR1 set forth in SEQ ID NO: 11.

In a further particular example of the mutant ion channel, nucleic acid, expression vector, cell, uses, methods and device thereof disclosed herein, the amino acid sequence of the 7-transmembrane-helix motif of the mutant ion channel is identical with the full-length sequence of the 7-transmembrane-helix motif of the T218L/S220A double mutant of RICCR1 set forth in SEQ ID NO: 12.

In a further particular example of the mutant ion channel, nucleic acid, expression vector, cell, uses, methods and device thereof disclosed herein, the mutant ion comprises, and preferably consists of, the full-length sequence the T218L mutant of RICCR1 set forth in SEQ ID NO: 6.

In a further particular example of the mutant ion channel, nucleic acid, expression vector, cell, uses, methods and device thereof disclosed herein, the mutant ion comprises, and preferably consists of, the full-length sequence the S220A mutant of RICCR1 set forth in SEQ ID NO: 7.

In a further particular example of the mutant ion channel, nucleic acid, expression vector, cell, uses, methods and device thereof disclosed herein, the mutant ion comprises, and preferably consists of, the full-length sequence the T218L/S220A double mutant of RICCR1 set forth in SEQ ID NO: 8.

With regard to the amino acids at the positions corresponding to positions T218, S220 of SEQ ID NO: 5, and optionally further with regard to the positions corresponding to positions D115, D126, Y260, R136, S138, Y156, T119 and Y116 of SEQ ID NO: 5, the ion channel disclosed herein may be characterized by the particular combinations of substituted and/or unsubstituted amino acids listed as combinations #1-436 below. In said list, the indicated numbering of the amino acid positions of said substitution corresponds to the numbering of the amino acid positions in SEQ ID NO:5 (RICCR1).

| combination # | |
| --- | --- |
| 1 | T218L; S220 is unsubstituted or substituted by T, Y, Q or N |
| 2 | T218I; S220 is unsubstituted or substituted by T, Y, Q or N |
| 3 | T218V; S220 is unsubstituted or substituted by T, Y, Q or N |
| 4 | T218M; S220 is unsubstituted or substituted by T, Y, Q or N |
| 5 | T218C; S220 is unsubstituted or substituted by T, Y, Q or N |
| 6 | T218F; S220 is unsubstituted or substituted by T, Y, Q or N |
| 7 | T218A; S220 is unsubstituted or substituted by T, Y, Q or N |
| 8 | T218G; S220 is unsubstituted or substituted by T, Y, Q or N |
| 9 | T218P; S220 is unsubstituted or substituted by T, Y, Q or N |
| 10 | T218W; S220 is unsubstituted or substituted by T, Y, Q or N |
| 11 | T218L, S220A |
| 12 | T218I, S220A |
| 13 | T218V, S220A |
| 14 | T218M, S220A |
| 15 | T218C, S220A |
| 16 | T218F, S220A |
| 17 | T218A, S220A |
| 18 | T218G, S220A |
| 19 | T218P, S220A |
| 20 | T218W, S220A |
| 21 | T218L, S220G |
| 22 | T218I, S220G |
| 23 | T218V, S220G |
| 24 | T218M, S220G |
| 25 | T218C, S220G |
| 26 | T218F, S220G |
| 27 | T218A, S220G |
| 28 | T218G, S220G |
| 29 | T218P, S220G |
| 30 | T218W, S220G |
| 31 | T218L, S220L |
| 32 | T218I, S220L |
| 33 | T218V, S220L |
| 34 | T218M, S220L |
| 35 | T218C, S220L |
| 36 | T218F, S220L |
| 37 | T218A, S220L |
| 38 | T218G, S220L |
| 39 | T218P, S220L |
| 40 | T218W, S220L |
| 41 | T218L, S220V |
| 42 | T218I, S220V |
| 43 | T218V, S220V |
| 44 | T218M, S220V |
| 45 | T218C, S220V |
| 46 | T218F, S220V |
| 47 | T218A, S220V |
| 48 | T218G, S220V |
| 49 | T218P, S220V |
| 50 | T218W, S220V |
| 51 | T218L, S220I |
| 52 | T218I, S220I |
| 53 | T218V, S220I |
| 54 | T218M, S220I |
| 55 | T218C, S220I |

-continued

| combination # | |
|---|---|
| 56 | T218F, S220I |
| 57 | T218A, S220I |
| 58 | T218G, S220I |
| 59 | T218P, S220I |
| 60 | T218W, S220I |
| 61 | T218L, S220M |
| 62 | T218I, S220M |
| 63 | T218V, S220M |
| 64 | T218M, S220M |
| 65 | T218C, S220M |
| 66 | T218F, S220M |
| 67 | T218A, S220M |
| 68 | T218G, S220M |
| 69 | T218P, S220M |
| 70 | T218W, S220M |
| 71 | T218L, S220P |
| 72 | T218I, S220P |
| 73 | T218V, S220P |
| 74 | T218M, S220P |
| 75 | T218C, S220P |
| 76 | T218F, S220P |
| 77 | T218A, S220P |
| 78 | T218G, S220P |
| 79 | T218P, S220P |
| 80 | T218W, S220P |
| 81 | T218L, S220C |
| 82 | T218I, S220C |
| 83 | T218V, S220C |
| 84 | T218M, S220C |
| 85 | T218C, S220C |
| 86 | T218F, S220C |
| 87 | T218A, S220C |
| 88 | T218G, S220C |
| 89 | T218P, S220C |
| 90 | T218W, S220C |
| 91 | T218L, S220W |
| 92 | T218I, S220W |
| 93 | T218V, S220W |
| 94 | T218M, S220W |
| 95 | T218C, S220W |
| 96 | T218F, S220W |
| 97 | T218A, S220W |
| 98 | T218G, S220W |
| 99 | T218P, S220W |
| 100 | T218W, S220W |
| 101 | S220A; T218W is unsubstituted or substituted by S, Y, Q or N |
| 102 | S220G; T218W is unsubstituted or substituted by S, Y, Q or N |
| 103 | S220L; T218W is unsubstituted or substituted by S, Y, Q or N |
| 104 | S220V; T218W is unsubstituted or substituted by S, Y, Q or N |
| 105 | S220I; T218W is unsubstituted or substituted by S, Y, Q or N |
| 106 | S220M; T218W is unsubstituted or substituted by S, Y, Q or N |
| 107 | S220P; T218W is unsubstituted or substituted by S, Y, Q or N |
| 108 | S220C; T218W is unsubstituted or substituted by S, Y, Q or N |
| 109 | S220W, T218W is unsubstituted or substituted by S, Y, Q or N |
| 110 | T218L; S220 is unsubstituted or substituted by T, Y, Q or N; D115 and T119 and D126 are unsubstituted |
| 111 | T218I; S220 is unsubstituted or substituted by T, Y, Q or N; D115 and T119 and D126 are unsubstituted |
| 112 | T218V; S220 is unsubstituted or substituted by T, Y, Q or N; D115 and T119 and D126 are unsubstituted |
| 113 | T218M; S220 is unsubstituted or substituted by T, Y, Q or N; D115 and T119 and D126 are unsubstituted |
| 114 | T218C; S220 is unsubstituted or substituted by T, Y, Q or N; D115 and T119 and D126 are unsubstituted |
| 115 | T218F; S220 is unsubstituted or substituted by T, Y, Q or N; D115 and T119 and D126 are unsubstituted |
| 116 | T218A; S220 is unsubstituted or substituted by T, Y, Q or N; D115 and T119 and D126 are unsubstituted |
| 117 | T218G; S220 is unsubstituted or substituted by T, Y, Q or N; D115 and T119 and D126 are unsubstituted |
| 118 | T218P; S220 is unsubstituted or substituted by T, Y, Q or N; D115 and T119 and D126 are unsubstituted |
| 119 | T218W; S220 is unsubstituted or substituted by T, Y, Q or N; D115 and T119 and D126 are unsubstituted |
| 120 | T218L, S220A; D115 and T119 and D126 are unsubstituted |
| 121 | T218I, S220A; D115 and T119 and D126 are unsubstituted |
| 122 | T218V, S220A; D115 and T119 and D126 are unsubstituted |

-continued

| combination # | |
|---|---|
| 123 | T218M, S220A; D115 and T119 and D126 are unsubstituted |
| 124 | T218C, S220A; D115 and T119 and D126 are unsubstituted |
| 125 | T218F, S220A; D115 and T119 and D126 are unsubstituted |
| 126 | T218A, S220A; D115 and T119 and D126 are unsubstituted |
| 127 | T218G, S220A; D115 and T119 and D126 are unsubstituted |
| 128 | T218P, S220A; D115 and T119 and D126 are unsubstituted |
| 129 | T218W, S220A; D115 and T119 and D126 are unsubstituted |
| 130 | T218L, S220G; D115 and T119 and D126 are unsubstituted |
| 131 | T218I, S220G; D115 and T119 and D126 are unsubstituted |
| 132 | T218V, S220G; D115 and T119 and D126 are unsubstituted |
| 133 | T218M, S220G; D115 and T119 and D126 are unsubstituted |
| 134 | T218C, S220G; D115 and T119 and D126 are unsubstituted |
| 135 | T218F, S220G; D115 and T119 and D126 are unsubstituted |
| 136 | T218A, S220G; D115 and T119 and D126 are unsubstituted |
| 137 | T218G, S220G; D115 and T119 and D126 are unsubstituted |
| 138 | T218P, S220G; D115 and T119 and D126 are unsubstituted |
| 139 | T218W, S220G; D115 and T119 and D126 are unsubstituted |
| 140 | T218L, S220L; D115 and T119 and D126 are unsubstituted |
| 141 | T218I, S220L; D115 and T119 and D126 are unsubstituted |
| 142 | T218V, S220L; D115 and T119 and D126 are unsubstituted |
| 143 | T218M, S220L; D115 and T119 and D126 are unsubstituted |
| 144 | T218C, S220L; D115 and T119 and D126 are unsubstituted |
| 145 | T218F, S220L; D115 and T119 and D126 are unsubstituted |
| 146 | T218A, S220L; D115 and T119 and D126 are unsubstituted |
| 147 | T218G, S220L; D115 and T119 and D126 are unsubstituted |
| 148 | T218P, S220L; D115 and T119 and D126 are unsubstituted |
| 149 | T218W, S220L; D115 and T119 and D126 are unsubstituted |
| 150 | T218L, S220V; D115 and T119 and D126 are unsubstituted |
| 151 | T218I, S220V; D115 and T119 and D126 are unsubstituted |
| 152 | T218V, S220V; D115 and T119 and D126 are unsubstituted |
| 153 | T218M, S220V; D115 and T119 and D126 are unsubstituted |
| 154 | T218C, S220V; D115 and T119 and D126 are unsubstituted |
| 155 | T218F, S220V; D115 and T119 and D126 are unsubstituted |
| 156 | T218A, S220V; D115 and T119 and D126 are unsubstituted |
| 157 | T218G, S220V; D115 and T119 and D126 are unsubstituted |
| 158 | T218P, S220V; D115 and T119 and D126 are unsubstituted |
| 159 | T218W, S220V; D115 and T119 and D126 are unsubstituted |
| 160 | T218L, S220I; D115 and T119 and D126 are unsubstituted |
| 161 | T218I, S220I; D115 and T119 and D126 are unsubstituted |
| 162 | T218V, S220I; D115 and T119 and D126 are unsubstituted |
| 163 | T218M, S220I; D115 and T119 and D126 are unsubstituted |
| 164 | T218C, S220I; D115 and T119 and D126 are unsubstituted |
| 165 | T218F, S220I; D115 and T119 and D126 are unsubstituted |
| 166 | T218A, S220I; D115 and T119 and D126 are unsubstituted |
| 167 | T218G, S220I; D115 and T119 and D126 are unsubstituted |
| 168 | T218P, S220I; D115 and T119 and D126 are unsubstituted |
| 169 | T218W, S220I; D115 and T119 and D126 are unsubstituted |
| 170 | T218L, S220M; D115 and T119 and D126 are unsubstituted |
| 171 | T218I, S220M; D115 and T119 and D126 are unsubstituted |
| 172 | T218V, S220M; D115 and T119 and D126 are unsubstituted |
| 173 | T218M, S220M; D115 and T119 and D126 are unsubstituted |
| 174 | T218C, S220M; D115 and T119 and D126 are unsubstituted |
| 175 | T218F, S220M; D115 and T119 and D126 are unsubstituted |
| 176 | T218A, S220M; D115 and T119 and D126 are unsubstituted |
| 177 | T218G, S220M; D115 and T119 and D126 are unsubstituted |
| 178 | T218P, S220M; D115 and T119 and D126 are unsubstituted |
| 179 | T218W, S220M; D115 and T119 and D126 are unsubstituted |
| 180 | T218L, S220P; D115 and T119 and D126 are unsubstituted |
| 181 | T218I, S220P; D115 and T119 and D126 are unsubstituted |
| 182 | T218V, S220P; D115 and T119 and D126 are unsubstituted |
| 183 | T218M, S220P; D115 and T119 and D126 are unsubstituted |
| 184 | T218C, S220P; D115 and T119 and D126 are unsubstituted |
| 185 | T218F, S220P; D115 and T119 and D126 are unsubstituted |
| 186 | T218A, S220P; D115 and T119 and D126 are unsubstituted |
| 187 | T218G, S220P; D115 and T119 and D126 are unsubstituted |
| 188 | T218P, S220P; D115 and T119 and D126 are unsubstituted |
| 189 | T218W, S220P; D115 and T119 and D126 are unsubstituted |
| 190 | T218L, S220C; D115 and T119 and D126 are unsubstituted |
| 191 | T218I, S220C; D115 and T119 and D126 are unsubstituted |
| 192 | T218V, S220C; D115 and T119 and D126 are unsubstituted |
| 193 | T218M, S220C; D115 and T119 and D126 are unsubstituted |
| 194 | T218C, S220C; D115 and T119 and D126 are unsubstituted |
| 195 | T218F, S220C; D115 and T119 and D126 are unsubstituted |
| 196 | T218A, S220C; D115 and T119 and D126 are unsubstituted |
| 197 | T218G, S220C; D115 and T119 and D126 are unsubstituted |
| 198 | T218P, S220C; D115 and T119 and D126 are unsubstituted |
| 199 | T218W, S220C; D115 and T119 and D126 are unsubstituted |

-continued

| combination # | |
|---|---|
| 200 | T218L, S220W; D115 and T119 and D126 are unsubstituted |
| 201 | T218I, S220W; D115 and T119 and D126 are unsubstituted |
| 202 | T218V, S220W; D115 and T119 and D126 are unsubstituted |
| 203 | T218M, S220W; D115 and T119 and D126 are unsubstituted |
| 204 | T218C, S220W; D115 and T119 and D126 are unsubstituted |
| 205 | T218F, S220W; D115 and T119 and D126 are unsubstituted |
| 206 | T218A, S220W; D115 and T119 and D126 are unsubstituted |
| 207 | T218G, S220W; D115 and T119 and D126 are unsubstituted |
| 208 | T218P, S220W; D115 and T119 and D126 are unsubstituted |
| 209 | T218W, S220W; D115 and T119 and D126 are unsubstituted |
| 210 | S220A; T218W is unsubstituted or substituted by S, Y, Q or N; D115 and T119 and D126 are unsubstituted |
| 211 | S220G; T218W is unsubstituted or substituted by S, Y, Q or N; D115 and T119 and D126 are unsubstituted |
| 212 | S220L; T218W is unsubstituted or substituted by S, Y, Q or N; D115 and T119 and D126 are unsubstituted |
| 213 | S220V; T218W is unsubstituted or substituted by S, Y, Q or N; D115 and T119 and D126 are unsubstituted |
| 214 | S220I; T218W is unsubstituted or substituted by S, Y, Q or N; D115 and T119 and D126 are unsubstituted |
| 215 | S220M; T218W is unsubstituted or substituted by S, Y, Q or N; D115 and T119 and D126 are unsubstituted |
| 216 | S220P; T218W is unsubstituted or substituted by S, Y, Q or N; D115 and T119 and D126 are unsubstituted |
| 217 | S220C; T218W is unsubstituted or substituted by S, Y, Q or N; D115 and T119 and D126 are unsubstituted |
| 218 | S220W, T218W is unsubstituted or substituted by S, Y, Q or N; D115 and T119 and D126 are unsubstituted |
| 219 | T218L; S220 is unsubstituted or substituted by T, Y, Q or N; D115 and D126 are unsubstituted; T119V |
| 220 | T218I; S220 is unsubstituted or substituted by T, Y, Q or N; D115 and D126 are unsubstituted; T119V |
| 221 | T218V; S220 is unsubstituted or substituted by T, Y, Q or N; D115 and D126 are unsubstituted; T119V |
| 222 | T218M; S220 is unsubstituted or substituted by T, Y, Q or N; D115 and D126 are unsubstituted; T119V |
| 223 | T218C; S220 is unsubstituted or substituted by T, Y, Q or N; D115 and D126 are unsubstituted; T119V |
| 224 | T218F; S220 is unsubstituted or substituted by T, Y, Q or N; D115 and D126 are unsubstituted; T119V |
| 225 | T218A; S220 is unsubstituted or substituted by T, Y, Q or N; D115 and D126 are unsubstituted; T119V |
| 226 | T218G; S220 is unsubstituted or substituted by T, Y, Q or N; D115 and D126 are unsubstituted; T119V |
| 227 | T218P; S220 is unsubstituted or substituted by T, Y, Q or N; D115 and D126 are unsubstituted; T119V |
| 228 | T218W; S220 is unsubstituted or substituted by T, Y, Q or N; D115 and D126 are unsubstituted; T119V |
| 229 | T218L, S220A; D115 and D126 are unsubstituted; T119V |
| 230 | T218I, S220A; D115 and D126 are unsubstituted; T119V |
| 231 | T218V, S220A; D115 and D126 are unsubstituted; T119V |
| 232 | T218M, S220A; D115 and D126 are unsubstituted; T119V |
| 233 | T218C, S220A; D115 and D126 are unsubstituted; T119V |
| 234 | T218F, S220A; D115 and D126 are unsubstituted; T119V |
| 235 | T218A, S220A; D115 and D126 are unsubstituted; T119V |
| 236 | T218G, S220A; D115 and D126 are unsubstituted; T119V |
| 237 | T218P, S220A; D115 and D126 are unsubstituted; T119V |
| 238 | T218W, S220A; D115 and D126 are unsubstituted; T119V |
| 239 | T218L, S220G; D115 and D126 are unsubstituted; T119V |
| 240 | T218I, S220G; D115 and D126 are unsubstituted; T119V |
| 241 | T218V, S220G; D115 and D126 are unsubstituted; T119V |
| 242 | T218M, S220G; D115 and D126 are unsubstituted; T119V |
| 243 | T218C, S220G; D115 and D126 are unsubstituted; T119V |
| 244 | T218F, S220G; D115 and D126 are unsubstituted; T119V |
| 245 | T218A, S220G; D115 and D126 are unsubstituted; T119V |
| 246 | T218G, S220G; D115 and D126 are unsubstituted; T119V |
| 247 | T218P, S220G; D115 and D126 are unsubstituted; T119V |
| 248 | T218W, S220G; D115 and D126 are unsubstituted; T119V |
| 249 | T218L, S220L; D115 and D126 are unsubstituted; T119V |
| 250 | T218I, S220L; D115 and D126 are unsubstituted; T119V |
| 251 | T218V, S220L; D115 and D126 are unsubstituted; T119V |
| 252 | T218M, S220L; D115 and D126 are unsubstituted; T119V |
| 253 | T218C, S220L; D115 and D126 are unsubstituted; T119V |
| 254 | T218F, S220L; D115 and D126 are unsubstituted; T119V |
| 255 | T218A, S220L; D115 and D126 are unsubstituted; T119V |
| 256 | T218G, S220L; D115 and D126 are unsubstituted; T119V |
| 257 | T218P, S220L; D115 and D126 are unsubstituted; T119V |

-continued

| combination # | |
|---|---|
| 258 | T218W, S220L; D115 and D126 are unsubstituted; T119V |
| 259 | T218L, S220V; D115 and D126 are unsubstituted; T119V |
| 260 | T218I, S220V; D115 and D126 are unsubstituted; T119V |
| 261 | T218V, S220V; D115 and D126 are unsubstituted; T119V |
| 262 | T218M, S220V; D115 and D126 are unsubstituted; T119V |
| 263 | T218C, S220V; D115 and D126 are unsubstituted; T119V |
| 264 | T218F, S220V; D115 and D126 are unsubstituted; T119V |
| 265 | T218A, S220V; D115 and D126 are unsubstituted; T119V |
| 266 | T218G, S220V; D115 and D126 are unsubstituted; T119V |
| 267 | T218P, S220V; D115 and D126 are unsubstituted; T119V |
| 268 | T218W, S220V; D115 and D126 are unsubstituted; T119V |
| 269 | T218L, S220I; D115 and D126 are unsubstituted; T119V |
| 270 | T218I, S220I; D115 and D126 are unsubstituted; T119V |
| 271 | T218V, S220I; D115 and D126 are unsubstituted; T119V |
| 272 | T218M, S220I; D115 and D126 are unsubstituted; T119V |
| 273 | T218C, S220I; D115 and D126 are unsubstituted; T119V |
| 274 | T218F, S220I; D115 and D126 are unsubstituted; T119V |
| 275 | T218A, S220I; D115 and D126 are unsubstituted; T119V |
| 276 | T218G, S220I; D115 and D126 are unsubstituted; T119V |
| 277 | T218P, S220I; D115 and D126 are unsubstituted; T119V |
| 278 | T218W, S220I; D115 and D126 are unsubstituted; T119V |
| 279 | T218L, S220M; D115 and D126 are unsubstituted; T119V |
| 280 | T218I, S220M; D115 and D126 are unsubstituted; T119V |
| 281 | T218V, S220M; D115 and D126 are unsubstituted; T119V |
| 282 | T218M, S220M; D115 and D126 are unsubstituted; T119V |
| 283 | T218C, S220M; D115 and D126 are unsubstituted; T119V |
| 284 | T218F, S220M; D115 and D126 are unsubstituted; T119V |
| 285 | T218A, S220M; D115 and D126 are unsubstituted; T119V |
| 286 | T218G, S220M; D115 and D126 are unsubstituted; T119V |
| 287 | T218P, S220M; D115 and D126 are unsubstituted; T119V |
| 288 | T218W, S220M; D115 and D126 are unsubstituted; T119V |
| 289 | T218L, S220P; D115 and D126 are unsubstituted; T119V |
| 290 | T218I, S220P; D115 and D126 are unsubstituted; T119V |
| 291 | T218V, S220P; D115 and D126 are unsubstituted; T119V |
| 292 | T218M, S220P; D115 and D126 are unsubstituted; T119V |
| 293 | T218C, S220P; D115 and D126 are unsubstituted; T119V |
| 294 | T218F, S220P; D115 and D126 are unsubstituted; T119V |
| 295 | T218A, S220P; D115 and D126 are unsubstituted; T119V |
| 296 | T218G, S220P; D115 and D126 are unsubstituted; T119V |
| 297 | T218P, S220P; D115 and D126 are unsubstituted; T119V |
| 298 | T218W, S220P; D115 and D126 are unsubstituted; T119V |
| 299 | T218L, S220C; D115 and D126 are unsubstituted; T119V |
| 300 | T218I, S220C; D115 and D126 are unsubstituted; T119V |
| 301 | T218V, S220C; D115 and D126 are unsubstituted; T119V |
| 302 | T218M, S220C; D115 and D126 are unsubstituted; T119V |
| 303 | T218C, S220C; D115 and D126 are unsubstituted; T119V |
| 304 | T218F, S220C; D115 and D126 are unsubstituted; T119V |
| 305 | T218A, S220C; D115 and D126 are unsubstituted; T119V |
| 306 | T218G, S220C; D115 and D126 are unsubstituted; T119V |
| 307 | T218P, S220C; D115 and D126 are unsubstituted; T119V |
| 308 | T218W, S220C; D115 and D126 are unsubstituted; T119V |
| 309 | T218L, S220W; D115 and D126 are unsubstituted; T119V |
| 310 | T218I, S220W; D115 and D126 are unsubstituted; T119V |
| 311 | T218V, S220W; D115 and D126 are unsubstituted; T119V |
| 312 | T218M, S220W; D115 and D126 are unsubstituted; T119V |
| 313 | T218C, S220W; D115 and D126 are unsubstituted; T119V |
| 314 | T218F, S220W; D115 and D126 are unsubstituted; T119V |
| 315 | T218A, S220W; D115 and D126 are unsubstituted; T119V |
| 316 | T218G, S220W; D115 and D126 are unsubstituted; T119V |
| 317 | T218P, S220W; D115 and D126 are unsubstituted; T119V |
| 318 | T218W, S220W; D115 and D126 are unsubstituted; T119V |
| 319 | S220A; T218W is unsubstituted or substituted by S, Y, Q or N; D115 and D126 are unsubstituted; T119V |
| 320 | S220G; T218W is unsubstituted or substituted by S, Y, Q or N; D115 and D126 are unsubstituted; T119V |
| 321 | S220L; T218W is unsubstituted or substituted by S, Y, Q or N; D115 and D126 are unsubstituted; T119V |
| 322 | S220V; T218W is unsubstituted or substituted by S, Y, Q or N; D115 and D126 are unsubstituted; T119V |
| 323 | S220I; T218W is unsubstituted or substituted by S, Y, Q or N; D115 and D126 are unsubstituted; T119V |
| 324 | S220M; T218W is unsubstituted or substituted by S, Y, Q or N; D115 and D126 are unsubstituted; T119V |
| 325 | S220P; T218W is unsubstituted or substituted by S, Y, Q or N; D115 and D126 are unsubstituted; T119V |
| 326 | S220C; T218W is unsubstituted or substituted by S, Y, Q or N; D115 and D126 are unsubstituted; T119V |

-continued

| combination # | |
| --- | --- |
| 327 | S220W, T218W is unsubstituted or substituted by S, Y, Q or N; D115 and D126 are unsubstituted; T119V |

Combinations #328-#436 correspond to combinations #1-#327, except for additionally comprising one or more of amino acid substitutions Y116F, R136H, S138W, Y156F and Y260F (positions corresponding to SEQ ID NO: 5).

Preferably, the mutant ion channel comprises the following amino acid sequence motif set forth in SEQ ID NO: 13 within its 7-transmembrane-helix motif Ala-Glu-His-Ser-Leu-His-Val-Leu-Lys-Phe-Ala-Val-
  Phe-Xaa1-Phe-Xaa2-Met-Leu-Trp-Ile-Leu-Phe-Pro-
  Leu-Val-Trp-Ala-Ile wherein:

(a) Xaa1 is selected from Leu, Ile, Val, Met, Cys, Phe, Ala, Gly, Pro and Trp, and preferably is Leu, and Xaa2 is selected from Ala, Gly, Leu, Val, Ile, Met, Pro, Cys and Trp, and preferably is Ala; or (b) Xaa1 is selected from Leu, Ile, Val, Met, Cys, Phe, Ala, Gly, Pro and Trp, and preferably is Leu, and Xaa2 is selected from Ser, Thr, Tyr, Gln and Asn, and preferably is Ser; or (c) Xaa1 is selected from Thr, Ser, Tyr, Gln and Asn, and preferably is Thr, and Xaa2 is selected from Ala, Gly, Leu, Val, Ile, Met, Pro, Cys and Trp, and preferably is Ala.

The amino acid residues aspartate 85 (D85), threonine 89 (T89) und aspartate 96 (D96) which are considered to be relevant for the vectorial proton transport in the light-driven proton pump bacteriorhodopsin. The amino acid residues at homologous positions in R/CCR1 are D115, T119 and D126. Without wishing to be bound by any theory, the inventors contemplate that maintaining these amino acids, or replacing one or more of them only by a conservative substitution, may be advantageous.

The mutant ion channel disclosed herein therefore preferably has an Asp at the amino acid position corresponding to D115 in SEQ ID NO:5, a Thr or Val at the amino acid position corresponding to T119 in SEQ ID NO:5, and an Asp at the amino acid position corresponding to D126 in SEQ ID NO:5. Most preferably, the mutant ion channel disclosed herein has an Asp at the amino acid position corresponding to D115 in SEQ ID NO:5, a Thr at the amino acid position corresponding to T119 in SEQ ID NO:5, and an Asp at the amino acid position corresponding to D126 in SEQ ID NO:5.

The mutant ion channel of the present disclosure comprises 7 transmembrane helices, i.e. a 7-transmembrane-helix motif. The mutant ion channel may additionally comprise C- and/or N-terminal sequences. When present in a membrane (e.g., the plasma membrane of a cell) or a liposome, said optional C-terminal sequence of the mutant ion channel can extend into the inside of the lumen enclosed by the membrane (e.g. the cytoplasm of the cell) or the inside of the liposome. Alternatively, said optional C-terminal sequence can be located at the outer surface of the membrane (e.g., the outer surface of the cell) or the outer surface of the liposome. The same applies for the optionally present N-terminal sequence, which is typically located opposite to the optional C-terminal sequences, i.e. N-terminal sequence inside if C-terminal sequence is at the outer surface, and vice versa. The length of the C- and/or N-terminal sequences is not particularly restricted; however, the length of the optional C-terminal sequence (which is not embedded in the membrane) is preferably 1 to 1000 amino acids, more preferably 1 to 500 amino acids, especially preferably 5 to 50 amino acids. Independently of the length of the C-terminal sequence, the length of the optional N-terminal sequence (which is not embedded in the membrane) is preferably 1 to 500 amino acids, more preferably 5 to 50 amino acids. The concept of transmembrane helices of proteins is well known to the skilled person. Generally, a transmembrane helix is an α-helical protein structure, which typically comprises 20 to 25 amino acids.

In addition to the specific amino acid residues specified herein, the mutant ion channel, or in particular its 7-transmembrane-helix motif, may comprises further (semi-)conservative substitutions as compared to the wild-type ion channel RICCR1 set forth in SEQ ID NO: 5, or the 7-transmembrane-helix motif thereof set forth in SEQ ID NO: 9, respectively. Conservative substitutions are those that take place within a family of amino acids that are related in their side chains and chemical properties. Examples of such families are amino acids with basic side chains, with acidic side chains, with non-polar aliphatic side chains, with non-polar aromatic side chains, with uncharged polar side chains, with small side chains, with large side chains etc. Typical semi-conservative and conservative substitutions are listed below.

| Amino acid | Conservative substitution | Semi-conservative substitution |
| --- | --- | --- |
| A | G; S; T | N; V; C |
| C | A; V; L | M; I; F; G |
| D | E; N; Q | A; S; T; K; R; H |
| E | D; Q; N | A; S; T; K; R; H |
| F | W; Y; L; M; H | I; V; A |
| G | A | S; N; T; D; E; N; Q |
| H | Y; F; K; R | L; M; A |
| I | V; L; M; A | F; Y; W; G |
| K | R; H | D; E; N; Q; S; T; A |
| L | M; I; V; A | F; Y; W; H; C |
| M | L; I; V; A | F; Y; W; C; |
| N | Q | D; E; S; T; A; G; K; R |
| P | V; I | L; A; M; W; Y; S; T; C; F |
| Q | N | D; E; A; S; T; L; M; K; R |
| R | K; H | N; Q; S; T; D; E; A |
| S | A; T; G; N | D; E; R; K |
| T | A; S; G; N; V | D; E; R; K; I |
| V | A; L; I | M; T; C; N |
| W | F; Y; H | L; M; I; V; C |
| Y | F; W; H | L; M; I; V; C |

Furthermore, the skilled person will appreciate that glycines at sterically demanding positions should not be substituted and that proline should not be introduced into parts of the protein which have an alpha-helical or a beta-sheet structure, unless specified otherwise herein.

Typically, the cell comprising the mutant ion channel or the reference ion channel (e.g., the wild-type ion channel RICCR1) described herein produces the retinal or retinal derivative necessary for the functioning of said ion channels. Depending on its conformation, the retinal may be all-trans retinal, 11-cis-retinal, 13-cis-retinal, or 9-cis-retinal. It is also contemplated that the mutant ion channel described herein may be incorporated into vesicles, liposomes or other artificial cell membranes.

Accordingly, also disclosed is a channelrhodopsin, comprising the mutant ion channel of the present disclosure, and a retinal or retinal derivative. Preferably, the retinal derivative is selected from the group consisting of 3,4-dehydroretinal, 13-ethylretinal, 9-dm-retinal, 3-hydroxyretinal, 4-hydroxyretinal, naphthylretinal; 3,7,11-trimethyls dodeca-2,4, 6,8, 10-pentaenal; 3,7-dimethyl-deca-2,4,6,8-tetraenal; 3,7-dimethylocta-2,4,6-trienal; and 6-7 rotation-blocked retinals, 8-9 rotation-blocked retinals, and 10-11 rotation-blocked retinals.

In particular embodiments, the ion channel is a green-light absorbing channelrhodopsin, preferably with a maximum of activation at a wavelength in the range of 500-540 nm. In this context, 'activation' in particular means the peak current (maximum photocurrent) which can be determined by whole-cell patch-clamp measurements with an NG108-15 cell comprising the ion channel in its plasma membrane, e.g., using the whole-cell patch-clamp technique described by Mager et al. [ref. 13].

A further aspect of the present disclosure pertains to a nucleic acid comprising a nucleotide sequence coding for the mutant ion channel disclosed herein.

The term 'nucleic acid' as used herein includes DNA and RNA, and preferably means DNA. Accordingly, the term 'nucleotide sequence' as used herein includes DNA and RNA sequences, and preferably means a DNA sequence. The nucleic acid disclosed herein is not naturally occurring, and in particular a nucleic acid construct, e.g., prepared by molecular cloning. Methods for generating nucleic acids (or particularly nucleic acid constructs) comprising a nucleotide sequence coding for a protein of interest have been well known in the art since several decades. A nucleic acid comprising a nucleotide sequence coding for the mutant ion channel disclosed herein can therefore be generated by a person skilled in the art in a routine manner.

The nucleic acid can be modified for optimal expression, for example by adding suitable regulatory sequences and/or targeting sequences and/or by matching of the coding DNA sequence to the preferred codon usage of the chosen host cell (i.e., the cell chosen for expression of the mutant ion channel encoded by the nucleic acid). The targeting sequence may encode a C-terminal extension targeting the mutant ion channel to a particular site or compartment within the cell, such as to the synapse or to a post-synaptic site, to the axon-hillock, or the endoplasmic reticulum. The nucleic acid may be combined with further elements, e.g., a promoter and a transcription start and stop signal and a translation start and stop signal and a polyadenylation signal in order to provide for expression of the sequence of the mutant ion channel of the present disclosure. The promoter can be inducible or constitutive, general or cell specific promoter. An example of a cell-specific promoter is the mGlu6-promotor specific for bipolar cells. Selection of promoters, vectors and other elements is a matter of routine design within the level of ordinary skill in the art. Many such elements are described in the literature and are available through commercial suppliers.

Also disclosed herein is an expression vector which comprises a nucleotide sequence coding for the mutant ion channel disclosed herein, or which comprises the nucleic acid disclosed herein.

For example, the vector is a vector suitable for gene therapy, in particular for virus-mediated gene transfer. In a vector suitable for virus-mediated gene transfer, the nucleotide sequence coding for the mutant ion channel disclosed herein can be packed in a virus and thus be delivered to the site or the cells of interest. Examples of viruses suitable in this context for gene therapy are retroviruses, adenoviruses, adeno-associated viruses (AAVs), lentiviruses, pox viruses, alphaviruses, rabies virus, semliki forest virus and herpes viruses. These viruses differ in how well they transfer genes to the cells they recognize and are able to infect, and whether they alter the cell's DNA permanently or temporarily. However, gene therapy also encompasses non-viral methods, such as application of naked DNA, lipoplexes and polyplexes, and dendrimers. Such types of gene transfer and such types of vectors are commonly known in the art.

The nucleic acid or the expression vector disclosed herein, or at least the nucleotide sequence thereof encoding the mutant ion channel, may be introduced into cells, for example using a virus as a carrier or by transfection. Useful methods for transfection are commonly known in the art and include, e.g., transfection using chemical transfectants (such as, e.g., Lipofectamine or Fugene), electroporation, calcium phosphate co-precipitation and direct diffusion of DNA. A method for transfecting a cell is detailed in example 1 and may be adapted to the respective recipient cell. Transfection with DNA yields stable cells or cell lines, if the transfected DNA is integrated into the genome, or unstable (transient) cells or cell lines, wherein the transfected DNA exists in an extrachromosomal form. Furthermore, stable cell lines can be obtained by using episomal replicating plasmids, which means that the inheritance of the extrachromosomal plasmid is controlled by control elements that are integrated into the cell genome. In general, the selection of a suitable vector or plasmid depends on the intended host cell.

The present disclosure also pertains to a cell comprising the nucleic acid or the expression vector encoding the mutant ion channel, as disclosed herein. The cell typically expresses the mutant ion channel encoded by said nucleic acid or the expression vector such that it comprises the mutant ion channel encoded by said nucleic acid or expression vector in its plasma membrane.

The incorporation of the mutant ion channel into the membrane of cells which do not express the corresponding channel in nature can, for example, simply be effected in that, using commonly known procedures of recombinant DNA technology. The resulting cell comprising the mutant ion channel, or the nucleic acid or the expression vector encoding same, as disclosed herein, is a transgenic cell, specifically is transgenic for the mutant ion channel, and the mutant ion channel is recombinantly expressed in said cell. Typically, the DNA coding for this ion channel is incorporated into a suitable expression vector, e.g. a plasmid, a cosmid or a virus; then the target cells (host cells) are transformed with this vector (here: an expression vector as disclosed herein), and the protein (here: the mutant ion channel) is expressed in this host. Next, the cells are treated in a suitable manner, e.g. with retinal, in order to enable the linkage of a Schiffs base between protein and retinal.

The cell disclosed herein may be an ex vivo cell, i.e. not present in a living individual. For example, such cell is present in a biological sample, e.g., sample that has been obtained from a human or non-human animal.

The term 'animals', as used herein, also includes humans. Accordingly, animals as recited herein can be distinguished between human and non-human animals. Mammals, including humans, are thereby preferred.

The cell disclosed herein may be an individual (e.g., isolated or separate) cell or may be present in a tissue, e.g., in a tissue sample that has been obtained from a human or non-human animal.

Preferably, the cell disclosed herein is a somatic cell. It is also preferred that the cells is an animal cell that is not the cell of an embryo, in particular not a cell of a human embryo. The term 'cell of an embryo' in particular refers to cells obtained from an embryo with the exception of cells of established embryonic cells lines such as, e.g., cells HEK cell lines such as HEK293 cells.

The expression of the mutant ion channel disclosed herein can be advantageously effected in mammalian cell systems. Thus, the cell disclosed herein is preferably a mammalian cell. For example, said mammalian cell can be selected from neuroblastoma cells (e.g., NG108-15 cells), melanoma cells (e.g., the BLM cell line), COS cells (generated by infection of "African green monkey kidney CV1" cells) or HEK cells ("human embryonic kidney cells", e.g. HEK293 cells), and BHK-cells ("baby hamster kidney cells"). In this case, expression is preferably effected by episomal vectors as transient expression. Alternatively, said mammalian cell can be selected from CHO cells ("Chinese hamster ovary cells"), myeloma cells, and MDCK cells ("Madine-Darby canine kidney cells"). In this case, the nucleotide sequence encoding the mutant ion channel is preferably stably integrated into the genome of the cell (stable expression). In other preferred cases, the mammalian cell is an electrically excitable cell, for example selected from a hippocampal cell, a photoreceptor cell, a retinal rod cell, a retinal cone cell, a retinal ganglion cell, a bipolar neuron, a ganglion cell, a pseudounipolar neuron, a multipolar neuron, a pyramidal neuron, a Purkinje cell, and a granule cell.

A neuron is an electrically excitable cell that processes and transmits information by electrical and chemical signaling, wherein chemical signaling occurs via synapses, specialized connections with other cells. A number of specialized types of neurons exist such as sensory neurons responding to touch, sound, light and numerous other stimuli affecting cells of the sensory organs, motor neurons receiving signals from the brain and spinal cord and causing muscle contractions and affecting glands, and interneurons connecting neurons to other neurons within the same region of the brain or spinal cord. Neurons can be neurons of the auditory pathway of a human or non-human animal; such neurons include, e.g., sensory neurons responding to sound. Neurons can be neurons of the optic pathway of a human or non-human animal; such neurons include, e.g., sensory neurons responding to light. Generally, a neuron possesses a soma, dendrites, and an axon. Dendrites are filaments that arise from the cell body, often extending for hundreds of microns and branching multiple times. An axon is a special cellular filament that arises from the cell body at a site called the axon hillock. The cell body of a neuron frequently gives rise to multiple dendrites, but never to more than one axon, although the axon may branch hundreds of times before it terminates. At the majority of synapses, signals are sent from the axon of one neuron to a dendrite of another. There are, however, many exceptions to these rules: neurons that lack dendrites, neurons that have no axon, synapses that connect an axon to another axon or a dendrite to another dendrite, etc. Most neurons can further be anatomically characterized as unipolar or pseudounipolar (dendrite and axon emerge from same process), bipolar (axon and single dendrite on opposite ends of the soma), multipolar (having more than two dendrites and may be further classified as (i) Golgi I neurons with long-projecting axonal processes, such as pyramidal cells, Purkinje cells, and anterior horn cells, and (ii) Golgi II: neurons whose axonal process projects locally, e.g., granule cells.

A photoreceptor cell, is a specialized neuron found in the retina that is capable of phototransduction. The two classic photoreceptors are rods and cones, each contributing information used by the visual system. A retinal ganglion cell is a type of neuron located near the inner surface of the retina of the eye. These cells have dendrites and long axons projecting to the protectum (midbrain), the suprachiasmatic nucleus in the hypothalamus, and the lateral geniculate (thalamus). A small percentage contribute little or nothing to vision, but are themselves photosensitive. Their axons form the retinohypothalamic tract and contribute to circadian rhythms and pupillary light reflex, the resizing of the pupil. They receive visual information from photoreceptors via two intermediate neuron types: bipolar cells and amacrine cells. Amacrine cells are interneurons in the retina, and responsible for 70% of input to retinal ganglion cells. Bipolar cells, which are responsible for the other 30% of input to retinal ganglia, are regulated by amacrine cells. As a part of the retina, the bipolar cell exists between photoreceptors (rod cells and cone cells) and ganglion cells. They act, directly or indirectly, to transmit signals from the photoreceptors to the ganglion cells.

The cell of the present disclosure it typically obtained from a cell (parent cell) by introducing a nucleic acid or expression vector encoding a mutant ion channel of the present disclosure are described herein. The cell of the present disclosure as well as the parent cell may be maintained and cultured at an appropriate temperature and gas mixture (typically, 37° C., 5% $CO_2$), optionally in a cell incubator as known to the skilled person and as exemplified for NG108-15 cells in the. Culture conditions may vary for each cell type, and variation of conditions for a particular cell type can result in different phenotypes. Aside from temperature and gas mixture, the most commonly varied factor in cell culture systems is the growth medium. Recipes for growth media can vary in pH, glucose concentration, growth factor and the presence of other nutrient components among others. Growth media are either commercially available, or can be prepared from commercially available ingredients. Compositions for suitable growth media are known in the art, and often obtainable from cell suppliers such as the American Tissue Culture Collection (ATCC). Growth factors used for supplement media are often derived from animal blood such as calf serum. Additionally, antibiotics may be added to the growth media. Amongst the common manipulations carried out on culture cells are media changes and passaging cells.

The mutant ion channel or a cell comprising same as disclosed herein can be used in a high-throughput screenings, in particular in drug discovery. A high-throughput screening (HTS), is a method for scientific experimentation especially used in drug discovery and relevant to the fields of biology and chemistry. HTS allows a researcher to effectively conduct millions of biochemical, genetic or pharmacological tests in a short period of time, often through a combination of modern robotics, data processing and control software, liquid handling devices, and sensitive detectors. By this process, one may rapidly identify active agents which modulate a particular biomolecular pathway; particularly a substance modifying a cellular function that is governed by the voltage potential of the cell.

In essence, HTS uses an approach to collect a large amount of experimental data on the effect of a multitude of substances on a particular target in a relatively short time. A screen, in this context, is the larger experiment, with a single goal (usually testing a scientific hypothesis), to which all this data may subsequently be applied. For HTS cells according to the invention may be seed in a tissue plate, such as a multi well plate, e.g. a 96-well plate. Then the cell in the plate is contacted with the test substance for a time sufficient to interact with the targeted ion channel. The test substance may be different from well to well across the plate. After incubation time has passed, measurements are taken across all the plate's wells, either manually or by a machine and optionally compared to measurements of a cell which has not been contacted with the test substance. Manual measurements may be necessary when the researcher is using patch-clamp, looking for effects not yet implemented in automated routines. Otherwise, a specialized automated analysis machine can run a number of experiments on the wells (such as analysing light of a particular frequency or a high-throughput patch-clamp measurement). In this case, the machine outputs the result of each experiment e.g. as a grid of numeric values, with each number mapping to the value obtained from a single well. Depending upon the results of this first assay, the researcher can perform follow up assays within the same screen by using substances similar to those identified as active (i.e. modifying an intracellular cyclic nucleotide level) into new assay plates, and then re-running the experiment to collect further data, optimize the structure of the chemical agent to improve the effect of the agent on the cell. Automation is an important element in HTS's usefulness. A specialized robot is often responsible for much of the process over the lifetime of a single assay plate, from creation through final analysis. An HTS robot can usually prepare and analyze many plates simultaneously, further speeding the data-collection process. Examples for apparatuses suitable for HTS in accordance with the present invention comprise a Fluorometric Imaging Plate Reader (FLIPR™; Molecular Devices), FLEXstation™ (Molecular Devices), Voltage Ion Probe Reader (VIPR, Aurora Biosciences), Attofluor® Ratio Vision® (ATTO). Various optogenetic approaches to drug discovery, in particular in neuroscience, are generally known in the art; see, e.g., reviews by Zhang et al. and Agus et al. [ref. 23 and 24].

Thus, the presently disclosed mutant ion channel is particularly useful as a research tool, such as in a non-therapeutic use for light-stimulation of electrically excitable cells, in particular neurons. Further guidance, e.g., with regard to hippocampal neuron culture, and electrophysiological recordings from hippocampal neurons, as well as electrophysiological recordings on HEK293 cells, can be found in WO 2012/032103.

Disclosed herein is the use of a mutant ion channel, or a nucleic acid or expression vector encoding same, as disclosed herein, for rendering cells sensitive to stimulation with light. Said use for rendering cells sensitive to stimulation with light is preferably a non-therapeutic use, such as an ex vivo use, e.g. an in vitro use. Further disclosed herein is a method of using a mutant ion channel, or a nucleic acid or expression vector encoding same, for rendering cells sensitive to stimulation with light, wherein the method comprises the step of using the mutant ion channel, the nucleic acid or the expression vector to confer to said cells sensitivity to light. In said use or method, the cells are preferably generated by introducing the mutant ion channel, the nucleic acid or the expression vector into cells (parent cells) which lack the mutant ion channel.

In said use or method for rending cells sensitive to light, the cells comprise the mutant ion channel in their plasma membranes, and the stimulation with light preferably modulates the voltage potential of the cells. Thereby, the wavelength of the light may be in the range of 400-600 nm, in particular 450-570 nm, more particularly 500-540 nm.

"Sensitive to light" according to the present disclosure means that the cell comprises a mutant ion channel that can be activated by said light. In particular, this feature can be the capability of the cell to generate a photocurrent when exposed to said light. Preferably said photocurrent is characterized by a stationary photocurrent density of—with increasing preference—at least 50%, at least 60%, at least 70%, at least 80%, at least 90%, or at least 100%, and, optionally, up to 350%, up to 300%, or up to 290%, of the stationary photocurrent density generated by a cell comprising the wild-type ion channel RICCR1 set forth in SEQ ID NO: 5; or in particular by a mean stationary photocurrent density of—with increasing preference—at least 50%, at least 60%, at least 70%, at least 80%, at least 90%, or at least 100%, and, optionally, up to 350%, up to 300%, or up to 290%, of the mean stationary photocurrent density generated by a cell comprising the wild-type ion channel RI CCR1 set forth in SEQ ID NO: 5. Photocurrents can be measured by the whole-cell patch clamp technique as known in the art, or in particular using a method as described in example 1 herein. The stationary photocurrent density or mean stationary photocurrent density generated by a cell can be determined as described herein in the context of the photocurrent provided by the mutant ion channel.

A further aspect of the present disclosure pertains to a method for modulating the voltage potential of cells in response to stimulation with light, in particular light of wavelength in the range of 400-600 nm, in particular 450-570 nm, more particularly 500-540 nm. Said cells comprise mutant ion channels as disclosed herein in their plasma membranes and are preferably selected from one or more of neurons, myocytes and skeletal muscle cells. Said method comprises exposing the cells to light so as to modulate the voltage potential of the cell.

A modulation of the voltage potential as described herein can be measured by methods known in the art, e.g. using the whole-cell patch clamp technique, and in particular can be measured using the whole-cell patch clamp technique described in example 1 below.

A further aspect of the present disclosure pertains to a method for illuminating a targeted tissue in a human or non-human animal, wherein the targeted tissue comprises cells having the mutant ion channel disclosed herein in their plasma membranes. The method comprises the step of using an implantable light applicator to deliver light to the targeted tissue after implantation in a location adjacent to the targeted tissue. The light applicator comprises a light source and is operatively coupled to a controller, a power supply, and an implantable illuminance sensor such that the controller causes the power supply to let current flow to the light source to cause an emission of photons to the implantable light applicator based at least in part upon an output signal from the implantable illuminance sensor, wherein the implantable illuminance sensor is positioned such that it captures at least a portion of the photons directed toward the targeted tissue by the implantable light applicator. The wavelength of the light delivered by the light source may be in the range of 400-600 nm, in particular 450-570 nm, more particularly 500-540 nm. The method may further comprise the step of using a physiologic sensor to produce an output signal that is correlated with a physiologic response of the targeted tissue to the input of light.

The targeted tissue is typically genetically modified with a nucleic acid sequence encoding the mutant ion channel (e.g., by introducing a nucleic acid or expression vector comprising said sequence, as disclosed herein), such that the tissue comprises cells expressing the mutant ion channel which are the cells having the mutant ion channel disclosed herein in their plasma membranes.

Said method for modulating the voltage potential of cells in response to stimulation with light as well as said method for illuminating a targeted tissue in a human or non-human animal are preferably non-therapeutic methods, such as ex vivo methods, e.g. in vitro methods.

In the use and the method for rending cells sensitive to light as well as in the methods for modulating the voltage potential of cells in response to stimulation with light or for illuminating a targeted tissue in a human or non-human animal described herein, the cells can be cells as describe herein above, preferably animal cells which do not include cells of an embryo. Particularly, the cells can be mammalian cells, preferably somatic cells, e.g., selected from neurons, myocytes and skeletal muscle cells. Specifically, said neurons can be neurons of the optic pathway (e.g., photoreceptor cells) or the auditory pathway of a human or non-human animal.

Where the use or method is a non-therapeutic, ex vivo or in vitro use or method, the cells can be cells in a sample (e.g., a tissue sample) that has been obtained from a human or non-human animal.

A further aspect of the present disclosure pertains to a device comprising: (a) a container comprising the mutant ion channel, or a nucleic acid or expression vector encoding same, as disclosed herein; and (b) a light source, preferably a light source configured to deliver light of a wavelength in the range of 400-600 nm, in particular 450-570 nm, more particularly 500-540 nm. Apart from the mutant ion channel comprised by the container (a) and the preferred wavelength of the light source, the device may be as described in WO 2020/150093.

The container (a) preferably comprises a nucleic acid or expression vector encoding the mutant ion channel, as disclosed herein. The container can be a syringe.

The container is preferably implantable, i.e. configured such that it can be totally or partially implanted within an individual (e.g. a human or non-human animal).

The light source may, e.g., selected from laser light sources and light-emitting diodes (LEDs). The device may further comprise one or more optical fibers configured to transmit light from the light source to a target structure of interest. The optical fibers may comprise plastic or glass materials. Preferably, the optical fibers are suitably flexible to facilitate placement of the light-generating device in locations that could not be accommodated by rigid structures. For example, when implanting the device, the optical fibers can be placed in various locations on or in the patient's body. Light from the light source can pass through the optical fiber, passing around corners and bends in the optical fiber, and emerge at the end of the optical fiber to deliver light to a target structure (particularly a targeted tissue in an individual).

The light source and, if present, the optical fibers can be part of an implantable light applicator configured to deliver light to a targeted tissue after implantation in a location adjacent to the targeted tissue, and the device can further comprise:

(c) a controller;

(d) a power supply; and (e) an implantable illuminance sensor, wherein the controller causes the power supply to let current flow to the light source to cause an emission of photons to the implantable light applicator based at least in part upon an output signal from the implantable illuminance sensor;

wherein the implantable illuminance sensor is configured such that it can be positioned to capture at least a portion of the photons directed toward the targeted tissue by the implantable optical applicator.

The targeted tissue is typically genetically modified with a nucleic acid sequence encoding the mutant ion channel (e.g., by introducing a nucleic acid or expression vector comprising said sequence, as disclosed herein), such that the tissue comprises cells expressing the mutant ion channel which are the cells having the mutant ion channel disclosed herein in their plasma membranes.

The implantable light applicator described herein may be a light-generating device as described in in WO 2020/150093, except for the preferred wavelength of the light source. Likewise, the controller, power supply and implantable illuminance sensor described herein may be as described in WO 2020/150093, and may be set up and function as described in WO 2020/150093.

The implantable light applicator described herein can generally produce light of a variety of different wavelengths from one or more light sources on the device. In some cases, the implantable light applicator may include a light cuff or sleeve that can be placed around or near the targeted tissue. In some cases, a portion of the light source or the entire light source is implantable. The implantable light applicator may be of any useful configuration for stimulating the mutant ion channel disclosed herein. In some cases, for example, an implantable light applicator may comprise components that facilitate exclusive illumination of the targeted tissue. For example, in some cases, a light-generating device may exclusively direct light to the targeted tissue, in particular to at least one cell comprising the mutant ion channel in its plasma membrane or part of such cell, e.g., a particular axon of a nerve cell, or a specific anatomical structure, such as, e.g. a bundle of nerve fibers, or a portion of the spinal cord. By "exclusively direct light" is meant that the light-generating device only delivers light to the specific target structure, and does not illuminate other structures. For example, an implantable light applicator may be configured to illuminate an axon of a nerve cell, but not to illuminate any other portion of the nerve cell. In this way, the light from the light-generating device only affects light-activated proteins in the specific target structure that is illuminated. The implantable light applicator may comprise one or more light sources which are configured to deliver light in one or more 2-dimensional and/or 3-dimensional patterns to one or more target locations, including but not limited to one or more portions (e.g., multiple layers) of the targeted tissue and/or anatomical structure. In certain instances, an implantable light applicator may comprise a plurality of light sources (e.g., a plurality of laser light sources or light-emitting diodes (LEDs)), as well as any suitable number of light guides that are configured to bend or shape light in a desired manner. Examples of light delivery devices are provided in U.S. Pat. No. 8,545,543.

For example, the power supply described herein can be a battery, or can comprise an external antenna for receiving wirelessly transmitted electromagnetic energy from an external source for powering the device. The wirelessly transmitted electromagnetic energy can be a radio wave, a microwave, or any other electromagnetic energy source that can be transmitted from an external source to power the light-generating device.

The controller described herein can be, e.g., a circuit produced using semiconductor or other processes known in the art, said circuit can be an integrated circuit comprised by the implantable light applicator. The controller may be operatively linked to a processor (e.g., a computer).

The targeted tissue is typically genetically modified with a nucleic acid sequence encoding the mutant ion channel (e.g., by introducing a nucleic acid or expression vector comprising said sequence, as disclosed herein), such that the tissue comprises cells expressing the mutant ion channel which are the cells having the mutant ion channel disclosed herein in their plasma membranes.

The implantable illuminance sensor described herein may be selected from a photovoltaic cell, a photodiode, a pyroelectric sensor, a photoresistor, a photoconductor, a phototransistor and a photogalvanic sensor.

The physiologic sensor described herein may be selected from an electromyogram sensor, an electroneurogram sensor, electroencephalogram sensor, an electrocardiogram sensor, a pressure sensor, a temperature sensor, a chemometric sensor, a motion sensor, an accelerometer, a gyro, a strain sensor, an impedance sensor and a capacitance sensor.

The device disclosed herein as well as the herein disclosed method for illuminating a targeted tissue can be used for purposes corresponding to those of the devices and methods for illuminating a target tissue or cell described in WO 2020/150093.

Utilization of the mutant ion channel as disclosed herein for (optogenetic) stimulation of neurons, in particular neurons of the auditory or optic pathway, or myocytes and/or skeletal muscle cells of an individual in need thereof is contemplated.

Specifically, it is contemplated that the mutant ion channel of the present disclosure, as well as the nucleic acid or expression vector encoding same, as described herein, will be useful in medical applications such as, e.g., in the restoration of vision, or in the restoration of hearing with an optical cochlear implant, as already described for a similar type of ion channels (channelrhodopsins, including in particular CatCh, f-Chrimson and ChrimsonR). Such medical applications of light-activated ion channels are known in the art; see, e.g., the review by Kleinlogel et al. [ref. 25]. In such medical applications, the reduction of the light intensity required to provide a certain density of the photocurrent is expected to be beneficial by, e.g., lowering the risk of photoxicity and the energy budget for applications in the restoration of vision and hearing that use repetitive light stimuli to activate the visual or auditory pathway.

One aspect of the present disclosure therefore provides a mutant ion channel, or a nucleic acid or expression vector encoding same, as disclosed herein, for use in a method of treating or ameliorating loss of vision or loss of hearing, in particular a method of restoring, at least partially, loss of vision or loss of hearing (the latter especially with an optical cochlear implant).

Utilization of the mutant ion channel as disclosed herein for (optogenetic) stimulation of neurons, in particular neurons of the auditory or optic pathway, or myocytes and/or skeletal muscle cells of an individual in need thereof is contemplated.

Further described are non-human animals which comprise a mutant ion channel, or a nucleic acid or expression vector encoding same, as disclosed herein. Preferably, such animal functionally expresses the mutant ion channel according to the present disclosure, e.g. in an electrically excitable cell such as a neuron, in particular in spiral ganglion neurons, as also described for the cell of the present disclosure. Likewise, disclosed are non-human animals, which comprise a cell according to the present disclosure, which preferably functionally expresses the mutant ion channel according to the present disclosure.

The non-human animal may be any animal other than a human. In one aspect of the present disclosure, the non-human animal comprising a mutant ion channel, or a nucleic acid or expression vector encoding same, as disclosed herein, is a nonvertebrate, e.g. selected from *Caenorhabditis elegans, Arbacia punctulata, Ciona intestinalis, Drosophila,* e.g. *Drosophila melanogaster, Euprymna scolopes, Hydra, Loigo pealei, Pristionchus pacificus, Strongylocentrotus purpuratus, Symsagittifera roscoffensis,* and *Tribolium castaneum.* In another aspect of the present disclosure, the non-human animal comprising a mutant ion channel, or a nucleic acid or expression vector encoding same, as disclosed herein, is a vertebrate, e.g. a mammal, in particular a rodent, such as a mouse or a rat, or a non-human primate.

Exemplary vertebrate species in this context include guinea pig (*Cavia porcellus*), hamster, mouse (*Mus musculus*), rat (*Rattus norvegicus*), chicken (*Gallus gallus domesticus*), cat (*Felis cattus*), dog (*Canis lupus familiaris*), Lamprey, Japanese ricefish (*Oryzias latpes*), Rhesus macaque, *Sigmodon hispidus*, zebra finch (*Taeniopygia guttata*), pufferfish (*Takifugu rubripres*), african clawed frog (*Xenopus laevis*), and zebrafish (*Danio rerio*). Non-human primates are in particular all species of animals under the order Primates which are not a member of the genus Homo, for example rhesus macaque, chimpanzee, baboon, marmoset, and green monkey.

The non-human animals according to the present invention typically do not include animals (in particular vertrebrates) which are not likely to yield in substantial medical benefit to man or animal and which are therefore not subject to patentability under the respective patent law or jurisdiction. Moreover, the skilled person will take appropriate measures, as e.g. laid down in international guidelines of animal welfare, to ensure that the substantial medical benefit to man or animal will outweigh any animal suffering.

The invention is further described by the following embodiments E1-E82:

E1. A mutant ion channel, wherein the mutant ion channel comprises:

a 7-transmembrane-helix motif having at least 70% amino acid sequence identity to the full-length sequence of the 7-transmembrane-helix motif of the wild-type ion channel RICCR1 set forth in SEQ ID NO: 9, and an amino acid substitution at one or both of the positions within said motif of the mutant ion channel which correspond to positions T218 and S220 of RICCR1 set forth in SEQ ID NO: 5; and wherein the mutant ion channel is capable of being activated by light.

E2. The mutant ion channel of E1, wherein the mutant ion channel further shows reduced light-dependent desensitization compared to a reference ion channel which has a Thr at the amino acid position corresponding to T218 in SEQ ID NO:5 and a Ser at the amino acid position corresponding to S220 in SEQ ID NO:5 and otherwise is identical to the mutant ion channel.

E3. The mutant ion channel of any one of E1-E2, wherein the amino acid sequence of the 7-transmembrane-helix motif of the mutant ion channel has at least 75%, at least 80%, at least 85%, at least 90%, at least 92%, at least 94%, at least 96%, at least 98%, at least 99% identity to the full-length sequence of SEQ ID NO: 9.

E4. The mutant ion channel of any one of E1-E3, wherein the mutant ion channel comprises an amino acid sequence having at least 75%, at least 80%, at least 85%, at least 90%, at least 92%, at least 94%, at least 96%, at least 98%, at least 99% identity to the full-length sequence of SEQ ID NO: 5.

E5. The mutant ion channel of any one of E1-E4, wherein the amino acid at the position corresponding to position T218 of SEQ ID NO: 5 is selected from Leu, Ile, Val, Met, Cys, Phe, Ala, Gly, Pro and Trp, and preferably is Leu.

E6. The mutant ion channel of any one of E1-E5, wherein the amino acid at the position corresponding to position S220 of SEQ ID NO: 5 is selected from Ala, Gly, Leu, Val, Ile, Met, Pro, Cys and Trp, and preferably is Ala.

E7. The mutant ion channel of any one of E1-E6, wherein the mutant ion channel further comprises one or more of the following additional amino acid substitutions:
a Phe at the amino acid position corresponding to Y260 in SEQ ID NO:5,
a His at the amino acid position corresponding to R136 in SEQ ID NO:5,
a Trp at the amino acid position corresponding to S138 in SEQ ID NO:5,
a Phe at the amino acid position corresponding to Y156 in SEQ ID NO:5,
a Val at the amino acid position corresponding to T119 in SEQ ID NO:5,
a Phe at the amino acid position corresponding to Y116 in SEQ ID NO:5.

E8. The mutant ion channel of any one of E1-E7, wherein the amino acid sequence of the 7-transmembrane-helix motif of the mutant ion channel is identical with the full-length sequence of SEQ ID NO: 9, except for the amino acid substitutions at one or both of the amino acid positions corresponding to positions T218 and S220 of SEQ ID NO: 5, and optionally one or more of the following additional amino acid substitutions:
a Phe at the amino acid position corresponding to Y260 in SEQ ID NO:5,
a His at the amino acid position corresponding to R136 in SEQ ID NO:5,
a Trp at the amino acid position corresponding to S138 in SEQ ID NO:5,
a Phe at the amino acid position corresponding to Y156 in SEQ ID NO:5,
a Val at the amino acid position corresponding to T119 in SEQ ID NO:5,
a Phe at the amino acid position corresponding to Y116 in SEQ ID NO:5.

E9. The mutant ion channel of any one of E1-E8, wherein the mutant ion channel comprises, and preferably consists of, the full-length sequence of SEQ ID NO: 5, except for the amino acid substitutions at one or both of the amino acid positions corresponding to positions T218 and S220 of SEQ ID NO: 5, and optionally one or more of the following additional amino acid substitutions:
a Phe at the amino acid position corresponding to Y260 in SEQ ID NO:5,
a His at the amino acid position corresponding to R136 in SEQ ID NO:5,
a Trp at the amino acid position corresponding to S138 in SEQ ID NO:5,
a Phe at the amino acid position corresponding to Y156 in SEQ ID NO:5, a Val at the amino acid position corresponding to T119 in SEQ ID NO:5,
a Phe at the amino acid position corresponding to Y116 in SEQ ID NO:5.

E10. The mutant ion channel of any one of E1-E9, wherein the mutant ion channel comprises the following amino acid sequence motif:

```
                                        (SEQ ID NO: 13)
Ala-Glu-His-Ser-Leu-His-Val-Leu-Lys-Phe-Ala-Val-
Phe-Xaa1-Phe-Xaa2-Met-Leu-Trp-Ile-Leu-Phe-Pro-
Leu-Val-Trp-Ala-Ile
``` wherein:
(a) Xaa1 is selected from Leu, Ile, Val, Met, Cys, Phe, Ala, Gly, Pro and Trp, and preferably is Leu, and
Xaa2 is selected from Ala, Gly, Leu, Val, Ile, Met, Pro, Cys and Trp, and preferably is Ala; or
(b) Xaa1 is selected from Leu, Ile, Val, Met, Cys, Phe, Ala, Gly, Pro and Trp, and preferably is Leu, and
Xaa2 is selected from Ser, Thr, Tyr, Gln and Asn, and preferably is Ser; or
(c) Xaa1 is selected from Thr, Ser, Tyr, Gln and Asn, and preferably is Thr, and
Xaa2 is selected from Ala, Gly, Leu, Val, Ile, Met, Pro, Cys and Trp, and preferably is Ala.

E11. A mutant ion channel, wherein the mutant ion channel comprises a 7-transmembrane-helix motif comprising the following amino acid sequence motif:

```
                                        (SEQ ID NO: 13)
Ala-Glu-His-Ser-Leu-His-Val-Leu-Lys-Phe-Ala-Val-
Phe-Xaa1-Phe-Xaa2-Met-Leu-Trp-Ile-Leu-Phe-Pro-
Leu-Val-Trp-Ala-Ile
``` wherein:
(a) Xaa1 is selected from Leu, Ile, Val, Met, Cys, Phe, Ala, Gly, Pro and Trp, and preferably is Leu, and
Xaa2 is selected from Ala, Gly, Leu, Val, Ile, Met, Pro, Cys and Trp, and preferably is Ala; or
(b) Xaa1 is selected from Leu, Ile, Val, Met, Cys, Phe, Ala, Gly, Pro and Trp, and preferably is Leu, and
Xaa2 is selected from Ser, Thr, Tyr, Gln and Asn, and preferably is Ser; or
(c) Xaa1 is selected from Thr, Ser, Tyr, Gln and Asn, and preferably is Thr, and
Xaa2 is selected from Ala, Gly, Leu, Val, Ile, Met, Pro, Cys and Trp, and preferably is Ala;
wherein the mutant ion channel is capable of being activated by light.

E12. The mutant ion channel of E11, wherein the mutant ion channel further shows reduced light-dependent desensitization compared to a reference ion channel which has a Thr at the amino acid position corresponding to T218 in SEQ ID NO:5 and a Ser at the amino acid position corresponding to S220 in SEQ ID NO:5 and otherwise is identical to the mutant ion channel.

E13. The mutant ion channel of any one of E1-E12, wherein the mutant ion channel is a green light absorbing channelrhodopsin, preferably with a maximum of activation at a wavelength in the range of 500-540 nm.

E14. The mutant ion channel of any one of E1-E13, wherein the mutant ion channel provides an at least 1.5-times, at least 1.7-times, or at least 2.0-times, and, optionally, up to 3.5-times, up to 3.0-times, or up to 2.9-times, higher stationary-peak-ratio than a reference ion channel which has a Thr at the amino acid position corresponding to T218 in SEQ ID NO:5 and a Ser at the amino acid position corresponding to S220 in SEQ ID NO:5 and otherwise is identical to the mutant ion channel;

wherein the stationary-peak-ratio is measurable by whole-cell patch-clamp measurement of photocurrents in an NG108-15 cell expressing the mutant ion channel or the reference ion channel, respectively, at a membrane potential of –60 mV, in said whole-cell patch-clamp measurement, the photocurrents are measured upon illumination of the NG108-15 cell with a 2 s light pulse of a wavelength of 532 nm at saturating intensity of 23 mW/mm² to determine the mean stationary current of the last 100 ms of the 2 s light pulse and the peak current of the 2 s light pulse; and wherein the stationary-peak-ratio is the quotient of the mean stationary current of the last 100 ms of the 2 s light pulse and the peak current of the 2 s light pulse.

E15. The mutant ion channel of any one of E1-E14, wherein the mutant ion channel provides an at least 1.5-times, at least 1.7-times, or at least 2.0-times, and, optionally, up to 3.5-times, up to 3.0-times, or up to 2.9-times, higher mean stationary-peak-ratio than a reference ion channel which has a Thr at the amino acid position corresponding to T218 in SEQ ID NO:5 and a Ser at the amino acid position corresponding to S220 in SEQ ID NO:5 and otherwise is identical to the mutant ion channel;

wherein the mean stationary-peak-ratio is the mean of the stationary-peak-ratios of at least 5, at least 10, at least 15, e.g., 5-100, 10-75 or 15-60 individual NG108-15 cells expressing the mutant ion channel or from the stationary photocurrent densities of the same number of individual NG108-15 cells expressing the reference ion channel, respectively;

wherein the stationary-peak-ratio of an individual NG108-15 cell is measurable by whole-cell patch-clamp measurement of photocurrents in the NG108-15 cell at a membrane potential of –60 mV, in said whole-cell patch-clamp measurement, the photocurrents are measured upon illumination of the NG108-15 cell with a 2 s light pulse of a wavelength of 532 nm at saturating intensity of 23 mW/mm² to determine the mean stationary current of the last 100 ms of the 2 s light pulse and the peak current of the 2 s light pulse; and wherein the stationary-peak-ratio of the NG108-15 cell is the quotient of the mean stationary current of the last 100 ms of the 2 s light pulse and the peak current of the 2 s light pulse.

E16. The mutant ion channel of any one of E1-E15, wherein the mutant ion channel provides an at least 1.5-times, at least 1.7-times, or at least 2.0-times, and, e.g., up to 5.5-times, up to 5.0-times, or up to 4.5-times, higher stationary photocurrent density than a reference ion channel which has a Thr at the amino acid position corresponding to T218 in SEQ ID NO:5 and a Ser at the amino acid position corresponding to S220 in SEQ ID NO:5 and otherwise is identical to the mutant ion channel;

wherein the stationary photocurrent density is measurable by whole-cell patch-clamp measurements with an NG108-15 cell expressing the mutant ion channel or the reference ion channel, respectively;

in said whole-cell patch-clamp measurements:

transient capacitive currents in response to voltage steps are measured to determine the capacitance of the NG108-15 cell, and photocurrents at a membrane potential of –60 mV are measured upon illumination of the NG108-15 cell with a 2 s light pulse of a wavelength of 532 nm at saturating intensity of 23 mW/mm² to determine the mean stationary current of the last 100 ms of the 2 s light pulse; and wherein the stationary photocurrent density is the quotient of the mean stationary current of the last 100 ms of the 2 s light pulse and the capacitance.

E17. The mutant ion channel of any one of E1-E16, wherein the mutant ion channel provides an at least 1.5-times, at least 1.7-times, or at least 2.0-times, and, e.g., up to 5.5-times, up to 5.0-times, or up to 4.5-times, higher mean stationary photocurrent density than a reference ion channel which has a Thr at the amino acid position corresponding to T218 in SEQ ID NO:5 and a Ser at the amino acid position corresponding to S220 in SEQ ID NO:5 and otherwise is identical to the mutant ion channel;

wherein the mean stationary photocurrent density is the mean of the stationary photocurrent densities of at least 5, at least 10, at least 15, e.g., 5-100, 10-75 or 15-60 individual NG108-15 cells expressing the mutant ion channel or from the stationary photocurrent densities of the same number of individual NG108-15 cells expressing the reference ion channel, respectively;

wherein the stationary photocurrent density of an individual NG108-15 cell is measurable by whole-cell patch-clamp measurements;

in said whole-cell patch-clamp measurements:

transient capacitive currents in response to voltage steps are measured to determine the capacitance of the NG108-15 cell, and photocurrents at a membrane potential of –60 mV are measured upon illumination of the NG108-15 cell with a 2 s light pulse of a wavelength of 532 nm at saturating intensity of 23 mW/mm² to determine the mean stationary current of the last 100 ms of the 2 s light pulse; and wherein the stationary photocurrent density of the NG108-15 cell is the quotient of the mean stationary current of the last 100 ms of the 2 s light pulse and the capacitance of the NG108-15 cell.

E18. The mutant ion channel of any one of E1-E17, wherein the mutant ion channel has:

an Asp at the amino acid position corresponding to D115 in SEQ ID NO:5, a Thr or Val, preferably a Thr, at the amino acid position corresponding to T119 in SEQ ID NO:5, and an Asp at the amino acid position corresponding to D126 in SEQ ID NO:5.

E19. The mutant ion channel of any one of E1-E18, wherein said capability of being activated by light is the capability of the mutant ion channel to provide a photocurrent in a cell which comprises the mutant ion channel in its plasma membrane and is exposed to light, in particular light of a wavelength in the range of 400-600 nm, 450-570 nm or 500-540 nm.

E20. The mutant ion channel of E19, wherein said photocurrent is characterized in that the mutant ion channel provides a stationary photocurrent density of at least 50%, at least 60%, at least 70%, at least 80%, at least 90%, or at least 100% of the stationary photocurrent density provided by the wild-type ion channel RICCR1 set forth in SEQ ID NO: 5;

wherein the stationary photocurrent density is measurable by whole-cell patch-clamp measurements with an NG108-15 cell expressing the mutant ion channel or RICCR1 set forth in SEQ ID NO: 5, respectively;

in said whole-cell patch-clamp measurements:

transient capacitive currents in response to voltage steps are measured to determine the capacitance of the NG108-15 cell, and photocurrents at a membrane potential of –60 mV are measured upon illumination of the NG108-15 cell with a 2 s light pulse of a wavelength of 532 nm at saturating intensity of 23 mW/mm² to determine the mean stationary current of the last 100 ms of the 2 s light pulse; and wherein the stationary photocurrent density is the quotient of the mean stationary current of the last 100 ms of the 2 s light pulse and the capacitance.

E21. The mutant ion channel of E19 or E20, wherein said photocurrent is characterized in that the mutant ion channel provides a mean stationary photocurrent density of at least 50%, at least 60%, at least 70%, at least 80%, at least 90%, or at least 100% of the mean stationary photocurrent density provided by the wild-type ion channel RICCR1 set forth in SEQ ID NO: 5;

wherein the mean stationary photocurrent density is the mean of the stationary photocurrent densities of at least 5, at least 10, at least 15, e.g., 5-100, 10-75 or 15-60 individual NG108-15 cells expressing the mutant ion channel or from the stationary photocurrent densities of the same number of individual NG108-15 cells expressing RICCR1 set forth in SEQ ID NO: 5, respectively;

wherein the stationary photocurrent density of an individual NG108-15 cell is measurable by whole-cell patch-clamp measurements;

in said whole-cell patch-clamp measurements:

transient capacitive currents in response to voltage steps are measured to determine the capacitance of the NG108-15 cell, and photocurrents at a membrane potential of –60 mV are measured upon illumination of the NG108-15 cell with a 2 s light pulse of a wavelength of 532 nm at saturating intensity of 23 mW/mm² to determine the mean stationary current of the last 100 ms of the 2 s light pulse; and wherein the stationary photocurrent density of the NG108-15 cell is the quotient of the mean stationary current of the last 100 ms of the 2 s light pulse and the capacitance of the NG108-15 cell.

E22. A nucleic acid, comprising a nucleotide sequence coding for the mutant ion channel of any one of E1-E21.

E23. An expression vector, comprising a nucleotide sequence coding for the mutant ion channel of any one of E1-E21 or the nucleic acid of E22.

E24. A cell comprising the nucleic acid of E22 or the expression vector according to E23.

E25. The cell of E24, wherein the cell comprises a mutant ion channel of any one of E1-E21 in its plasma membrane.

E26. The cell of any one of E24-E25, wherein the cell is an ex vivo cell, such as a cell in a sample that has been obtained from a human or non-human animal.

E27. The cell of any one of E24-E26 wherein the cell is a somatic cell.

E28. The cell of any one of E24-E27, wherein the cell is not a cell of an embryo, in particular not a cell of a human embryo.

E29. The cell of any one of E24-E28, wherein the cell is a mammalian cell.

E30. The cell of any one of E24-E29, wherein the cell is selected from (a) a hippocampal cell, a photoreceptor cell, a retinal rod cell, a retinal cone cell, a retinal ganglion cell, a bipolar neuron, a ganglion cell, a pseudounipolar neuron, a multipolar neuron, a pyramidal neuron, a Purkinje cell, a granule cell;

(b) a neuroblastoma cell, in particular NG108-15; a HEK293 cell; a COS cell; a BHK cell; a CHO cell; a myeloma cell; a MDCK cell.

E31. Use of a mutant ion channel of any one of E1-E21, or a cell of any one of E24-E30 in a high-throughput screening.

E32. Non-therapeutic use of a mutant ion channel of any one of E1-E21, a nucleic acid of E22, or an expression vector of E23 for rendering cells sensitive to stimulation with light, wherein the cells comprise the mutant ion channel in their plasma membranes.

E33. The use of E32, wherein the cells comprising mutant ion channels of any one of E1-E21 in their plasma membranes are generated by introducing a nucleic acid of E22 or an expression vector of E23, preferably an expression vector of E23, into parent cells which lack the mutant ion channel.

E34. The use of any one of E32-E33, wherein the stimulation with light modulates the voltage potential of the cells.

E35. The use of any one of E32-E34, wherein the light has a wavelength in the range of 400-600 nm, in particular 450-570 nm, more particularly 500-540 nm.

E36. The use of any one of E32-E35, wherein the use is an ex vivo use, such as an in vitro use.

E37. A non-therapeutic method for illuminating a targeted tissue that comprises cells having the mutant ion channel of any one of E1-E21 in their plasma membranes, wherein the method comprises using a light applicator to deliver light to the targeted tissue, wherein the light applicator comprises a light source and is operatively coupled to a controller, a power supply, and an implantable illuminance sensor such that the controller causes the power supply to let current flow to the light source to cause an emission of photons to the implantable light applicator based at least in part upon an output signal from the implantable illuminance sensor, wherein the implantable illuminance sensor is positioned such that it captures at least a portion of the photons directed toward the targeted tissue by the implantable light applicator.

E38. The method of E37, wherein the light source delivers light of a wavelength in the range of 400-600 nm, in particular 450-570 nm, more particularly 500-540 nm.

E39. The method of any one of E37-E38 wherein the illuminance sensor is selected from a photovoltaic cell, a photodiode, a pyroelectric sensor, a photoresistor, a photoconductor, a phototransistor and a photogalvanic sensor.

E40. The method of any one of E37-E39, further comprising providing a physiologic sensor configured to produce an output signal that is correlated with a physiologic response of the targeted tissue to the input of light.

E41. The method of E40, wherein the physiologic sensor is selected from an electromyogram sensor, an electroneurogram sensor, electroencephalogram sensor, an electrocardiogram sensor, a pressure sensor, a temperature sensor, a chemometric sensor, a motion sensor, an accelerometer, a gyro, a strain sensor, an impedance sensor and a capacitance sensor.

E42. The method of any one of E37-E41, wherein the method is an ex vivo method, such as an in vitro method.

E43. A non-therapeutic method for modulating the voltage potential of cells in response to stimulation with light;

wherein the cells comprise a mutant ion channel of any one of E1-E21 in their plasma membrane; and wherein the method comprises exposing the cells to light so as to modulate the voltage potential of the cells.

E44. The method of E43, wherein the light has a wavelength in the range of 400-600 nm, in particular 450-570 nm, more particularly 500-540 nm.

E45. The method of any one of E43-E44 wherein the method is an ex vivo method, such as an in vitro method.

E46. The use of any one of E32-E36, or the method of any one of E37-E45, wherein the cells are in a sample that has been obtained from a human or non-human animal.

E47. The use of any one of E32-E36 and E46, or the method of any one of E37-E46, wherein the cells are not cells of an embryo, in particular not cells of a human embryo.

E48. The use of any one of E32-E36, E46 and E47, or the method of any one of E37-E47, wherein the cells are mammalian cells.

E49. The use of any one of E32-E36 and E46-E48, or the method of any one of E37-E48, wherein the cells are somatic cells, preferably selected from one or more of neurons, myocytes and skeletal muscle cells.

E50. The use or the method of E49, wherein the cells are neurons of the optic pathway of a human or non-human animal, and are cells in a sample that has been obtained from said animal.

E51. The use or the method of E49, wherein the cells are neurons of the auditory pathway of a human or non-human animal, and are cells in a sample that has been obtained from said animal.

E52. The use or the method of E49, wherein the cells comprise myocytes and/or skeletal muscle cells in a sample that has been obtained from a human or non-human animal.

E53. A device comprising:

(a) a container comprising the mutant ion channel of any one of E1-E21, a nucleic acid of E22, or an expression vector of E23; and (b) a light source.

E54. The device of E53, wherein the device is implantable.

E55. The device of any one of E53-E54, may comprise one or more optical fibers configured to transmit light from the light source to a target structure of interest.

E56. The device of any one of E53-E55, wherein the light source and, if present, the optical fibers are part of an implantable light applicator configured to deliver light to a targeted tissue after implantation in a location adjacent to the targeted tissue, and wherein the device further comprises:

(c) a controller;

(d) a power supply; and (e) an implantable illuminance sensor, wherein the controller causes the power supply to let current flow to the light source to cause an emission of photons to the implantable light applicator based at least in part upon an output signal from the implantable illuminance sensor;

wherein the implantable illuminance sensor is configured such that it can be positioned to capture at least a portion of the photons directed toward the targeted tissue by the implantable light applicator.

E57. The device of E53-E56 wherein the implantable illuminance sensor is selected from a photovoltaic cell, a photodiode, a pyroelectric sensor, a photoresistor, a photoconductor, a phototransistor and a photogalvanic sensor.

E58. The device of any one of E53-E57, further comprising a physiologic sensor configured to produce an output signal that is correlated with a physiologic response of the targeted tissue to the input of light.

E59. The device of E58, wherein the physiologic sensor is selected from an electromyogram sensor, an electroneurogram sensor, electroencephalogram sensor, an electrocardiogram sensor, a pressure sensor, a temperature sensor, a chemometric sensor, a motion sensor, an accelerometer, a gyro, a strain sensor, an impedance sensor and a capacitance sensor.

E60. The device of any one of E53-E59, wherein the light source is configured to deliver light of a wavelength in the range of 400-600 nm, in particular 450-570 nm, more particularly 500-540 nm.

E61. The mutant ion channel of any one of E1-E21, the nucleic acid of E22, or the expression vector of E23 for use in medicine.

E62. The mutant ion channel of any one of E1-E21, the nucleic acid of E22, or the expression vector of E23 for use in a method of treating or ameliorating loss of vision or loss of hearing, in particular for use in a method of restoring, at least partially, loss of vision or loss of hearing.

E63. A non-human animal, comprising a mutant ion channel of any one of E1-E21, a nucleic acid of E22, an expression vector of E23, or a cell of any one of E24-E30.

E64. A method of using a mutant ion channel of any one of E1-E21, a nucleic acid of E22, or an expression vector of E23 for rendering cells sensitive to stimulation with light, wherein the method comprises the step of using the mutant ion channel, the nucleic acid or the expression vector to confer to said cells sensitivity to light, wherein the cells comprise the mutant ion channel in their plasma membranes.

E65. The method of E64, wherein the method further comprises generating the cells comprising mutant ion channels of any one of E1-E21 in their plasma membranes by introducing a nucleic acid of E22 or an expression vector of E23, preferably an expression vector of E23, into parent cells which lack the mutant ion channel.

E66. The method of any one of E64-E65, wherein the stimulation with light modulates the voltage potential of the cells.

E67. The method of any one of E64-E66, wherein the light has a wavelength in the range of 400-600 nm, in particular 450-570 nm, more particularly 500-540 nm.

E68. A method for illuminating a targeted tissue in a human or non-human animal, wherein the targeted tissue comprises cells having the mutant ion channel of any one of E1-E21 in their plasma membranes, wherein the method comprises using an implantable light applicator to deliver light to the targeted tissue after implantation in a location adjacent to the targeted tissue, wherein the light applicator comprises a light source and is operatively coupled to a controller, a power supply, and an implantable illuminance sensor such that the controller causes the power supply to let current flow to the light source to cause an emission of photons to the implantable light applicator based at least in part upon an output signal from the implantable illuminance sensor, wherein the implantable illuminance sensor is positioned such that it captures at least a portion of the photons directed toward the targeted tissue by the implantable light applicator.

E69. The method of E68, wherein the light source delivers light of a wavelength in the range of 400-600 nm, in particular 450-570 nm, more particularly 500-540 nm.

E70. The method of any one of E68-E69, wherein the implantable illuminance sensor is selected from a photovoltaic cell, a photodiode, a pyroelectric sensor, a photoresistor, a photoconductor, a phototransistor and a photogalvanic sensor.

E71. The method of any one of E68-E70, further comprising using a physiologic sensor to produce an output signal that is correlated with a physiologic response of the targeted tissue to the input of light.

E72. The method of E71, wherein the physiologic sensor is selected from an electromyogram sensor, an electroneurogram sensor, electroencephalogram sensor, an electrocardiogram sensor, a pressure sensor, a temperature sensor, a chemometric sensor, a motion sensor, an accelerometer, a gyro, a strain sensor, an impedance sensor and a capacitance sensor.

E73. A method for modulating the voltage potential of cells in response to stimulation with light;

wherein the cells are selected from one or more of neurons, myocytes and skeletal muscle cells, and comprise mutant ion channels of any one of E1-E21 in their plasma membranes; and wherein the method comprises exposing the cells to light so as to modulate the voltage potential of the cell.

E74. The method of E73, wherein the light has a wavelength in the range of 400-600 nm, in particular 450-570 nm, more particularly 500-540 nm.

E75. The method of any one of E64-E74, wherein the cells are in a human or non-human animal.

E76. The method of E75, wherein the animal suffers from a condition selected from loss of vision and loss of hearing, and the method is a method of treating or ameliorating said condition, in particular a method of restoring, at least partially, loss of vision or loss of hearing.

E77. The method of any one of E64-E76, wherein the cells are not cells of an embryo, in particular not cells of a human embryo.

E78. The method of any one of E64-E77, wherein the cells are mammalian cells.

E79. The method of any one of E64-E78, wherein the cells are somatic cells, preferably selected from one or more of neurons, myocytes and skeletal muscle cells.

E80. The method of E79, wherein the cells are neurons of the optic pathway.

E81. The method of E79, wherein the cells are neurons of the auditory pathway.

E82. The method of E79, wherein the cells comprise myocytes and/or skeletal muscle cells.

Of course, all embodiments as disclosed herein can be applied alone or in combination with other embodiments.

---

DESCRIPTION OF THE SEQUENCES

Figure 1:
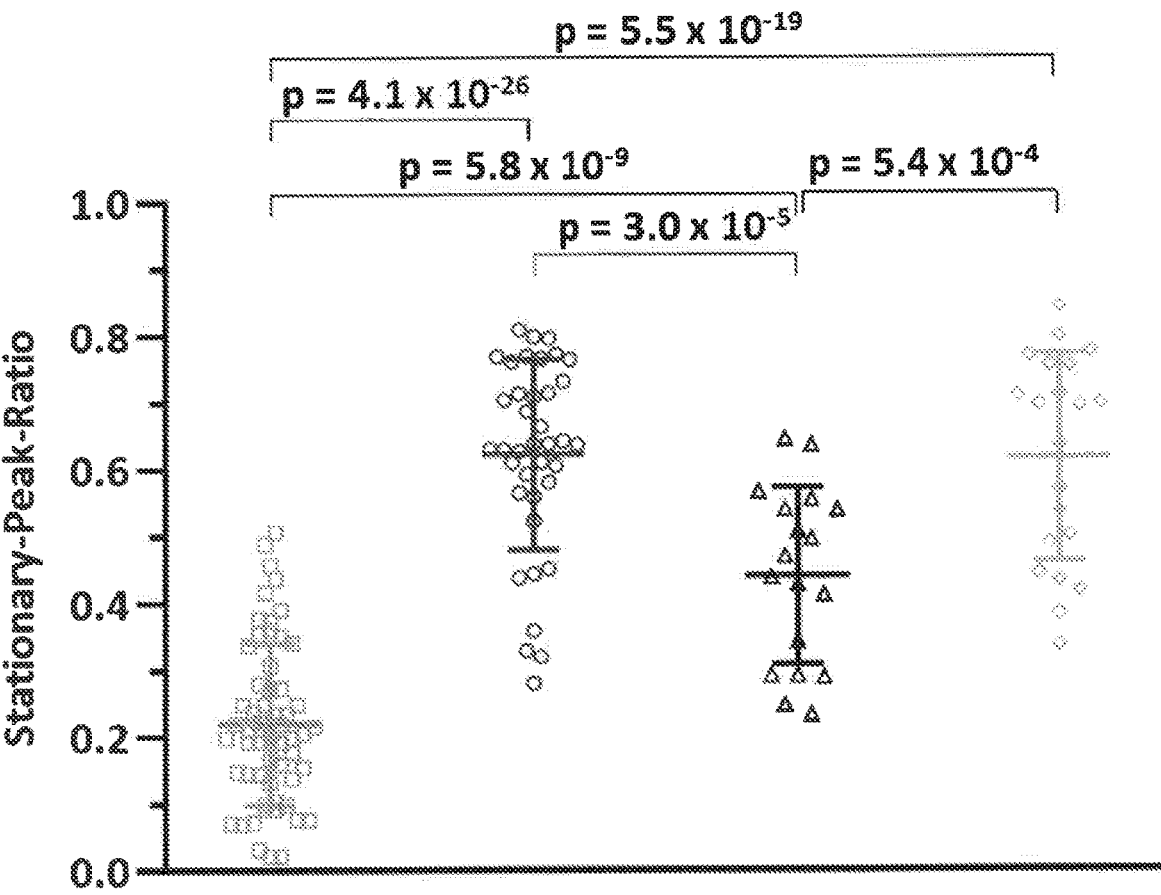
FIG. 1: R/CCR1 mutants with reduced desensitization (increased Stationary-Peak-Ratio) at saturating intensity. NG108-15 cells transiently transfected with R/CCR1-EYFP (WT) (square), R/CCR1-EYFP S220A (circle), R/CCR1-EYFP T218L (triangle) and R/CCR1-EYFP T218L/S220A (rhombus) were investigated by whole-cell patch-clamp recordings at a membrane potential of −60 mV. Number of cells measured as indicated by n numbers in the legend. Photocurrents were measured upon illumination with a 2 s light pulse of a wavelength of $\lambda$=532 nm at saturating intensity of 23 mW/mm$^2$. The stationary-peak-ratio was calculated as the quotient of the mean stationary current of the last 100 ms of the 2 s light pulse and the peak current. Bars indicate mean and SD. Statistical analysis was performed by one-way ANOVA followed by post-hoc Bonferroni-test. P-values<0.05 were considered significant.

SEQ ID NO: 1 (ChR2 (chop2-315); accession number of Chop2-737: AF461397; 315 aa)
MDYGGALSAVGRELLFVTNPVVVNGSVLVPEDQCYCAGWIESRGTNGAQTASNVLQWLAAGF
SILLLMFYAYQTWKSTCGWEEIYVCAIEMVKVILEFFFEFKNPSMLYLATGHRVQWLRYAEWL
LTCPVILIHLSNLTGLSNDYSRRTMGLLVSDIGTIVWGATSAMATGYVKVIFFCLGLCYGANTFF
HAAKAYIEGYHTVPKGRCRQVVTGMAWLFFVSWGMFPILFILGPEGFGVLSVYGSTVGHTIID
LMSKNCWGLLGHYLRVLIHEHILIHGDIRKTTKLNIGGTEIEVETLVEDEAEAGAVNKGTGK SEQ ID NO: 2 (Chrimson; accession number: KF992060; 350 aa)
MAELISSATRSLFAAGGINPWPNPYHHEDMGCGGMTPTGECFSTEWWCDPSYGLSDAGYGY
CFVEATGGYLVVGVEKKQAWLHSRGTPGEKIGAQVCQWIAFSIAIALLTFYGFSAWKATCGW
EEVYVCCVEVLFVTLEIFKEFSSPATVYLSTGNHAYCLRYFEWLLSCPVILIKLSNLSGLKNDYSK
RTMGLIVSCVGMIVFGMAAGLATDWLKWLLYIVSCIYGGYMYFQAAKCYVEANHSVPKGHCR
MVVKLMAYAYFASWGSYPILWAVGPEGLLKLSPYANSIGHSICDIIAKEFWTFLAHHLRIKIHE
HILIHGDIRKTTKMEIGGEEVEVEEFVEEEDEDTV SEQ ID NO: 3 (VChR1; accession number: EU622855; 300 aa)
MDYPVARSLIVRYPTDLGNGTVCMPRGQCYCEGWLRSRGTSIEKTIAITLQWVVFALSVACLG
WYAYQAWRATCGWEEVYVALIEMMKSIIEAFHEFDSPATLWLSSGNGVVWMRYGEWLLTCP
VLLIHLSNLTGLKDDYSKRTMGLLVSDVGCIVWGATSAMCTGWTKILFFLISLSYGMYTYFHAA
KVYIEAFHTVPKGICRELVRVMAWTFFVAWGMFPVLFLLGTEGFGHISPYGSAIGHSILDLIAK
NMWGVLGNYLRVKIHEHILLYGDIRKKQKITIAGQEMEVETLVAEEED SEQ ID NO: 4 (ReaChR; accession number KF448069; 350 aa)
MVSRRPWLLALALAVALAAGSAGASTGSDATVPVATQDGPDYVFHRAHERMLFQTSYTLENN
GSVICIPNNGQCFCLAWLKSNGTNAEKLAANILQWVVFALSVACLGWYAYQAWRATCGWEE
VYVALIEMMKSIIEAFHEFDSPATLWLSSGNGVVWMRYGEWLLTCPVILIHLSNLTGLKDDYSK
RTMGLLVSDVGCIVWGATSAMCTGWTKILFFLISLSYGMYTYFHAAKVYIEAFHTVPKGLCRQ
LVRAMAWLFFVSWGMFPVLFLLGPEGFGHISPYGSAIGHSILDLIAKNMWGVLGNYLRVKIHE
HILLYGDIRKKQKITIAGQEMEVETLVAEEEDKYESS SEQ ID NO: 5 (RICCR1; ChRmine (RICCR1-309); accession number of RICCR1-332: MN585304; accession number of RICCR1-309 (ChRmine): MN194599; 309 aa; T218 and S220 highlighted in bold; D115 ,Y116, T119, D126, R136, S138, Y156 and Y260 underlined)
MAHAPGTDQMFYVGTMDGWYLDTKLNSVAIGAHWSCFIVLTITTFYLGYESWTSRGPSKRTS
FYAGYQEEQNLALFVNFFAMLSYFGKIVADTLGHNFGDVGPFIIGFGNYRYA<u>D</u>Y<u>M</u>L<u>T</u>CPMLVY
<u>D</u>LLYQLRAPY<u>R</u>V<u>S</u>CSAIIFAILMSGVLAEF<u>Y</u>AEGDPRLRNGAYAWYGFGCFWFIFAYSIVMSIVA
KQYSRLAQLAQDTGAEHSLHVLKFAVFTFSMLWILFPLVWAICPRGFGWIDDNWTEVAHCVC
DIVAKSC<u>Y</u>GFALARFRKTYDEELFRLLEQLGHDEDEFQKLELDMRLSSNGERLRRLS -continued

DESCRIPTION OF THE SEQUENCES

```
SEQ ID NO: 6 (RICCR1 T218L; 309 aa, mutated residue highlighted in bold)
MAHAPGTDQMFYVGTMDGWYLDTKLNSVAIGAHWSCFIVLTITTFYLGYESWTSRGPSKRTS
FYAGYQEEQNLALFVNFFAMLSYFGKIVADTLGHNFGDVGPFIIGFGNYRYADYMLTCPMLVY
DLLYQLRAPYRVSCSAIIFAILMSGVLAEFYAEGDPRLRNGAYAWYGFGCFWFIFAYSIVMSIVA
KQYSRLAQLAQDTGAEHSLHVLKFAVFLFSMLWILFPLVWAICPRGFGWIDDNWTEVAHCVC
DIVAKSCYGFALARFRKTYDEELFRLLEQLGHDEDEFQKLELDMRLSSNGERLRRLS SEQ ID NO: 7 (RICCR1 S220A; 309 aa, mutated residue highlighted in bold)
MAHAPGTDQMFYVGTMDGWYLDTKLNSVAIGAHWSCFIVLTITTFYLGYESWTSRGPSKRTS
FYAGYQEEQNLALFVNFFAMLSYFGKIVADTLGHNFGDVGPFIIGFGNYRYADYMLTCPMLVY
DLLYQLRAPYRVSCSAIIFAILMSGVLAEFYAEGDPRLRNGAYAWYGFGCFWFIFAYSIVMSIVA
KQYSRLAQLAQDTGAEHSLHVLKFAVFTFAMLWILFPLVWAICPRGFGWIDDNWTEVAHCVC
DIVAKSCYGFALARFRKTYDEELFRLLEQLGHDEDEFQKLELDMRLSSNGERLRRLS SEQ ID NO: 8 (RICCR1 T218L/S220A; 309 aa, mutated residues highlighted in bold)
MAHAPGTDQMFYVGTMDGWYLDTKLNSVAIGAHWSCFIVLTITTFYLGYESWTSRGPSKRTS
FYAGYQEEQNLALFVNFFAMLSYFGKIVADTLGHNFGDVGPFIIGFGNYRYADYMLTCPMLVY
DLLYQLRAPYRVSCSAIIFAILMSGVLAEFYAEGDPRLRNGAYAWYGFGCFWFIFAYSIVMSIVA
KQYSRLAQLAQDTGAEHSLHVLKFAVFLFAMLWILFPLVWAICPRGFGWIDDNWTEVAHCVC
DIVAKSCYGFALARFRKTYDEELFRLLEQLGHDEDEFQKLELDMRLSSNGERLRRLS SEQ ID NO: 9 (7-transmembrane-helix motif of RICCR1; 7TM motif of RICCR1;
Ser27 to Lys269 of SEQ ID NO:5; 243 aa)
SVAIGAHWSCFIVLTITTFYLGYESWTSRGPSKRTSFYAGYQEEQNLALFVNFFAMLSYFGKIV
ADTLGHNFGDVGPFIIGFGNYRYADYMLTCPMLVYDLLYQLRAPYRVSCSAIIFAILMSGVLAEF
YAEGDPRLRNGAYAWYGFGCFWFIFAYSIVMSIVAKQYSRLAQLAQDTGAEHSLHVLKFAVFT
FSMLWILFPLVWAICPRGFGWIDDNWTEVAHCVCDIVAKSCYGFALARFRK SEQ ID NO: 10 (7TM motif of RICCR1 T218L; Ser27 to Lys269 of SEQ ID NO: 6; 243
aa; mutated residue highlighted in bold)
SVAIGAHWSCFIVLTITTFYLGYESWTSRGPSKRTSFYAGYQEEQNLALFVNFFAMLSYFGKIV
ADTLGHNFGDVGPFIIGFGNYRYADYMLTCPMLVYDLLYQLRAPYRVSCSAIIFAILMSGVLAEF
YAEGDPRLRNGAYAWYGFGCFWFIFAYSIVMSIVAKQYSRLAQLAQDTGAEHSLHVLKFAVFL
FSMLWILFPLVWAICPRGFGWIDDNWTEVAHCVCDIVAKSCYGFALARFRK SEQ ID NO: 11 (7TM motif of RICCR1 S220A; Ser27 to Lys269 of SEQ ID NO: 7; 243
aa; mutated residue highlighted in bold)
SVAIGAHWSCFIVLTITTFYLGYESWTSRGPSKRTSFYAGYQEEQNLALFVNFFAMLSYFGKIV
ADTLGHNFGDVGPFIIGFGNYRYADYMLTCPMLVYDLLYQLRAPYRVSCSAIIFAILMSGVLAEF
YAEGDPRLRNGAYAWYGFGCFWFIFAYSIVMSIVAKQYSRLAQLAQDTGAEHSLHVLKFAVFT
FAMLWILFPLVWAICPRGFGWIDDNWTEVAHCVCDIVAKSCYGFALARFRK SEQ ID NO: 12 (7TM motif of RICCR1 T218L/S220A; Ser27 to Lys269 of SEQ ID
NO: 8; 243 aa; mutated residue highlighted in bold)
SVAIGAHWSCFIVLTITTFYLGYESWTSRGPSKRTSFYAGYQEEQNLALFVNFFAMLSYFGKIV
ADTLGHNFGDVGPFIIGFGNYRYADYMLTCPMLVYDLLYQLRAPYRVSCSAIIFAILMSGVLAEF
YAEGDPRLRNGAYAWYGFGCFWFIFAYSIVMSIVAKQYSRLAQLAQDTGAEHSLHVLKFAVFL
FAMLWILFPLVWAICPRGFGWIDDNWTEVAHCVCDIVAKSCYGFALARFRK SEQ ID NO: 13 (helix 6 motif of RICCR1 T218X¹/S220X²; Ala205 to Ile232 of SEQ ID
NO: 5 with amino acid mutations at one or both of T218 and S220 of SEQ ID NO: 5;
28 aa; variable residue highlighted in bold)
AEHSLHVLKFAVFX¹FX²MLWILFPLVWAI
``` wherein (a) $X^1$ is selected from L, I, V, M, C, F, A, G, P and W, and preferably is L, and $X^2$ is selected from A, G, L, V, I, M, P, C and W, and preferably is A; or (b) $X^1$ is selected from L, I, V, M, C, F, A, G, P and W, and preferably is L, and $X^2$ is selected from S, T, Y, Q and N, and preferably is S; or (c) $X^1$ is selected from T, S, Y, Q and N, and preferably is T, and $X^2$ is selected from A, G, L, V, I, M, P, C and W, and preferably is A.

The present invention is illustrated by the following examples which should not be construed as limiting the scope of the invention which is defined by the claims.

EXAMPLES

Example 1—Photocurrent Desensitization and Photocurrent Density of R/CCR1 Mutants in NG108-15 Cells Molecular biology. The humanized DNA sequence, coding for R/CCR1-309 (ChRmine, SEQ ID NO: 5, accession number: MN194599), C-terminally fused to EYFP was cloned into the mammalian expression vector pcDNA3.1 (-) (Invitrogen, Carlsbad, USA). EYFP was thereby flanked by the well-described targeting sequences TS and ES (i.e., TS-EYFP-ES) for optimized plasma membrane expression of the shown constructs (see ref. 26, 27). The resulting constructs are termed 'RICCR1-EYFP' herein (designation followed by mutation(s) if any). The mutations T218L and S220A were introduced into R/CCR1 by site-directed mutagenesis using the primers shown in table 1.

TABLE 1

| List of primers used for RICCR1 mutant generation. | | | |
|---|---|---|---|
| template | RICCR1 T218L humanized RICCR1 | RICCR1 S220A humanized RICCR1 | RICCR1 T218L/S220A humanized RICCR1 T218L |
| sequence of forward primer | 5'-GTTCGCCGTG TTTCTGTTCTCCA TGCTGTG-3' (SEQ ID NO: 14) | 5'-GTGTTTACCTT CGCCATGCTG TGGATTC-3' (SEQ ID NO: 16) | 5'-CGTGTTTCTG TTCGCCATGCT GTGGATTCTG-3' (SEQ ID NO: 18) |
| sequence of reverse primer | 5'-CACAGCATGG AGAACAGAAACAC GGCGAAC-3' (SEQ ID NO: 15) | 5'-GAATCCACAG CATGGCGAAG GTAAACAC-3' (SEQ ID NO: 17) | 5'-CAGAATCCAC AGCATGGCGAA CAGAAACACG-3' (SEQ ID NO: 19) |

NG108-15 cell culture and transfection. NG108-15 cells (ATCC, HB-12377TM, Manassas, USA) were cultured at 37° C. and 5% $CO_2$ in DMEM (Sigma, St. Louis, USA) supplemented with 10% fetal calf serum (Sigma, St. Louis, USA), and 5% penicillin/streptomycin (Sigma, St. Louis, USA). The cells were seeded on 24-well plates one day prior to transient transfections. Two to three days prior to the patch-clamp experiments the NG108-15 cells were transiently transfected with pcDNA3.1(-) carrying R/CCR1 or R/CCR1 mutants using Lipofectamine LtX (Invitrogen, Carlsbad, USA).

Electrophysiological recordings from NG108-15. For the electrophysiological characterization of R/CCR1 wt and the aforementioned R/CCR1 mutants whole cell patch-clamp measurement were performed under voltage clamp conditions using the Axopatch 200B amplifier (Axon Instruments, Union City, USA) and the DigiData 1322A interface (Axon Instruments, Union City, USA). Patch pipettes with resistances of 2-6 MΩ were fabricated from thin-walled borosilicate glass on a horizontal puller (Model P-1000, Sutter Instruments, Novato, USA). The series resistance was <15MΩ. The bath solution contained 140 mM NaCl, 2 mM $CaCl_2$, 2 mM $MgCl_2$, 10 mM HEPES, pH 7.4. and the pipette solution contained 110 mM NaCl, 2 mM $MgCl_2$, 10 mM EGTA, 10 mM HEPES, pH 7.4. All recordings were performed at room temperature (297 K). For determination and comparison of the off-kinetics, current densities and desensitization, NG108-15 cells heterologously expressing R/CCR1 and the aforementioned R/CCR1 mutants were investigated at a membrane potential of –60 mV. Photocurrents were measured in response to 3 ms or 2 s light pulses with a saturating intensity of 23 mW/mm² using diode-pumped solid-state lasers (λ=532) focused into a 400-μm optic fiber. Light pulses were applied by a fast computer-controlled shutter (Uniblitz LS6ZM2, Vincent Associates, Rochester, USA). The τoff value was determined by a fit of the decaying photocurrent, which was elicited in response to a 3 ms light pulse, to a monoexponential function. The stationary-peak-ratio was calculated as the quotient of the mean stationary current of the last 100 ms of the 2 s light pulse and the peak current. The current density (J-60 mV) was determined by dividing the stationary current in response to a 2 s light pulse with a saturating intensity of 23 mW/mm² by the capacitance of the cell. In order to avoid an experimental bias, the NG108-15 cells for the electrophysiological recordings were chosen independent of the brightness of their EYFP fluorescence.

Figure 2:
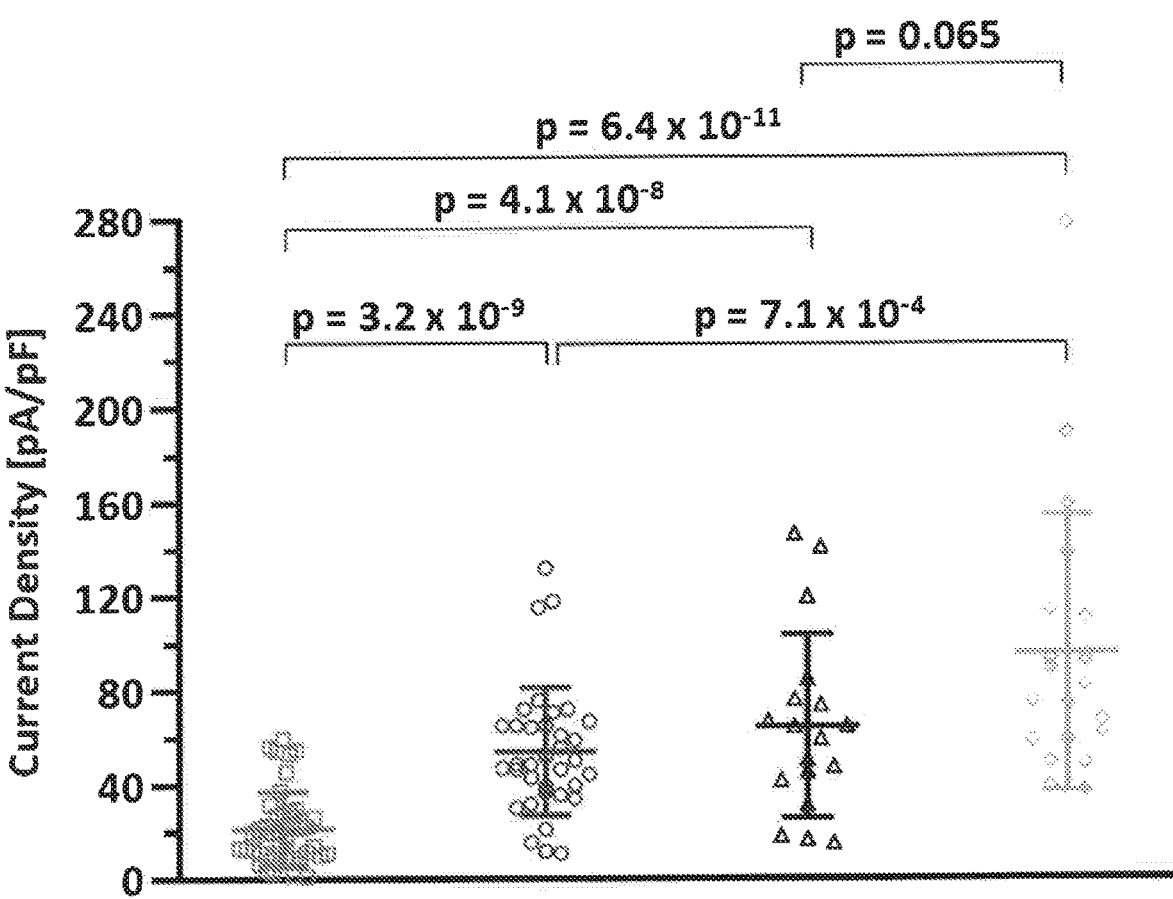
FIG. 2: R/CCR1 mutants with increased photocurrent density at saturating intensity. NG108-15 cells transiently transfected with R/CCR1-EYFP (WT) (square) (n=57), R/CCR1-EYFP S220A (circle) (n=38), R/CCR1-EYFP T218L (triangle) (n=18) and R/CCR1-EYFP T218L/S220A (rhombus) (n=21) were investigated by whole-cell patch-clamp recordings at a membrane potential of −60 mV. Photocurrents were measured upon illumination with a 2 s light pulse of a wavelength of $\lambda$=532 nm at saturating intensity of 23 mW/mm$^2$. Number of cells measured as indicated by n numbers in the legend. Photocurrent densities shown were calculated as the quotient of the mean stationary current of the last 100 ms of the 2 s light pulse normalized to cell capacitance. Bars indicate mean and SD. Statistical analysis was performed by one-way ANOVA followed by post-hoc Bonferroni-test. P-values<0.05 were considered significant.

The results are shown in FIGS. 1 and 2 and in Tables 2, 3 and 4 below.

As demonstrated by the shown results, mutations at positions T218 and S220 are significantly reducing photocurrent desensitization in R/CCR1. The stationary-peak-ratios of R/CCR1 T218L, R/CCR1 S220A and R/CCR1 T218L/S220A are significantly increased compared to the stationary-peak-ratio of R/CCR1 wt (FIG. 1 and Table 2). Accordingly, the mean stationary photocurrent densities of R/CCR1 T218L, R/CCR1 S220A and R/CCR1 T218L/S220A are significantly increased compared to the mean stationary photocurrent density of R/CCR1 wt (FIG. 2 and Table 3). For R/CCR1 T218L and R/CCR1 T218L/S220A the closing kinetics is unchanged compared to R/CCR1 wt (Table 4). The closing kinetics of R/CCR1 S220A is slower compared to the closing kinetics of R/CCR1 wt (Table 4).

TABLE 2

RICCR1 mutants show reduced desensitization (increased Stationary-Peak-Ratio) at saturating intensity. NG018-15 cells transfected with RICCR1-EYFP (WT) (n = 57), RICCR1-EYFP S220A (n = 38), RICCR1-EYFP T218L (n = 18) and RICCR1-EYFP T218L/S220A (n = 21) were investigated by whole-cell patch-clamp recordings at a membrane potential of –60 mV. Photocurrents were measured upon illumination with a 2 s light pulse of a wavelength of λ = 532 nm at saturating intensity of 23 mW/mm². The stationary-peak-ratio was calculated as the quotient of the mean stationary current of the last 100 ms of the 2 s light pulse and the peak current. Shown are mean and standard deviation (SD).

| | Stationary-Peak-Ratio at saturating intensity | | |
|---|---|---|---|
| Construct | Mean | SD | n |
| RICCR1-EYFP WT | 0.22 | 0.12 | 57 |
| RICCR1-EYFP S220A | 0.62 | 0.14 | 38 |
| RICCR1-EYFP T218L | 0.44 | 0.13 | 18 |
| RICCR1-EYFP T218L/S220A | 0.62 | 0.15 | 21 |

TABLE 3

Photocurrent density of RICCR1 mutants at saturating intensity. NG108-15 cells transfected with RICCR1-EYFP (WT) (n = 44), RICCR1-EYFP S220A (n = 35), RICCR1-EYFP T218L (n = 18) and RICCR1-EYFP T218L/S220A (n = 20) were investigated by whole-cell patch-clamp recordings at a membrane potential of −60 mV. Photocurrents were measured upon illumination with a 2 s light pulse of a wavelength of $\lambda = 532$ nm at saturating intensity of 23 mW/mm². Photocurrent densities shown were calculated as the quotient of the mean stationary current of the last 100 ms of the 2 s light pulse normalized to cell capacitance. Shown are mean and standard deviation (SD).

| Construct | Current density [pA/pF] at saturating intensity | | |
|---|---|---|---|
| | Mean | | |
| RICCR1-EYFP (WT) | 21.58 | 15.76 | 44 |
| RICCR1-EYFP S220A | 54.26 | 27.19 | 35 |
| RICCR1-EYFP T218L | 64.83 | 38.84 | 18 |
| RICCR1-EYFP T218L/S220A | 95.85 | 58.52 | 20 |

TABLE 4

Off-kinetics of the RICCR1 variants at −60 mV. NG018-15 cells transfected with RICCR1-EYFP (WT) (n = 7), RICCR1-EYFP S220A (n = 6), RICCR1- EYFP T218L (n = 7) and RICCR1-EYFP T218L/S220A (n = 7) were investigated by whole-cell patch-clamp recordings at a membrane potential of −60 mV. Displayed are Toff values measured upon illumination with a 3 ms light pulse of a wavelength of $\lambda = 532$ nm at saturating intensity of 23 mW/mm². Shown are mean and standard deviation (SD).

| Construct | $T_{off}$ at −60 mV [ms] | | |
|---|---|---|---|
| | Mean | SD | n |
| RICCR1-EYFP (WT) | 63 | 15 | 7 |
| RICCR1-EYFP S220A | 152 | 18 | 6 |
| RICCR1-EYFP T218L | 59 | 20 | 7 |
| RICCR1-EYFP T218L/S220A | 58 | 12 | 7 |

Example 2—Light Dependence of R/CCR1 Variants in NG108-15 Cells

Conditions and procedures, as described in Example 1, also apply for Example 2. The photocurrents were measured upon illumination with 2 s light pulses of a wavelength of $\lambda$=532 nm at light intensities ranging from 0.0024 mW/mm² to 23 mW/mm².

Figure 3:
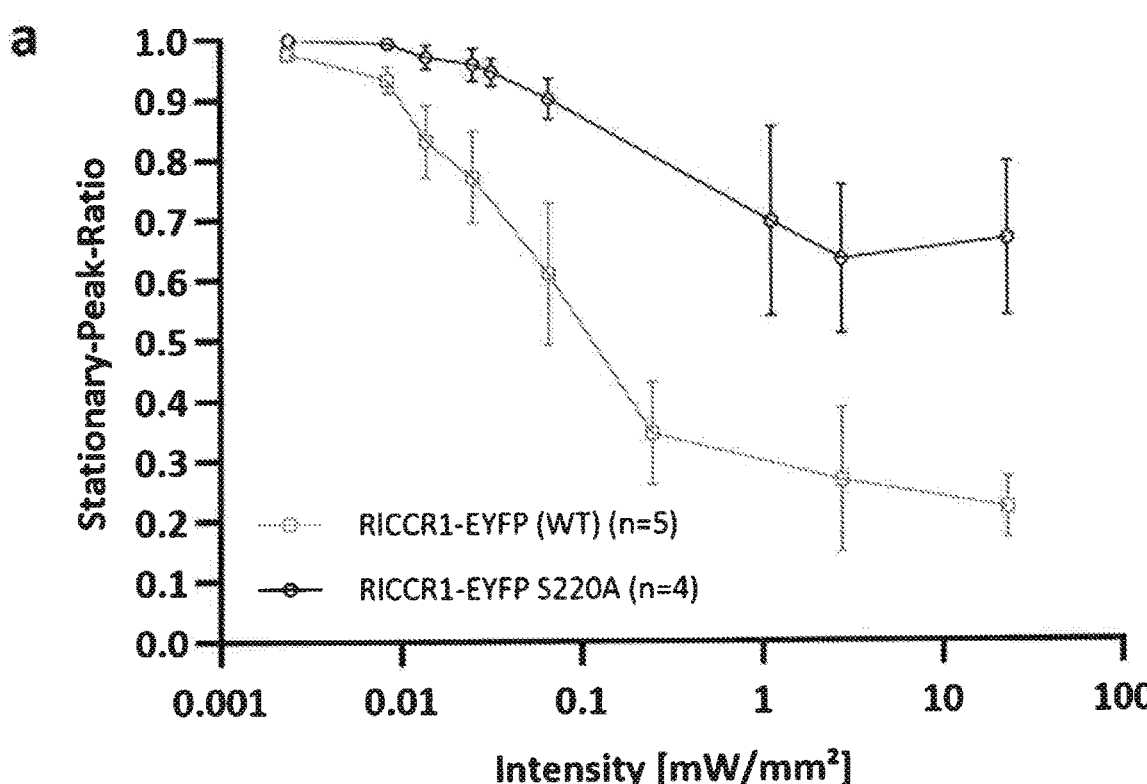
FIG. 3: Desensitization of R/CCR1 variants at different light intensities. NG108-15 cells transiently transfected with R/CCR1-EYFP (WT) (square), R/CCR1-EYFP S220A (circle), R/CCR1-EYFP T218L (triangle) and R/CCR1-EYFP T218L/S220A (rhombus) were investigated by whole-cell patch-clamp recordings at a membrane potential of −60 mV. Photocurrents were measured upon illumination with a 2 s light pulse of a wavelength of $\lambda$=532 nm at different light intensity ranging from 0.0024 mW/mm$^2$ to 23 mW/mm$^2$. The stationary-peak-ratio was calculated as the quotient of the mean stationary current of the last 100 ms of the 2 s light pulse and the peak current. Bars indicate mean and SD. (a), (c) and (e) show the stationary-peak-ratio across the range of light intensities for the R/CCR1 variants (a) R/CCR1-EYFP S220A (n=4), (b) R/CCR1-EYFP T218L (n=4) and (c) R/CCR1-EYFP T218L/S220A (n=4) in comparison to R/CCR1-EYFP (WT) (n=5). (b), (d) and (f) show exemplary photocurrent traces at saturating light intensity (23 mW/mm$^2$) of (b) R/CCR1-EYFP S220A, (d) R/CCR1-EYFP T218L and (f) R/CCR1-EYFP T218L/S220A in comparison to R/CCR1-EYFP (WT) with the wild type trace depicted in light grey which is (nearly entirely) above the trace for the respective R/CCR1 variant in dark grey.
Figure 3:
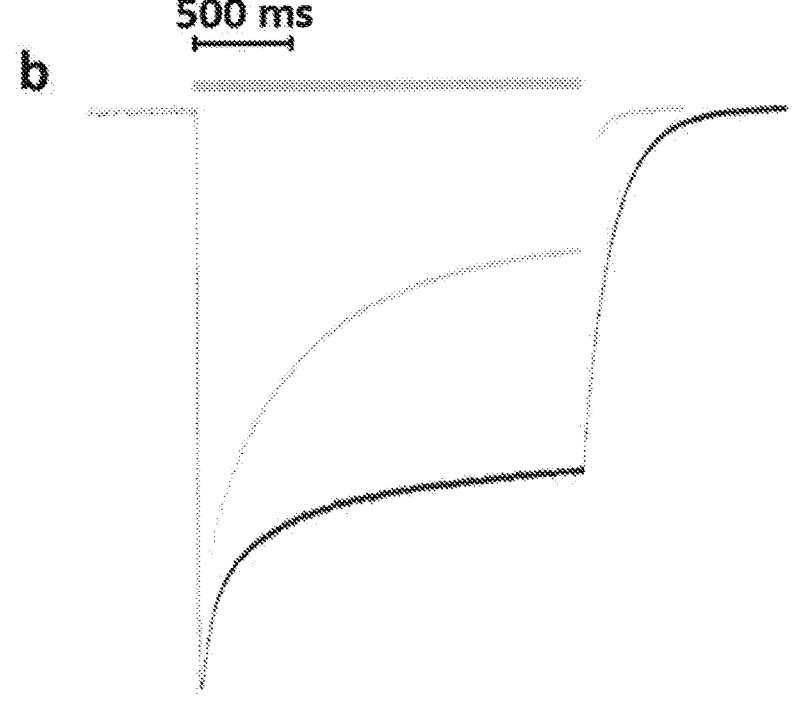
Figure 3:
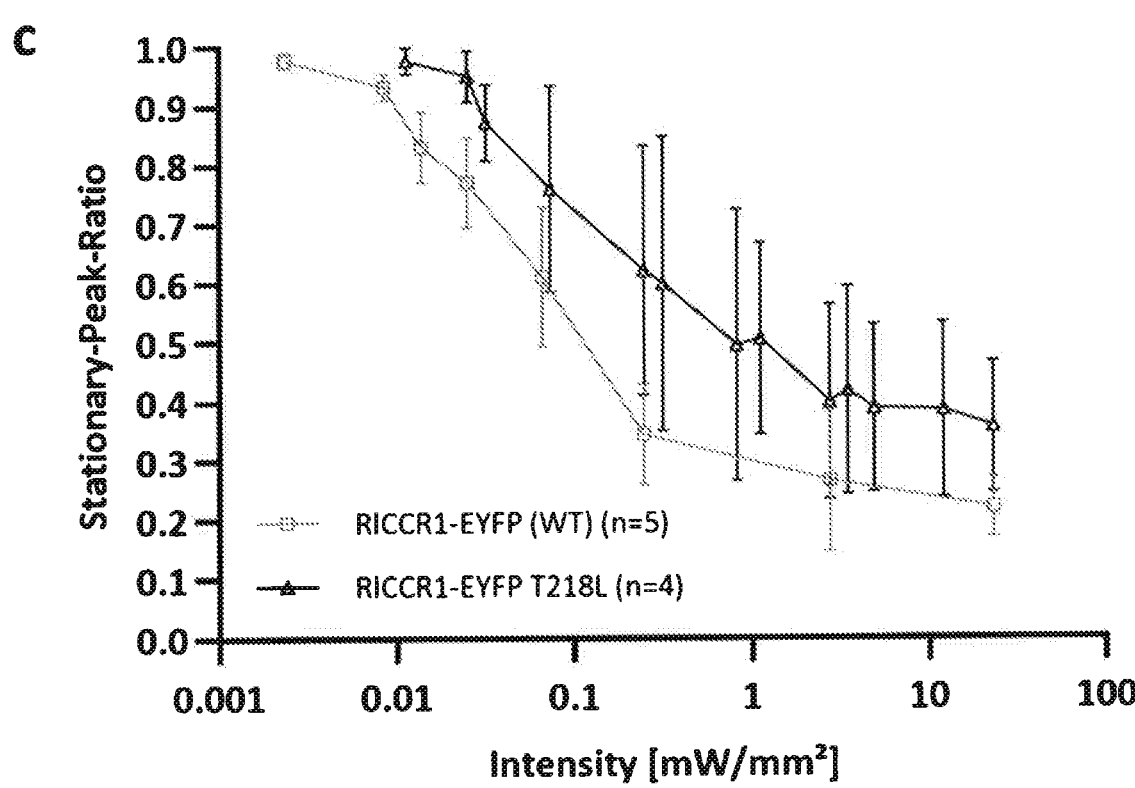
Figure 3:
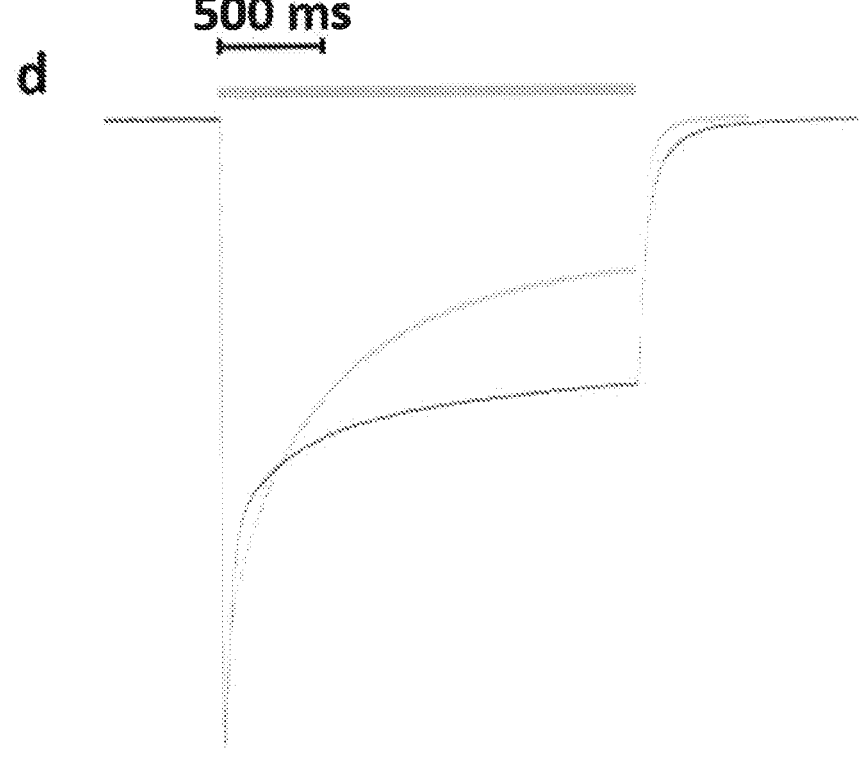
Figure 3:
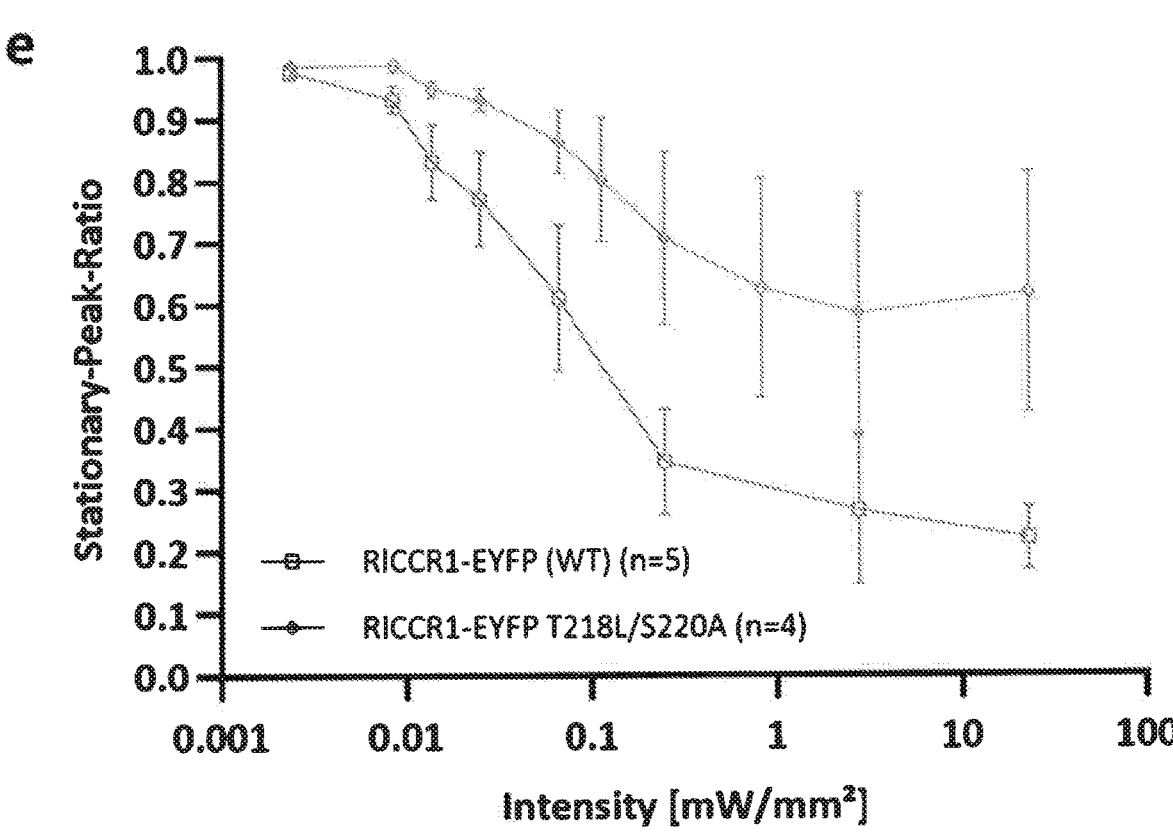
Figure 3:
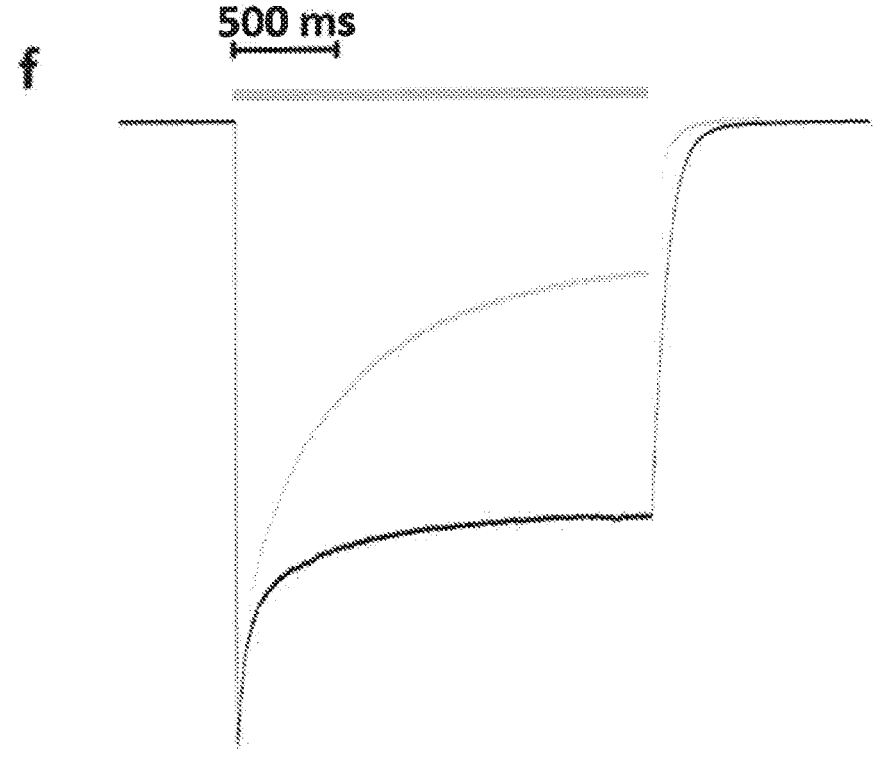
Figure 4:
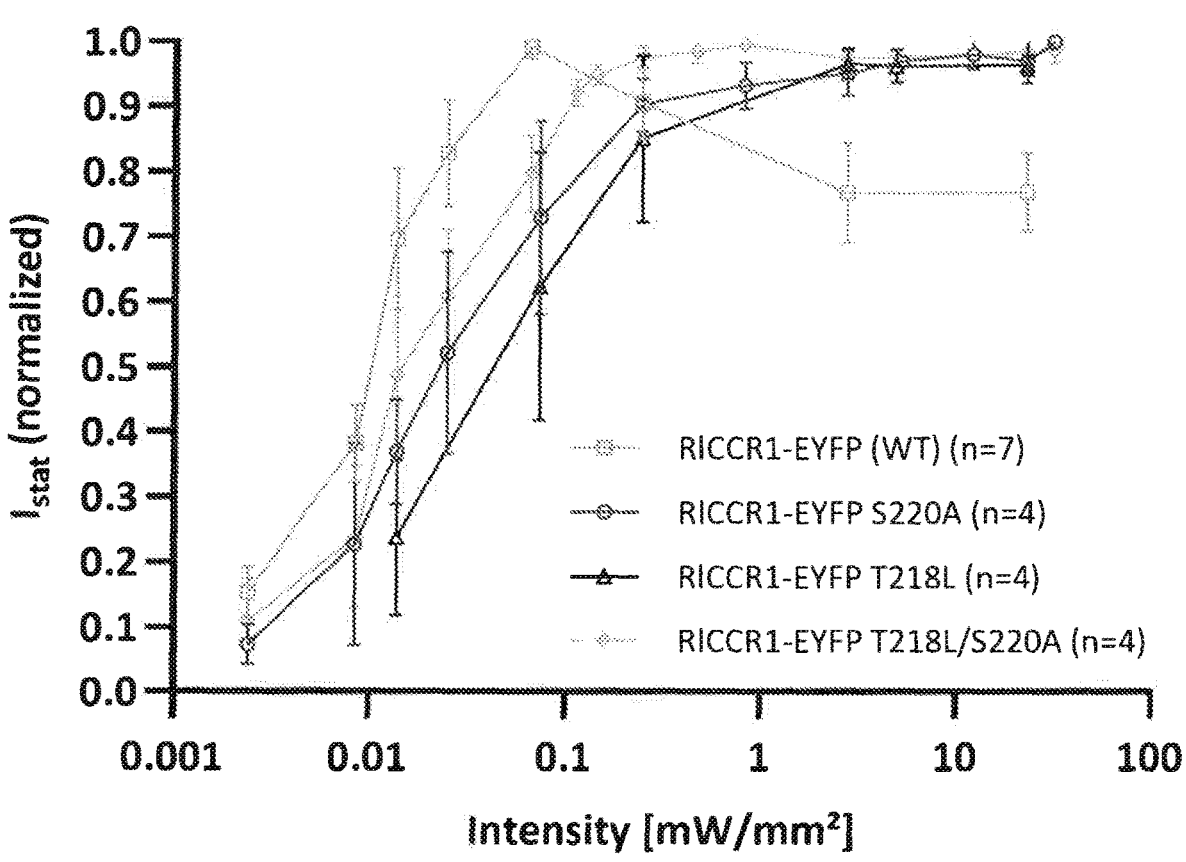
FIG. 4: Light intensity dependence of stationary photocurrent of R/CCR1 variants. NG108-15 cells transiently transfected with R/CCR1-EYFP (WT) (square), R/CCR1-EYFP S220A (circle), R/CCR1-EYFP T218L (triangle) and R/CCR1-EYFP T218L/S220A (rhombus) were investigated by whole-cell patch-clamp recordings at a membrane potential of −60 mV. Number of cells measured as indicated by n numbers in the legend. Stationary photocurrents were measured upon illumination with a 2 s light pulse of a wavelength of $\lambda$=532 nm at different light intensity ranging from 0.0024 mW/mm$^2$ to 23 mW/mm$^2$. The stationary photocurrent ($I_{stat}$) was measured as the mean stationary current of the last 100 ms of the 2 s light pulse and is depicted normalized to the maximum stationary current measured for each cell. Bars indicate mean and SD.
Figure 5:
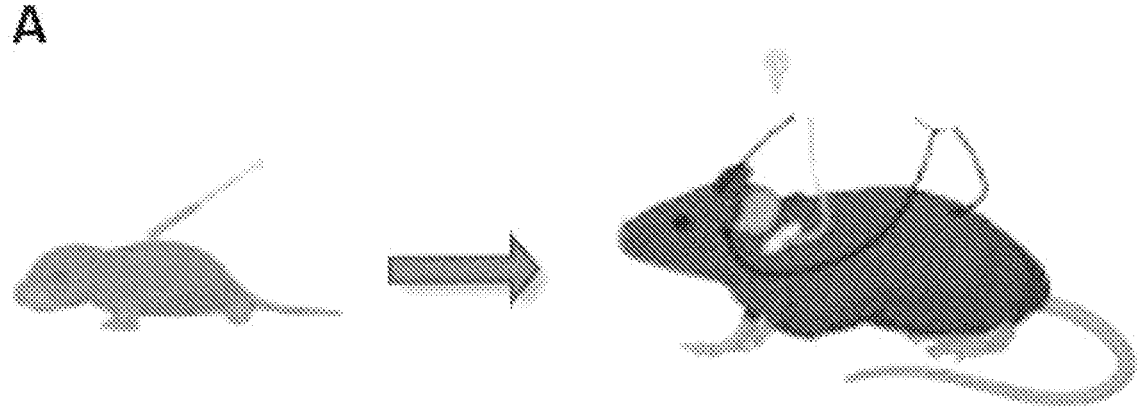
FIG. 5. Characterizing the optogenetic activation of the mouse auditory pathway by means of oABRs. A) Schematic representation of the approach to optogenetic manipulation and acquisition of optical auditory brainstem recordings (oABR) in mice. Spiral ganglion neurons (SGNs), were rendered light-sensitive by injection of AAV-ChR construct through the round window of mice at postnatal day 6. Following 6 to 13 weeks, the cochlea of mice was exposed, and a laser fiber, coupled to a 594 nm laser, was inserted into the round window. (B) oABRs driven with varying radiant flux (1 ms pulses at 10 and 20 Hz, grey levels code the radiant flux in mW) for an exemplary mouse injected with the AAV-ChR construct AAV2/9-R/CCR1-EYFP (WT). D) Threshold of minimum light intensity eliciting a detectable oABR response for R/CCR1-EYFP (WT) (light grey, left-hand side) and R/CCR1-EYFP T218L/S220A (dark gray, right-hand side). Student's t-test (**$P \leq 0.005$). E) P1-N1 amplitude, and F) P1 latency (1 ms pulses at 10 and 20 Hz; radiant flux from 20-37 mW). G) P1-N1 amplitudes with varying radiant flux (1 ms pulses at 10 and 20 Hz). H) Latency of oABR P1 with varying pulse duration (radiant flux 20-37 mW at 10 and 20 Hz). I) Latency of oABR P1 as a function of stimulus rate (1 ms pulses with radiant flux of 20-37 mW). Data represents mean (+/−SD) of n=6 mice injected with AAV2/9-R/CCR1-EYFP (WT), and n=8 mice injected with AAV2/9-R/CCR1-EYFP T218L/S220A.
Figure 5:
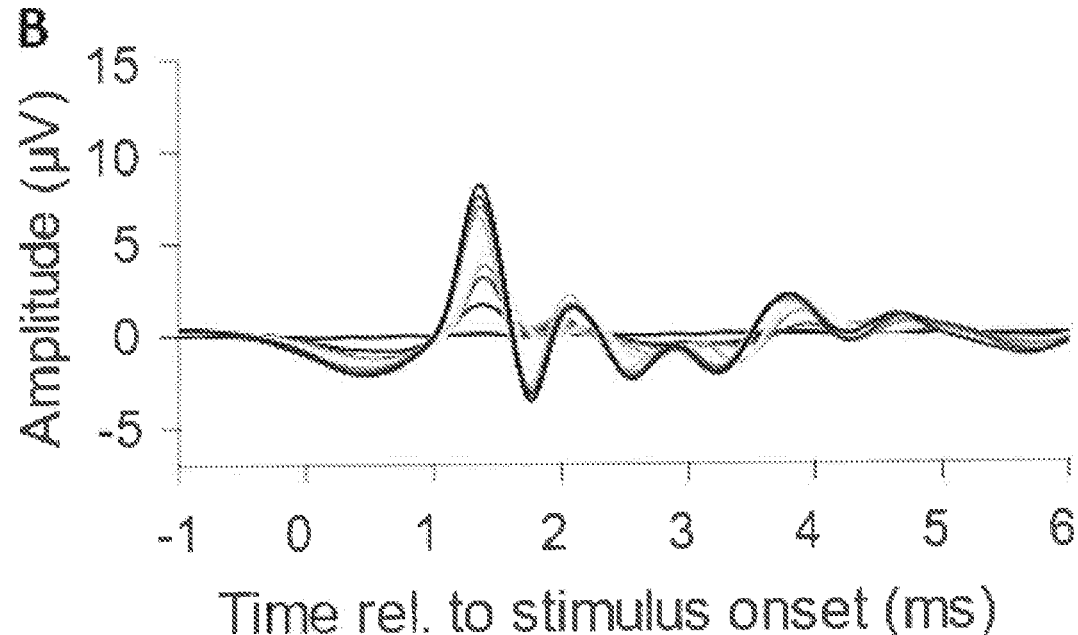
Figure 5:
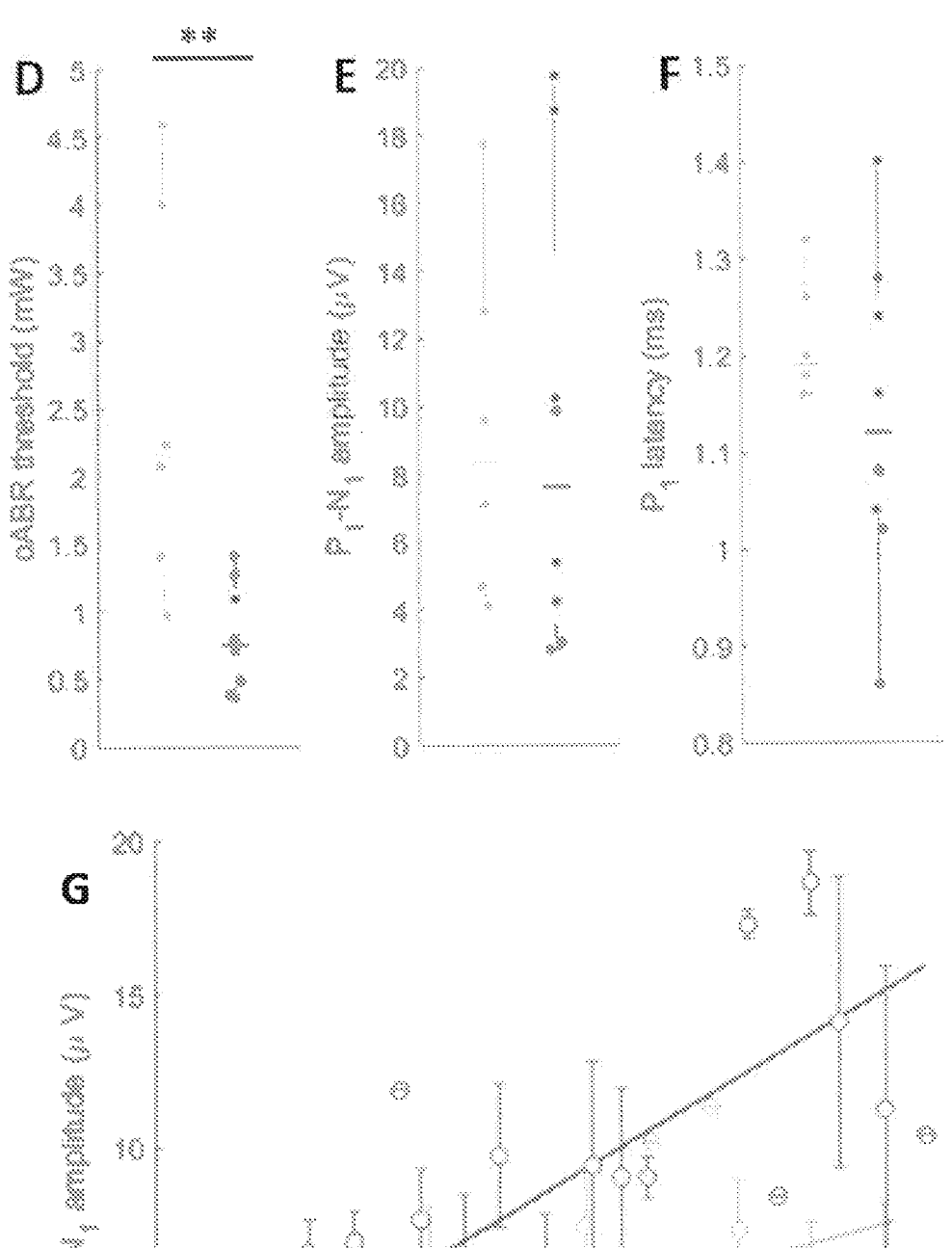
Figure 5:
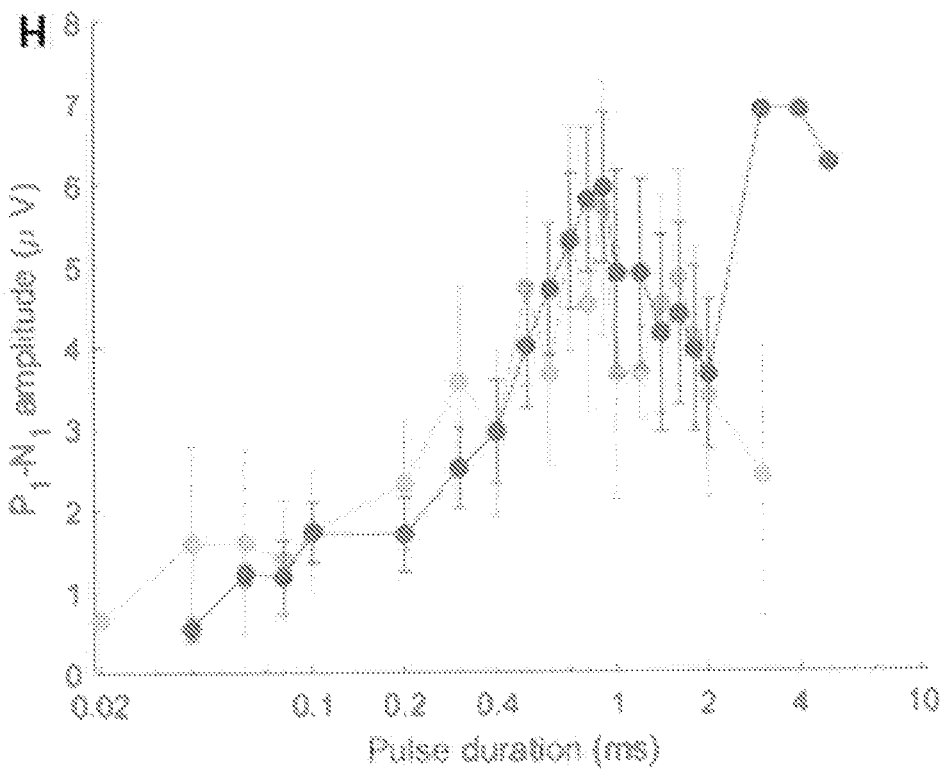
Figure 5:
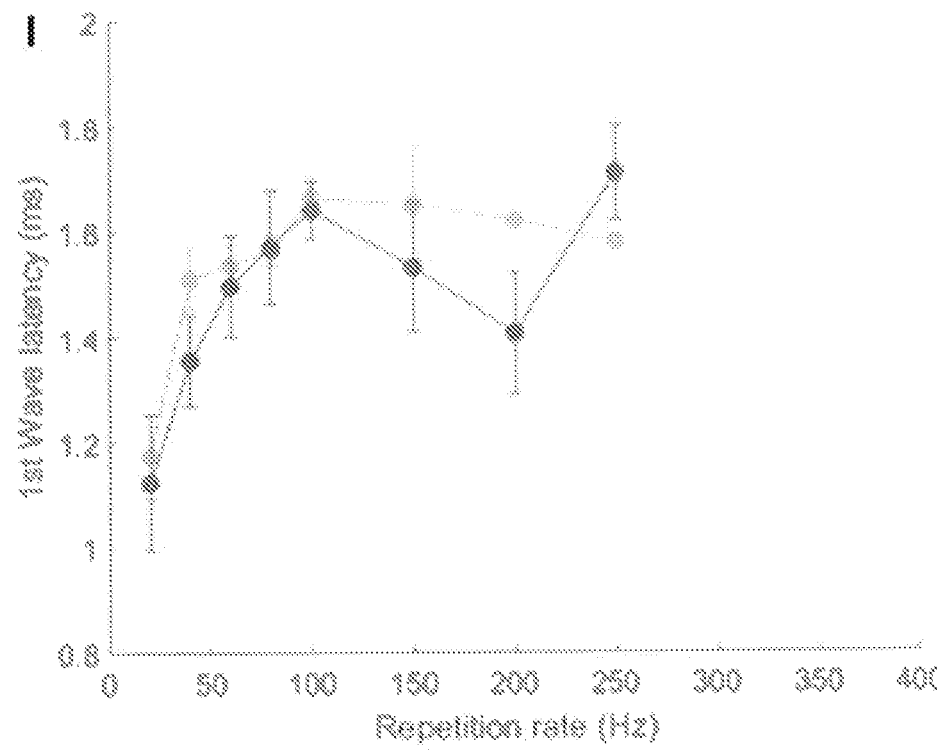

The results are shown in FIGS. 3 and 4 and in Table 5 below.

As demonstrated by the shown results, mutations at positions T218 and S220 are reducing photocurrent desensitization in R/CCR1 upon illumination with light pulses of different light intensities. At the indicated light intensities the stationary-peak-ratios of R/CCR1 T218L, R/CCR1 S220A and R/CCR1 T218L/S220A are increased compared to the stationary-peak-ratio of R/CCR1 wt (FIG. 3). The light sensitivities of the investigated R/CCR1 variants are depicted in table 5. The stationary photocurrent of R/CCR1 wt shows a non-hyperbolic dependence on light intensity (FIG. 4). Photocurrent reduction at high light intensities indicates a, to the knowledge of the present inventors, previously undescribed substrate (light) inhibition mechanism in R/CCR1. The R/CCR1 mutants, as disclosed herein, show a hyperbolic dependence on light intensity, which indicates suppression of this substrate inhibition mechanism.

TABLE 5

Light sensitivity of RICCR1 variants. NG108-15 cells, transfected with RICCR1-EYFP (WT), RICCR1-EYFP S220A, RICCR1-EYFP T218L and RICCR1-EYFP T218L/S220A, were investigated by whole-cell patch-clamp recordings at a membrane potential of −60 mV. Stationary photocurrents were measured upon illumination with a 2 s light pulse of a wavelength of $\lambda = 532$ nm at indicated light intensities. Half maximal activation ($EC_{50}$) was determined by hyperbolic fitting. Shown are mean and standard deviation (SD) of the resulting $EC_{50}$ values.

| Construct | $EC_{50}$ [mW/mm²] | | |
|---|---|---|---|
| | Mean | SD | n |
| RICCR1-EYFP (WT) | 0.014 | 0.005 | 6 |
| RICCR1-EYFP S220A | 0.031 | 0.017 | 4 |
| RICCR1-EYFP T218L | 0.029 | 0.014 | 5 |
| RICCR1-EYFP T218L/S220A | 0.020 | 0.007 | 4 |

Example 3—Optogenetic Stimulation of the Mouse Auditory Pathway by R/CCR1 Variants Animals. Data were obtained from 19 adult C57Bl/6 wild-type mice of either sex. Animals were kept in a 12 h light/dark cycle, with access to food and water ad libitum. For all procedures, animals were placed on a heating pad and the body temperature was monitored by a rectal thermometer and maintained at approximately 37° C. by a custommade heating pad. All experimental procedures were done in compliance with the German national animal care guidelines and approved by the local animal welfare committee of the University Medical Center Göttingen, as well as the responsible authorities of the state of Lower Saxony, Germany (LAVES).

Postnatal AAV injection into the cochlea. The AAV-ChR construct injections into scala tympani of the left ear via the round window was performed at postnatal day 6 in C57BL/6 wild-type mice. The right ear served as a non-injected control. The ChRs R/CCR1 wt or R/CCR1 T218L/S220A C-terminally tagged with EYFP, wherein the EYFP is flanked by targeting sequences TS and ES (see ref. 26, 27), which enhance plasma membrane expression (ChR-TS-EYFP-ES, herein designated "R/CCR1-EYFP") were expressed under the control of the human synapsin promoter and were delivered to spiral ganglion neurons (SGNs) using the viral capsid AAV2/9. In brief, mouse pups were randomly selected for virus injections. Under general isoflurane anesthesia (1-2%) combined buprenorphine (0.1 mg/kg) and carprofen (5 mg/kg) as well as local xylocaine for analgesia, the round window of the left ear was accessed via a retroauricular incision. The round window membrane was identified and gently punctured using a borosilicate capillary pipette, which was kept in place to inject the virus of varying titers: $1.96 \times 10^{12}$ to $1.48 \times 10^{13}$ genome copies/ml. After virus injection, the tissue surrounding the injection site was repositioned and the wound was sutured. Recovery of the animals was accompanied with carprofen (5 mg/kg) the day after the surgery.

Optical stimulation in vivo. Six to thirteen weeks after virus injections, in vivo optical stimulation and recordings were performed under anesthesia using isoflurane (5% for anesthesia induction, 1-2% for maintenance with frequent monitoring of the hind-limb withdrawal reflex and anesthesia adjustments, accordingly) and analgesia by subdermal injection of buprenorphine (0.1 mg/kg body weight) and carprofen (5 mg/kg body weight). The left cochlea was exposed by performing a retroauricular incision behind the pinna followed by a bullostomy, where the round window was visualized and punctured. A 200 μm optical fiber coupled to either a 594 nm (OBIS LS OPSL, 100 mW, Coherent Inc., Santa Clara, CA, United States) laser. Laser power was calibrated prior to each experiment using a laser power meter (LaserCheck, Coherent Inc., Santa Clara, CA, United States).

Auditory brainstem responses (ABR). Stimulus generation and delivery, as well as data acquisition was performed using a custom-written software (MATLAB, MathWorks, Natick, MA, United States) employing National Instrument data acquisition cards and a custom-build laser-controller. Recordings were conducted in a soundproof chamber (IAC Acoustics, IL, United States). Optically evoked ABRs (oABRs) were recorded by placing needle electrodes behind the pinna, on the vertex, and on the back of the anesthetized mice. The difference in potential between the vertex and mastoid subdermal needles was amplified using a custom-designed amplifier, sampled at a rate of 50 kHz for 20 ms, filtered (300-3000 Hz) and averaged across 1000 stimulus presentations. The oABRs threshold was defined and determined as the lowest light intensity for which one of the 3 waves was reliably visible. The latency of a given wave was defined as the time delay between the stimulus onset and the peak of the wave of interest. The amplitude was defined as the difference response strength between positive peak (P) and the negative (N), of a wave of interest.

The results are shown in FIGS. 5A, 5B and 5D-5I.

Application to the auditory system, for which optogenetic hearing restoration represents a future clinical application of optogenetics, exemplifies the benefit of the T218L/S220A mutant of R/CCR1. Studying the dependence of optogenetically evoked spiral ganglion neuron (SGN) activity on radiant flux (see FIG. 5G), pulse duration (see FIG. 5H) and repetition rate (see FIG. 5I) was investigated on a population level by oABR 1-st wave analysis. As demonstrated by the shown results the optogenetic stimulation of the auditory pathway by the T218L/S220A mutant of R/CCR1 enables stimulation of the auditory pathway at substantially lower light intensity than wild-type R/CCR1 (see FIG. 5D). This benefit can be critical for the clinical application, as the daily energy budget of optogenetic hearing restoration needs to comply with what one battery pack can supply in order to meet the expectations of the users.

LIST OF REFERENCES

WO 2012/032103
WO 03/084994
WO 2013/071231
U.S. Pat. No. 8,759,492 B2
WO 2017/207761
WO 2017/207745
WO 2020/150093
[1] Nagel, G., Ollig, D., Fuhrmann, M., Kateriya, S., Musti, A. M., Bamberg, E., and Hegemann, P. (2002) Channelrhodopsin-1: a light-gated proton channel in green algae, Science 296, 2395-2398.
[2] Nagel, G., Szellas, T., Huhn, W., Kateriya, S., Adeishvili, N., Berthold, P., Ollig, D., Hegemann, P., and Bamberg, E. (2003) Channelrhodopsin-2, a directly light-gated cation-selective membrane channel, *Proc Natl Acad Sci USA* 100, 13940-13945.

[3] Boyden, E. S., Zhang, F., Bamberg, E., Nagel, G., and Deisseroth, K. (2005) Millisecond-timescale, genetically targeted optical control of neural activity, *Nat Neurosci* 8, 1263-1268.
[4] Volkov, O., Kovalev, K., Polovinkin, V., Borshchevskiy, V., Bamann, C., Astashkin, R., Marin, E., Popov, A., Balandin, T., Willbold, D., Buldt, G., Bamberg, E., and Gordeliy, V. (2017) Structural insights into ion conduction by channelrhodopsin 2, *Science* 358.
[5] Sahel, J. A., Boulanger-Scemama, E., Pagot, C., Arleo, A., Galluppi, F., Martel, J. N., Esposti, S. D., Delaux, A., de Saint Aubert, J. B., de Montleau, C., Gutman, E., Audo, I., Duebel, J., Picaud, S., Dalkara, D., Blouin, L., Taiel, M., and Roska, B. (2021) Partial recovery of visual function in a blind patient after optogenetic therapy, *Nat Med* 27, 1223-1229.
[6] Dieter, A., Keppeler, D., and Moser, T. (2020) Towards the optical cochlear implant: optogenetic approaches for hearing restoration, *EMBO Mol Med* 12, e11618.
[7] Govorunova, E. G., Sineshchekov, O. A., Janz, R., Liu, X., and Spudich, J. L. (2015) NEUROSCIENCE. Natural light-gated anion channels: A family of microbial rhodopsins for advanced optogenetics, *Science* 349, 647-650.
[8] Govorunova, E. G., Gou, Y., Sineshchekov, O. A., Li, H., Wang, Y., Brown, L. S., Xue, M., Spudich, J. L. (2021) Kalium rhodopsins: Natural light-gated potassium channels, In *bioRxiv.*
[9] Klapoetke, N. C., Murata, Y., Kim, S. S., Pulver, S. R., Birdsey-Benson, A., Cho, Y. K., Morimoto, T. K., Chuong, A. S., Carpenter, E. J., Tian, Z., Wang, J., Xie, Y., Yan, Z., Zhang, Y., Chow, B. Y., Surek, B., Melkonian, M., Jayaraman, V., Constantine-Paton, M., Wong, G. K., and Boyden, E. S. (2014) Independent optical excitation of distinct neural populations, *Nat Methods* 11, 338-346.
[10] Kleinlogel, S., Feldbauer, K., Dempski, R. E., Fotis, H., Wood, P. G., Bamann, C., and Bamberg, E. (2011) Ultra light-sensitive and fast neuronal activation with the Ca(2)+-permeable channelrhodopsin CatCh, *Nat Neurosci* 14, 513-518.
[11] Zhang, F., Prigge, M., Beyriere, F., Tsunoda, S. P., Mattis, J., Yizhar, O., Hegemann, P., and Deisseroth, K. (2008) Red-shifted optogenetic excitation: a tool for fast neural control derived from Volvox carten, *Nat Neurosci* 11, 631-633.
[12] Lin, J. Y., Knutsen, P. M., Muller, A., Kleinfeld, D., and Tsien, R. Y. (2013) ReaChR: a red-shifted variant of channelrhodopsin enables deep transcranial optogenetic excitation, *Nat Neurosci* 16, 1499-1508.
[13] Mager, T., Lopez de la Morena, D., Senn, V., Schlotte, J., A, D. E., Feldbauer, K., Wrobel, C., Jung, S., Bodensiek, K., Rankovic, V., Browne, L., Huet, A., Juttner, J., Wood, P. G., Letzkus, J. J., Moser, T., and Bamberg, E. (2018) High frequency neural spiking and auditory signaling by ultrafast red-shifted optogenetics, *Nat Commun* 9, 1750.
[14] Feldbauer, K., Zimmermann, D., Pintschovius, V., Spitz, J., Bamann, C., and Bamberg, E. (2009) Channelrhodopsin-2 is a leaky proton pump, *Proc Natl Acad Sci USA* 106, 12317-12322.
[15] Berndt, A., Schoenenberger, P., Mattis, J., Tye, K. M., Deisseroth, K., Hegemann, P., and Oertner, T. G. (2011) High-efficiency channelrhodopsins for fast neuronal stimulation at low light levels, *Proc Natl Acad Sci USA* 108, 7595-7600.
[16] Marshel, J. H., Kim, Y. S., Machado, T. A., Quirin, S., Benson, B., Kadmon, J., Raja, C., Chibukhchyan, A., Ramakrishnan, C., Inoue, M., Shane, J. C., McKnight, D.

J., Yoshizawa, S., Kato, H. E., Ganguli, S., and Deisseroth, K. (2019) Cortical layer-specific critical dynamics triggering perception, *Science* 365.

[17] Sineshchekov, 0. A., Govorunova, E. G., Li, H., Wang, Y., Melkonian, M., Wong, G. K., Brown, L. S., and Spudich, J. L. (2020) Conductance Mechanisms of Rapidly Desensitizing Cation Channelrhodopsins from Cryptophyte Algae, *mBio* 11.

[18] Kishi, K. E., Kim, Y. S., Fukuda, M., Kusakizako T., Thadhani, E., Byrne, E. F. X., Paggi, J. M., Ramakrishnan, C., Matsui, T. E., Yamashita, K., Nagata, T., Konno, M., Wang, P. Y., Inoue, M., Benster, T., Uemura, T., Liu, K., Shibata, M., Nomura, N., Iwata, S., Nureki, O., Dror, R. O., Inoue, K., Deisseroth, K., Kato, H. E. (2021) Structural basis for channel conduction in the pump-likechannelrhodopsin ChRmine, *bioRxiv.*

[19] Müller, M., Bamann, C., Bamberg, E., and Kuhlbrandt, W. (2015) Light-induced helix movements in channelrhodopsin-2, *J Mol Biol* 427, 341-349.

[20] Sattig, T., Rickert, C., Bamberg, E., Steinhoff, H. J., and Bamann, C. (2013) Light-induced movement of the transmembrane helix B in channelrhodopsin-2, *Angew Chem Int Ed Engl* 52, 9705-9708.

[21] Lorenz-Fonfria, V. A., Resler, T., Krause, N., Nack, M., Gossing, M., Fischer von Mollard, G., Bamann, C., Bamberg, E., Schlesinger, R., and Heberle, J. (2013) Transient protonation changes in channelrhodopsin-2 and their relevance to channel gating, *Proc Natl Acad Sci USA* 110, E1273-1281.

[22] Lorenz-Fonfria, V. A., Bamann, C., Resler, T., Schlesinger, R., Bamberg, E., and Heberle, J. (2015) Temporal evolution of helix hydration in a light-gated ion channel correlates with ion conductance, *Proc Natl Acad Sci USA* 112, E5796-5804.

[23] Zhang, H., and Cohen, A. E. (2017) Optogenetic Approaches to Drug Discovery in Neuroscience and Beyond, Trends Biotechnol 35, 625-639.

[24] Agus, V., and Janovjak, H. (2017) Optogenetic methods in drug screening: technologies and applications, Curr Opin Biotechnol 48, 8-14.

[25] Kleinlogel, S., Vogl, C., Jeschke, M., Neef, J., and Moser T. (2020) Emerging Approaches for restoration of hearing and vision, Physiol Rev 100, 1467-1525.

[26] Gradinaru, V., Zhang, F., Ramakrishnan, C., Mattis, J., Prakash, R., Diester, I., Goshen, I., Thompson, K. R., and Deisseroth, K. (2010) Molecular and cellular approaches for diversifying and extending optogenetics. *Cell* 141, 154-165

[27] Keppeler, D., Merino, R. M., Lopez de la Morena, D., Bali, B., Huet, A. T., Gehrt, A., Wrobel, C., Subramanian, S., Dombrowski, T., Wolf, F., Rankovic, V., Neef, A., and Moser, T. (2018) Ultrafast optogenetic stimulation of the auditory pathway by targeting-optimized Chronos. *EMBO J.*

The invention claimed is:

1. A mutant ion channel, wherein the mutant ion channel comprises a 7-transmembrane-helix motif having an amino acid sequence identical with the full-length sequence of the 7-transmembrane-helix motif of the wild-type ion channel RICCR1 set forth in SEQ ID NO:9, except for one or both of:

(i) Leu, Ile or Val at the amino acid position corresponding to T218 in SEQ ID NO:5;

(ii) Ala, Gly or Val at the amino acid position corresponding to S220 in SEQ ID NO:5;

and, optionally, one or more of:

(iii) Phe at the amino acid position corresponding to Y260 in SEQ ID NO:5, (iv) His at the amino acid position corresponding to R136 in SEQ ID NO:5, (v) Trp at the amino acid position corresponding to S138 in SEQ ID NO:5, (vi) Phe at the amino acid position corresponding to Y156 in SEQ ID NO:5, (vii) Phe at the amino acid position corresponding to Y116 in SEQ ID NO:5, (viii) Val at the amino acid position corresponding to T119 in SEQ ID NO:5; and wherein the mutant ion channel is capable of being activated by light; and wherein if there is Ala at the amino acid position corresponding to S220 in SEQ ID NO:5, there is Leu, Ile or Val at the amino acid position corresponding to T218 in SEQ ID NO:5.

2. The mutant ion channel of claim 1, wherein the mutant ion channel further shows reduced light-dependent desensitization compared to a reference ion channel which has a Thr at the amino acid position corresponding to position 218 in SEQ ID NO: 5 and a Ser at the amino acid position corresponding to position 220 in SEQ ID NO:5 and otherwise is identical to the mutant ion channel.

3. The mutant ion channel of claim 1, wherein the amino acid at the position corresponding to position T218 in SEQ ID NO:5 is Leu.

4. The mutant ion channel of claim 1, wherein the amino acid at the position corresponding to position S220 in SEQ ID NO:5 is Ala.

5. The mutant ion channel of claim 1, wherein the amino acid at the amino acid position corresponding to T119 in SEQ ID NO:5 is Val.

6. The mutant ion channel of claim 1, wherein the mutant ion channel provides an at least 1.5-times, at least 1.7-times, or at least 2.0-times, and, optionally, up to 3.5-times, up to 3.0-times, or up to 2.9-times, higher stationary-peak-ratio than a reference ion channel which has a Thr at the amino acid position corresponding to position 218 in SEQ ID NO: 5 and a Ser at the amino acid position corresponding to position 220 in SEQ ID NO:5 and otherwise is identical to the mutant ion channel;

wherein the stationary-peak-ratio is measurable by whole-cell patch-clamp measurement of photocurrents in an NG108-15 cell expressing the mutant ion channel or the reference ion channel, respectively, at a membrane potential of –60 mV, in said whole-cell patch-clamp measurement, the photocurrents are measured upon illumination of the NG108-15 cell with a 2 s light pulse of a wavelength of 532 nm at saturating intensity of 23 mW/mm$^2$ to determine the mean stationary current of the last 100 ms of the 2 s light pulse and the peak current of the 2 s light pulse; and wherein the stationary-peak-ratio is the quotient of the mean stationary current of the last 100 ms of the 2 s light pulse and the peak current of the 2 s light pulse.

7. The mutant ion channel of claim 1, wherein the mutant ion channel provides an at least 1.5-times, at least 1.7-times, or at least 2.0-times, and, optionally, up to 3.5-times, up to 3.0-times, or up to 2.9-times, higher mean stationary-peak-ratio than a reference ion channel which has a Thr at the amino acid position corresponding to position 218 in SEQ ID NO:5 and a Ser at the amino acid position corresponding to position 220 in SEQ ID NO: 5 and otherwise is identical to the mutant ion channel;

wherein the mean stationary-peak-ratio is the mean of the stationary-peak-ratios of at least 5, at least 10, at least 15, e.g., 5-100, 10-75 or 15-60 individual NG108-15 cells expressing the mutant ion channel or from the stationary photocurrent densities of the same number of individual NG108-15 cells expressing the reference ion channel, respectively;

wherein the stationary-peak-ratio of an individual NG108-15 cell is measurable by whole-cell patch-clamp measurement of photocurrents in the NG108-15 cell at a membrane potential of –60 mV, in said whole-cell patch-clamp measurement, the photocurrents are measured upon illumination of the NG108-15 cell with a 2 s light pulse of a wavelength of 532 nm at saturating intensity of 23 mW/mm$^2$ to determine the mean stationary current of the last 100 ms of the 2 s light pulse and the peak current of the 2 s light pulse; and wherein the stationary-peak-ratio of the NG108-15 cell is the quotient of the mean stationary current of the last 100 ms of the 2 s light pulse and the peak current of the 2 s light pulse.

8. The mutant ion channel of claim 1, wherein the mutant ion channel provides an at least 1.5-times, at least 1.7-times, or at least 2.0-times, and, e.g., up to 5.5-times, up to 5.0-times, or up to 4.5-times, higher stationary photocurrent density than a reference ion channel which has a Thr at the amino acid position corresponding to position 218 in SEQ ID NO: 5 and a Ser at the amino acid position corresponding to position 220 in SEQ ID NO:5 and otherwise is identical to the mutant ion channel;

wherein the stationary photocurrent density is measurable by whole-cell patch-clamp measurements with an NG108-15 cell expressing the mutant ion channel or the reference ion channel, respectively;

in said whole-cell patch-clamp measurements:

transient capacitive currents in response to voltage steps are measured to determine the capacitance of the NG108-15 cell, and photocurrents at a membrane potential of –60 mV are measured upon illumination of the NG108-15 cell with a 2 s light pulse of a wavelength of 532 nm at saturating intensity of 23 mW/mm$^2$ to determine the mean stationary current of the last 100 ms of the 2 s light pulse; and wherein the stationary photocurrent density is the quotient of the mean stationary current of the last 100 ms of the 2 s light pulse and the capacitance.

9. The mutant ion channel of claim 1, wherein the mutant ion channel provides an at least 1.5-times, at least 1.7-times, or at least 2.0-times, and, e.g., up to 5.5-times, up to 5.0-times, or up to 4.5-times, higher mean stationary photocurrent density than a reference ion channel which has a Thr at the amino acid position corresponding to position 218 in SEQ ID NO:5 and a Ser at the amino acid position corresponding to position 220 in SEQ ID NO: 5 and otherwise is identical to the mutant ion channel;

wherein the mean stationary photocurrent density is the mean of the stationary photocurrent densities of at least 5, at least 10, at least 15, e.g., 5-100, 10-75 or 15-60 individual NG108-15 cells expressing the mutant ion channel or from the stationary photocurrent densities of the same number of individual NG108-15 cells expressing the reference ion channel, respectively;

wherein the stationary photocurrent density of an individual NG108-15 cell is measurable by whole-cell patch-clamp measurements;

in said whole-cell patch-clamp measurements:

transient capacitive currents in response to voltage steps are measured to determine the capacitance of the NG108-15 cell, and photocurrents at a membrane potential of –60 mV are measured upon illumination of the NG108-15 cell with a 2 s light pulse of a wavelength of 532 nm at saturating intensity of 23 mW/mm$^2$ to determine the mean stationary current of the last 100 ms of the 2 s light pulse; and wherein the stationary photocurrent density of the NG108-15 cell is the quotient of the mean stationary current of the last 100 ms of the 2 s light pulse and the capacitance of the NG108-15 cell.

10. The mutant ion channel of claim 1, wherein:

(a) the amino acid at the position corresponding to position T218 in SEQ ID NO:5 is Leu, and the amino acid at the position corresponding to position S220 in SEQ ID NO:5 is Ala; or (b) the amino acid at the position corresponding to position T218 in SEQ ID NO:5 is Leu, and the amino acid at the position corresponding to position S220 in SEQ ID NO:5 is Ser.

11. A method of treating or ameliorating loss of vision or loss of hearing in a patient in need thereof, the method comprising administering a nucleic acid encoding the mutant ion channel of claim 1 to the patient.

12. The method of claim 11, wherein the nucleic acid is introduced into spiral ganglion neurons of a human or a non-human animal and renders said neurons light-sensitive.

13. The method of claim 12, wherein the human or non-human animal is equipped with an optical cochlear implant to allow for at least partial restoration of hearing.

14. The method of claim 11, wherein the amino acid at the position corresponding to position T218 in SEQ ID NO:5 is Leu, and/or wherein the amino acid at the position corresponding to position S220 in SEQ ID NO:5 is Ala.

\* \* \* \* \*

SEQUENCE LISTING

```
Sequence total quantity: 19
SEQ ID NO: 1            moltype = AA  length = 315
FEATURE                Location/Qualifiers
source                 1..315
                       mol_type = protein
                       organism = Chlamydomonas reinhardtii
SEQUENCE: 1
MDYGGALSAV GRELLFVTNP VVVNGSVLVP EDQCYCAGWI ESRGTNGAQT ASNVLQWLAA  60
GFSILLLMFY AYQTWKSTCG WEEIYVCAIE MVKVILEFFF EFKNPSMLYL ATGHRVQWLR  120
YAEWLLTCPV ILIHLSNLTG LSNDYSRRTM GLLVSDIGTI VWGATSAMAT GYVKVIFFCL  180
GLCYGANTFF HAAKAYIEGY HTVPKGRCRQ VVTGMAWLFF VSWGMFPILF ILGPEGFGVL  240
SVYGSTVGHT IIDLMSKNCW GLLGHYLRVL IHEHILIHGD IRKTTKLNIG GTEIEVETLV  300
EDEAEAGAVN KGTGK                                                   315

SEQ ID NO: 2            moltype = AA  length = 350
FEATURE                Location/Qualifiers
source                 1..350
                       mol_type = protein
                       organism = Chlamydomonas noctigama
SEQUENCE: 2
MAELISSATR SLFAAGGINP WPNPYHHEDM GCGGMTPTGE CFSTEWWCDP SYGLSDAGYG  60
YCFVEATGGY LVVGVEKKQA WLHSRGTPGE KIGAQVCQWI AFSIAIALLT FYGFSAWKAT  120
CGWEEVYVCC VEVLFVTLEI FKEFSSPATV YLSTGNHAYC LRYFEWLLSC PVILIKLSNL  180
SGLKNDYSKR TMGLIVSCVG MIVFGMAAGL ATDWLKWLLY IVSCIYGGYM YFQAAKCYVE  240
ANHSVPKGHC RMVVKLMAYA YFASWGSYPI LWAVGPEGLL KLSPYANSIG HSICDIIAKE  300
FWTFLAHHLR IKIHEHILIH GDIRKTTKME IGGEEVEVEE FVEEEDEDTV             350

SEQ ID NO: 3            moltype = AA  length = 300
FEATURE                Location/Qualifiers
REGION                 1..300
                       note = VChR1; channel rhodopsin 1 derived from Volvox
                        carteri
source                 1..300
                       mol_type = protein
                       organism = synthetic construct
SEQUENCE: 3
MDYPVARSLI VRYPTDLGNG TVCMPRGQCY CEGWLRSRGT SIEKTIAITL QWVVFALSVA  60
CLGWYAYQAW RATCGWEEVY VALIEMMKSI IEAFHEFDSP ATLWLSSGNG VVWMRYGEWL  120
LTCPVLLIHL SNLTGLKDDY SKRTMGLLVS DVGCIVWGAT SAMCTGWTKI LFFLISLSYG  180
MYTYFHAAKV YIEAFHTVPK GICRELVRVM AWTFFVAWGM FPVLFLLGTE GFGHISPYGS  240
AIGHSILDLI AKNMWGVLGN YLRVKIHEHI LLYGDIRKKQ KITIAGQEME VETLVAEEED  300

SEQ ID NO: 4            moltype = AA  length = 350
```

-continued

```
FEATURE              Location/Qualifiers
REGION               1..350
                     note = ReAChR; chimeric channelrhodopsin variant
source               1..350
                     mol_type = protein
                     organism = synthetic construct
SEQUENCE: 4
MVSRRPWLLA LALAVALAAG SAGASTGSDA TVPVATQDGP DYVFHRAHER MLFQTSYTLE    60
NNGSVICIPN NGQCFCLAWL KSNGTNAEKL AANILQWVVF ALSVACLGWY AYQAWRATCG    120
WEEVYVALIE MMKSIIEAFH EFDSPATLWL SSGNGVVWMR YGEWLLTCPV ILIHLSNLTG    180
LKDDYSKRTM GLLVSDVGCI VWGATSAMCT GWTKILFFLI SLSYGMYTYF HAAKVYIEAF    240
HTVPKGLCRQ LVRAMAWLFF VSWGMFPVLF LLGPEGFGHI SPYGSAIGHS ILDLIAKNMW    300
GVLGNYLRVK IHEHILLYGD IRKKQKITIA GQEMEVETLV AEEEDKYESS              350

SEQ ID NO: 5         moltype = AA   length = 309
FEATURE              Location/Qualifiers
REGION               1..309
                     note = ChRmine; RICCR1; bacteriorhodopsin-like
                      channelrhodopsin derived from Rhodomonas lens
source               1..309
                     mol_type = protein
                     organism = synthetic construct
SEQUENCE: 5
MAHAPGTDQM FYVGTMDGWY LDTKLNSVAI GAHWSCFIVL TITTFYLGYE SWTSRGPSKR    60
TSFYAGYQEE QNLALFVNFF AMLSYFGKIV ADTLGHNFGD VGPFIIGFGN YRYADYMLTC    120
PMLVYDLLYQ LRAPYRVSCS AIIFAILMSG VLAEFYAEGD PRLRNGAYAW YGFGCFWFIF    180
AYSIVMSIVA KQYSRLAQLA QDTGAEHSLH VLKFAVFTFS MLWILFPLVW AICPRGFGWI    240
DDNWTEVAHC VCDIVAKSCY GFALARFRKT YDEELFRLLE QLGHDEDEFQ KLELDMRLSS    300
NGERLRRLS                                                           309

SEQ ID NO: 6         moltype = AA   length = 309
FEATURE              Location/Qualifiers
REGION               1..309
                     note = T218L mutant of ChRmine (RICCR1)
source               1..309
                     mol_type = protein
                     organism = synthetic construct
SEQUENCE: 6
MAHAPGTDQM FYVGTMDGWY LDTKLNSVAI GAHWSCFIVL TITTFYLGYE SWTSRGPSKR    60
TSFYAGYQEE QNLALFVNFF AMLSYFGKIV ADTLGHNFGD VGPFIIGFGN YRYADYMLTC    120
PMLVYDLLYQ LRAPYRVSCS AIIFAILMSG VLAEFYAEGD PRLRNGAYAW YGFGCFWFIF    180
AYSIVMSIVA KQYSRLAQLA QDTGAEHSLH VLKFAVFLFS MLWILFPLVW AICPRGFGWI    240
DDNWTEVAHC VCDIVAKSCY GFALARFRKT YDEELFRLLE QLGHDEDEFQ KLELDMRLSS    300
NGERLRRLS                                                           309

SEQ ID NO: 7         moltype = AA   length = 309
FEATURE              Location/Qualifiers
REGION               1..309
                     note = S220A mutant of ChRmine (RICCR1)
source               1..309
                     mol_type = protein
                     organism = synthetic construct
SEQUENCE: 7
MAHAPGTDQM FYVGTMDGWY LDTKLNSVAI GAHWSCFIVL TITTFYLGYE SWTSRGPSKR    60
TSFYAGYQEE QNLALFVNFF AMLSYFGKIV ADTLGHNFGD VGPFIIGFGN YRYADYMLTC    120
PMLVYDLLYQ LRAPYRVSCS AIIFAILMSG VLAEFYAEGD PRLRNGAYAW YGFGCFWFIF    180
AYSIVMSIVA KQYSRLAQLA QDTGAEHSLH VLKFAVFTFA MLWILFPLVW AICPRGFGWI    240
DDNWTEVAHC VCDIVAKSCY GFALARFRKT YDEELFRLLE QLGHDEDEFQ KLELDMRLSS    300
NGERLRRLS                                                           309

SEQ ID NO: 8         moltype = AA   length = 309
FEATURE              Location/Qualifiers
REGION               1..309
                     note = T218L+S220A mutant of ChRmine (RICCR1)
source               1..309
                     mol_type = protein
                     organism = synthetic construct
SEQUENCE: 8
MAHAPGTDQM FYVGTMDGWY LDTKLNSVAI GAHWSCFIVL TITTFYLGYE SWTSRGPSKR    60
TSFYAGYQEE QNLALFVNFF AMLSYFGKIV ADTLGHNFGD VGPFIIGFGN YRYADYMLTC    120
PMLVYDLLYQ LRAPYRVSCS AIIFAILMSG VLAEFYAEGD PRLRNGAYAW YGFGCFWFIF    180
AYSIVMSIVA KQYSRLAQLA QDTGAEHSLH VLKFAVFLFA MLWILFPLVW AICPRGFGWI    240
DDNWTEVAHC VCDIVAKSCY GFALARFRKT YDEELFRLLE QLGHDEDEFQ KLELDMRLSS    300
NGERLRRLS                                                           309

SEQ ID NO: 9         moltype = AA   length = 243
FEATURE              Location/Qualifiers
REGION               1..243
                     note = 7-transmembrane-helix motif of ChRmine (RICCR1)
```

-continued

```
source                  1..243
                        mol_type = protein
                        organism = synthetic construct
SEQUENCE: 9
SVAIGAHWSC FIVLTITTFY LGYESWTSRG PSKRTSFYAG YQEEQNLALF VNFFAMLSYF  60
GKIVADTLGH NFGDVGPFII GFGNYRYADY MLTCPMLVYD LLYQLRAPYR VSCSAIIFAI  120
LMSGVLAEFY AEGDPRLRNG AYAWYGFGCF WFIFAYSIVM SIVAKQYSRL AQLAQDTGAE  180
HSLHVLKFAV FTFSMLWILF PLVWAICPRG FGWIDDNWTE VAHCVCDIVA KSCYGFALAR  240
FRK                                                                243

SEQ ID NO: 10           moltype = AA  length = 243
FEATURE                 Location/Qualifiers
REGION                  1..243
                        note = T218L mutant of 7-transmembrane-helix motif of
                         ChRmine (RICCR1)
source                  1..243
                        mol_type = protein
                        organism = synthetic construct
SEQUENCE: 10
SVAIGAHWSC FIVLTITTFY LGYESWTSRG PSKRTSFYAG YQEEQNLALF VNFFAMLSYF  60
GKIVADTLGH NFGDVGPFII GFGNYRYADY MLTCPMLVYD LLYQLRAPYR VSCSAIIFAI  120
LMSGVLAEFY AEGDPRLRNG AYAWYGFGCF WFIFAYSIVM SIVAKQYSRL AQLAQDTGAE  180
HSLHVLKFAV FLFSMLWILF PLVWAICPRG FGWIDDNWTE VAHCVCDIVA KSCYGFALAR  240
FRK                                                                243

SEQ ID NO: 11           moltype = AA  length = 243
FEATURE                 Location/Qualifiers
REGION                  1..243
                        note = S220A mutant of 7-transmembrane-helix motif of
                         ChRmine (RICCR1)
source                  1..243
                        mol_type = protein
                        organism = synthetic construct
SEQUENCE: 11
SVAIGAHWSC FIVLTITTFY LGYESWTSRG PSKRTSFYAG YQEEQNLALF VNFFAMLSYF  60
GKIVADTLGH NFGDVGPFII GFGNYRYADY MLTCPMLVYD LLYQLRAPYR VSCSAIIFAI  120
LMSGVLAEFY AEGDPRLRNG AYAWYGFGCF WFIFAYSIVM SIVAKQYSRL AQLAQDTGAE  180
HSLHVLKFAV FTFAMLWILF PLVWAICPRG FGWIDDNWTE VAHCVCDIVA KSCYGFALAR  240
FRK                                                                243

SEQ ID NO: 12           moltype = AA  length = 243
FEATURE                 Location/Qualifiers
REGION                  1..243
                        note = T218L+S220A mutant of 7-transmembrane-helix motif of
                         ChRmine (RICCR1)
source                  1..243
                        mol_type = protein
                        organism = synthetic construct
SEQUENCE: 12
SVAIGAHWSC FIVLTITTFY LGYESWTSRG PSKRTSFYAG YQEEQNLALF VNFFAMLSYF  60
GKIVADTLGH NFGDVGPFII GFGNYRYADY MLTCPMLVYD LLYQLRAPYR VSCSAIIFAI  120
LMSGVLAEFY AEGDPRLRNG AYAWYGFGCF WFIFAYSIVM SIVAKQYSRL AQLAQDTGAE  180
HSLHVLKFAV FLFAMLWILF PLVWAICPRG FGWIDDNWTE VAHCVCDIVA KSCYGFALAR  240
FRK                                                                243

SEQ ID NO: 13           moltype = AA  length = 28
FEATURE                 Location/Qualifiers
REGION                  1..28
                        note = variants of helix 6 motif of RICCR1
VARIANT                 14
                        note = in wild-type or wild-type like variant selected from
                         T, S, Y, Q and N; in improved mutant selected from L, I,
                         V, M, C, F, A, G, P and W
VARIANT                 16
                        note = in wild-type or wild-type like variant selected from
                         S, T, Y, Q and N; in improved mutant selected from A, G,
                         L, V, I, M, P, C and W
source                  1..28
                        mol_type = protein
                        organism = synthetic construct
SEQUENCE: 13
AEHSLHVLKF AVFXFXMLWI LFPLVWAI                                      28

SEQ ID NO: 14           moltype = DNA  length = 30
FEATURE                 Location/Qualifiers
misc_feature            1..30
                        note = forward primer humanized RICCR1 T218L
source                  1..30
                        mol_type = other DNA
```

-continued

```
                          organism = synthetic construct
SEQUENCE: 14
gttcgccgtg tttctgttct ccatgctgtg                                    30

SEQ ID NO: 15            moltype = DNA  length = 30
FEATURE                  Location/Qualifiers
misc_feature             1..30
                         note = reverse primer humanized RICCR1 T218L
source                   1..30
                         mol_type = other DNA
                         organism = synthetic construct
SEQUENCE: 15
cacagcatgg agaacagaaa cacggcgaac                                     30

SEQ ID NO: 16            moltype = DNA  length = 28
FEATURE                  Location/Qualifiers
misc_feature             1..28
                         note = forward primer humanized RICCR1 S220A
source                   1..28
                         mol_type = other DNA
                         organism = synthetic construct
SEQUENCE: 16
gtgtttacct tcgccatgct gtggattc                                      28

SEQ ID NO: 17            moltype = DNA  length = 28
FEATURE                  Location/Qualifiers
misc_feature             1..28
                         note = reverse primer humanized RICCR1 S220A
source                   1..28
                         mol_type = other DNA
                         organism = synthetic construct
SEQUENCE: 17
gaatccacag catggcgaag gtaaacac                                      28

SEQ ID NO: 18            moltype = DNA  length = 31
FEATURE                  Location/Qualifiers
misc_feature             1..31
                         note = forward primer humanized RICCR1 T218L+S220A
source                   1..31
                         mol_type = other DNA
                         organism = synthetic construct
SEQUENCE: 18
cgtgtttctg ttcgccatgc tgtggattct g                                  31

SEQ ID NO: 19            moltype = DNA  length = 31
FEATURE                  Location/Qualifiers
misc_feature             1..31
                         note = reverse primer humanized RICCR1 T218L+S220A
source                   1..31
                         mol_type = other DNA
                         organism = synthetic construct
SEQUENCE: 19
cagaatccac agcatggcga acagaaacac g                                  31
```